(12) United States Patent
Rudert et al.

(10) Patent No.: US 7,049,135 B2
(45) Date of Patent: May 23, 2006

(54) METHOD AND PHAGE FOR THE IDENTIFICATION OF NUCLEIC ACID SEQUENCES ENCODING MEMBERS OF A MULTIMERIC (POLY)PEPTIDE COMPLEX

(75) Inventors: Fritz Rudert, Munich (DE); Liming Ge, Munich (DE); Vic Ilag, Munich (DE)

(73) Assignee: Morphosys AG, (DE)

( * ) Notice: Subject to any disclaimer, the term of this patent is extended or adjusted under 35 U.S.C. 154(b) by 0 days.

(21) Appl. No.: 10/634,862

(22) Filed: Aug. 6, 2003

(65) Prior Publication Data

US 2004/0048383 A1    Mar. 11, 2004

Related U.S. Application Data

(60) Division of application No. 09/495,880, filed on Feb. 1, 2001, now Pat. No. 6,667,150, which is a continuation of application No. PCT/EP98/04836, filed on Aug. 3, 1998.

(30) Foreign Application Priority Data

Aug. 1, 1997    (EP) ................. 97113319

(51) Int. Cl.
  *C12N 15/70* (2006.01)
  *C12N 15/74* (2006.01)
  *C12N 7/01* (2006.01)
(52) U.S. Cl. .................... 435/320.1; 435/235.1; 435/472
(58) Field of Classification Search ............ 435/235.1, 435/320.1, 472
  See application file for complete search history.

(56) References Cited

U.S. PATENT DOCUMENTS 5,514,548 A  *  5/1996  Krebber et al. ............. 435/6

FOREIGN PATENT DOCUMENTS

| WO | WO 88/06630 | 7/1988 |
| WO | WO 90/02809 | 3/1990 |
| WO | WO 91/17271 | 11/1991 |
| WO | WO 91/19818 | 12/1991 |
| WO | WO 9201047 | * 10/1992 |
| WO | WO 92/09690 | 11/1992 |
| WO | WO 92/20791 | 11/1992 |
| WO | WO 93/19172 | 9/1993 |
| WO | WO 95/21914 | 8/1995 |
| WO | WO 97/32017 | * 9/1997 |

OTHER PUBLICATIONS

Ackerman (Archives of Virology 141:209-218, 1996).*
Rudert et al (FEBS Letters 440:135-140, 1998).*
William O. Salivar et al., "Purification and Properties of Diploid Particles of Coliphage M13", Virology, 1967, vol. 32, pp. 41-51.
Vincenzo Enea et al., "Interference Resistance Mutants of Phage f1", Virology, 1982, vol. 122, pp. 222-226.
Javier Lopez et al., "Morphogenesis of Filamentous Bacteriophage f1: Orientation of Extrusion and Production of Polyphage", Virology, 1983, vol, 127, pp. 1770-193.
Marjorie Russel et al., "A Bacterial Gene, fip. Required for Filamentous Bacteriophage F1 Assembly", J. Bacteriology, 1983, vol. 154, No. 3, pp. 1064-1076.
John W. Crissman et al., "Gene-III Protein of Filamentous Phages: Evidence for a Carboxyl-Terminal Domain with a Role in Morphogenesis", Virology, 1984, vol. 132, pp. 445-455.
Moses V. Chao et al., "Gene Transfer and Molecular Cloning of the Human NGF Receptor", Science, 1985, vol. 232, p. 518.
Marjorie Russel et al., "Genetic Analysis of the Filamentous Bacterioiphage Packaging Signal and of the Proteins That Interact with It", J. Virology, 1989, vol. 63, No. 8, pp. 3284-3295.
Kosi Gramatikoff et al., "Direct Interaction rescue, a novel filamentous phage technique to study protein-protein interactions", Nucleic Acids Research, 1994, vol. 22, No. 25, pp. 5761-5726.
Ulrich Brinkmann et al., "Phage display of disulfide-stabilized Fv Fragments", Journal of Immunological Methods, 1997, vol. 22, pp. 28-30.
Liming Ge et al., "Simultaneous Introduction of Multiple Mutations Using Overlap Extension PCR", BioTechniques, 1997, vol. 22, pp. 28-30.
Fritz Rudert et al., "A phage-based system to select multiple protein-protein interactions simultaneously from combinatorial libraries", FEBS Letters, 1998, vol. 440, pp. 135-140.
Claus Krebber et al., "Co-selection of cognate antibody-antigen pairs by selectivety-infective phages", FEBS Letters, 1995, vol. 377, pp. 227-231.

* cited by examiner

*Primary Examiner*—Mary E. Mosher
(74) *Attorney, Agent, or Firm*—Heller Ehrman LLP

(57) ABSTRACT

The present invention relates to methods for the identification of nucleic acid sequences encoding members of a multimeric (poly)peptide complex by screening for polyphage particles. Furthermore, the invention relates to products and uses thereof for the identification of nucleic acid sequences in accordance with the present invention.

26 Claims, 39 Drawing Sheets

Figure 3A:
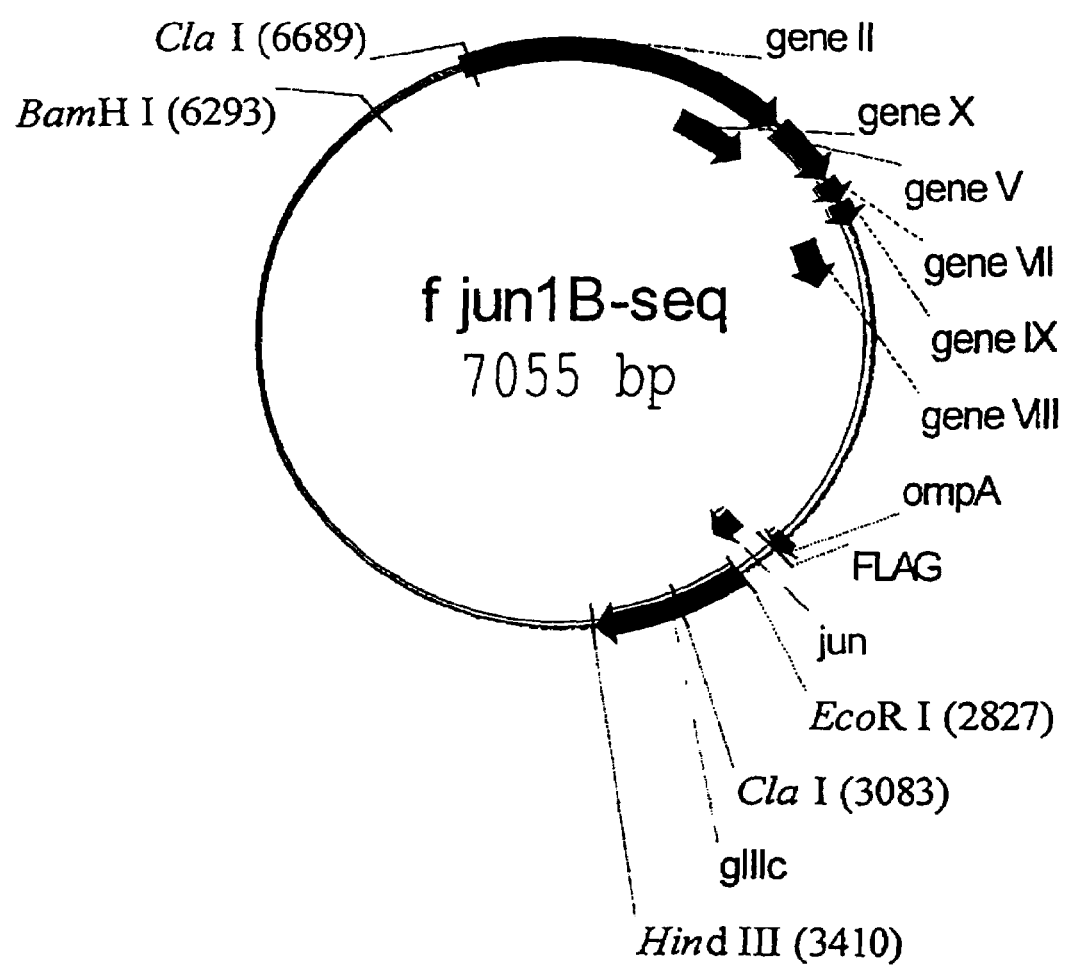

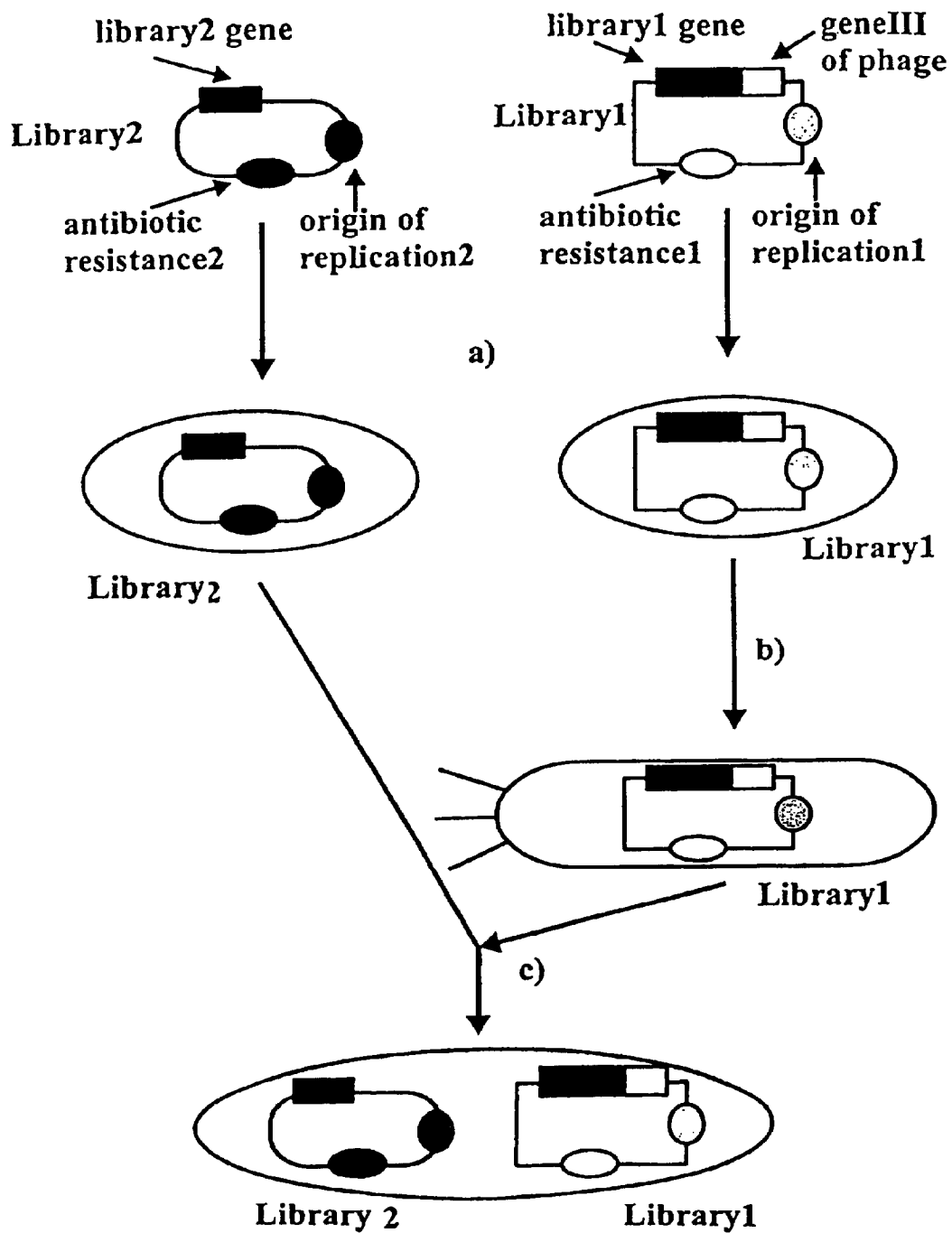
Figure 1A : General description of the polyphage principle

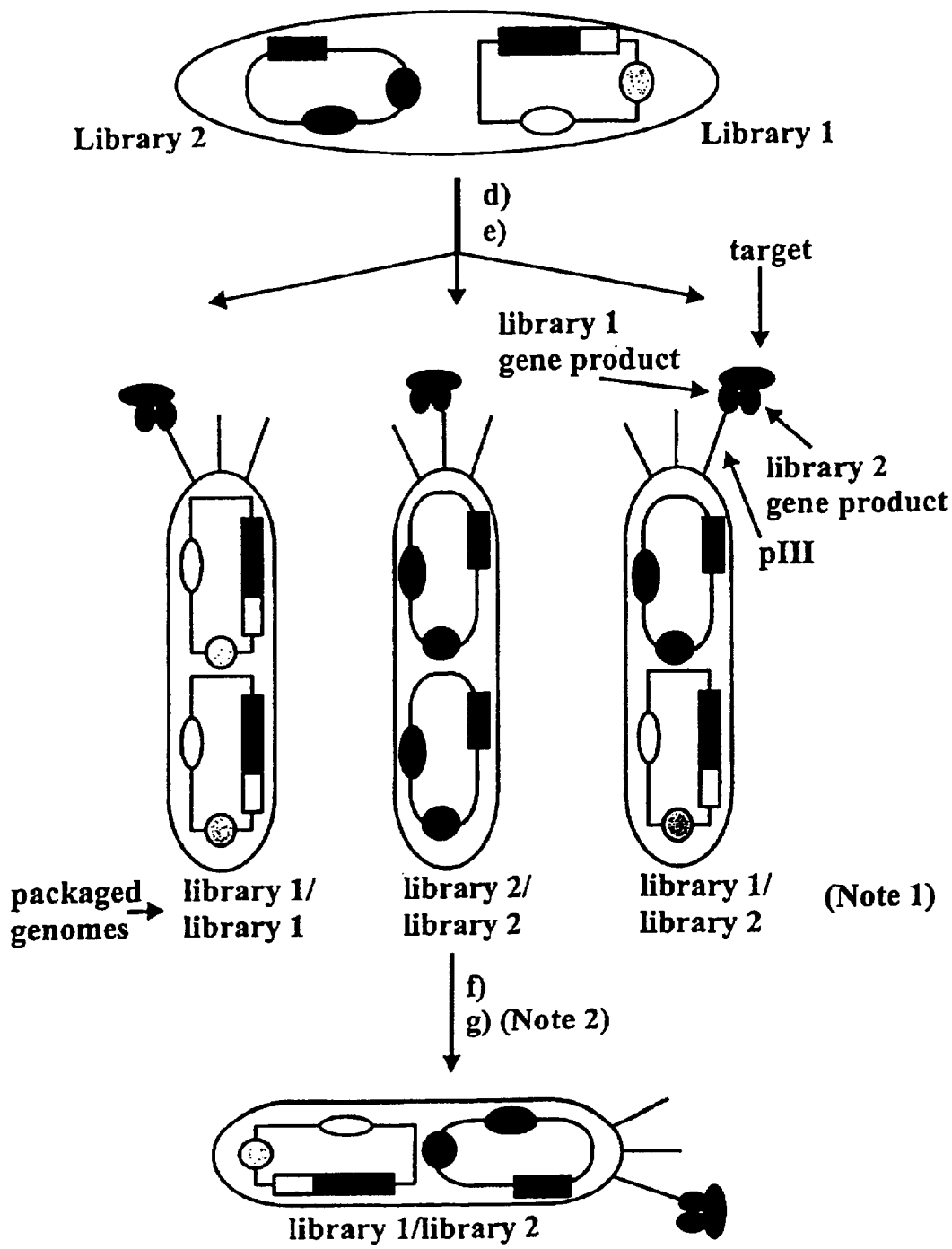
Figure 1B: General description of the polyphage principle (cont.)

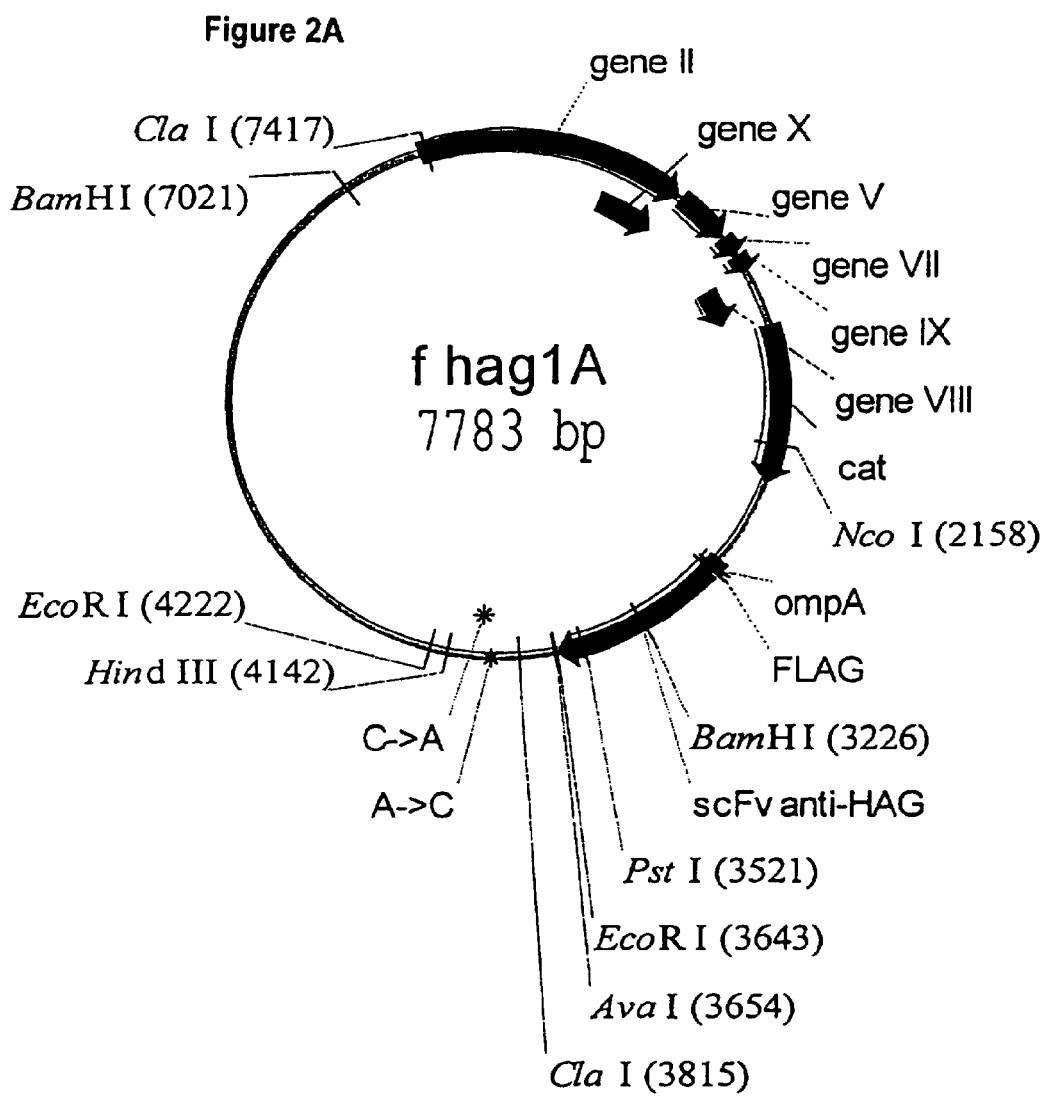

Figure 2B

```
  1  AACGCTACTA CCATTAGTAG AATTGATGCC ACCTTTTCAG CTCGCGCCCC
     TTGCGATGAT GGTAATCATC TTAACTACGG TGGAAAAGTC GAGCGCGGGG

51  AAATGAAAAT ATAGCTAAAC AGGTTATTGA CCATTTGCGA AATGTATCTA
     TTTACTTTTA TATCGATTTG TCCAATAACT GGTAAACGCT TTACATAGAT

101  ATGGTCAAAC TAAATCTACT CGTTCGCAGA ATTGGGAATC AACTGTTACA
     TACCAGTTTG ATTTAGATGA GCAAGCGTCT TAACCCTTAG TTGACAATGT

151  TGGAATGAAA CTTCCAGACA CCGTACTTTA GTTGCATATT TAAAACATGT
     ACCTTACTTT GAAGGTCTGT GGCATGAAAT CAACGTATAA ATTTTGTACA

201  TGAACTACAG CACCAGATTC AGCAATTAAG CTCTAAGCCA TCCGCAAAAA
     ACTTGATGTC GTGGTCTAAG TCGTTAATTC GAGATTCGGT AGGCGTTTTT

251  TGACCTCTTA TCAAAGGAG CAATTAAAGG TACTGTCTAA TCCTGACCTG
     ACTGGAGAAT AGTTTTCCTC GTTAATTTCC ATGACAGATT AGGACTGGAC

301  TTGGAATTTG CTTCCGGTCT GGTTCGCTTT GAGGCTCGAA TTGAAACGCG
     AACCTTAAAC GAAGGCCAGA CCAAGCGAAA CTCCGAGCTT AACTTTGCGC

351  ATATTTGAAG TCTTTCGGGC TTCCTCTTAA TCTTTTTGAT GCAATTCGCT
     TATAAACTTC AGAAAGCCCG AAGGAGAATT AGAAAAACTA CGTTAAGCGA

401  TTGCTTCTGA CTATAATAGA CAGGGTAAAG ACCTGATTTT TGATTTATGG
     AACGAAGACT GATATTATCT GTCCCATTTC TGGACTAAAA ACTAAATACC

451  TCATTCTCGT TTTCTGAACT GTTTAAAGCA TTTGAGGGGG ATTCAATGAA
     AGTAAGAGCA AAAGACTTGA CAAATTTCGT AAACTCCCCC TAAGTTACTT

501  TATTTATGAC GATTCCGCAG TATTGGACGC TATCCAGTCT AAACATTTTA
     ATAAATACTG CTAAGGCGTC ATAACCTGCG ATAGGTCAGA TTTGTAAAAT

551  CAATTACCCC CTCTGGCAAA ACTTCCTTTG CAAAAGCCTC TCGCTATTTT
     GTTAATGGGG GAGACCGTTT TGAAGGAAAC GTTTTCGGAG AGCGATAAAA

601  GGTTTCTATC GTCGTCTGGT TAATGAGGGT TATGATAGTG TTGCTCTTAC
     CCAAAGATAG CAGCAGACCA ATTACTCCCA ATACTATCAC AACGAGAATG

651  CATGCCTCGT AATTCCTTTT GGCGTTATGT ATCTGCATTA GTTGAGTGTG
     GTACGGAGCA TTAAGGAAAA CCGCAATACA TAGACGTAAT CAACTCACAC

701  GTATTCCTAA ATCTCAATTG ATGAATCTTT CCACCTGTAA TAATGTTGTT
     CATAAGGATT TAGAGTTAAC TACTTAGAAA GGTGGACATT ATTACAACAA

751  CCGTTAGTTC GTTTTATTAA CGTAGATTTT TCCTCCCAAC GTCCTGACTG
     GGCAATCAAG CAAAATAATT GCATCTAAAA AGGAGGGTTG CAGGACTGAC

801  GTATAATGAG CCAGTTCTTA AAATCGCATA AGGTAATTCA AAATGATTAA
     CATATTACTC GGTCAAGAAT TTTAGCGTAT TCCATTAAGT TTTACTAATT
```

Figure 2C

```
 851  AGTTGAAATT AAACCGTCTC AAGCGCAATT TACTACCCGT TCTGGTGTTT
      TCAACTTTAA TTTGGCAGAG TTCGCGTTAA ATGATGGGCA AGACCACAAA

901  CTCGTCAGGG CAAGCCTTAT TCACTGAATG AGCAGCTTTG TTACGTTGAT
      GAGCAGTCCC GTTCGGAATA AGTGACTTAC TCGTCGAAAC AATGCAACTA

951  TTGGGTAATG AATATCCGGT GCTTGTCAAG ATTACTCTCG ACGAAGGTCA
      AACCCATTAC TTATAGGCCA CGAACAGTTC TAATGAGAGC TGCTTCCAGT

1001  GCCAGCGTAT GCGCCTGGTC TGTACACCGT GCATCTGTCC TCGTTCAAAG
      CGGTCGCATA CGCGGACCAG ACATGTGGCA CGTAGACAGG AGCAAGTTTC

1051  TTGGTCAGTT CGGTTCTCTT ATGATTGACC GTCTGCGCCT CGTTCCGGCT
      AACCAGTCAA GCCAAGAGAA TACTAACTGG CAGACGCGGA GCAAGGCCGA

1101  AAGTAACATG GAGCAGGTCG CGGATTTCGA CACAATTTAT CAGGCGATGA
      TTCATTGTAC CTCGTCCAGC GCCTAAAGCT GTGTTAAATA GTCCGCTACT

1151  TACAAATCTC CGTTGTACTT TGTTTCGCGC TTGGTATAAT CGCTGGGGGT
      ATGTTTAGAG GCAACATGAA ACAAAGCGCG AACCATATTA GCGACCCCCA

1201  CAAAGATGAG TGTTTAGTG TATTCTTTCG CCTCTTTCGT TTTAGGTTGG
      GTTTCTACTC ACAAAATCAC ATAAGAAAGC GGAGAAAGCA AAATCCAACC

1251  TGCCTTCGTA GTGGCATTAC GTATTTACC CGTTTAATGG AAACTTCCTC
      ACGGAAGCAT CACCGTAATG CATAAAATGG GCAAATTACC TTTGAAGGAG

1301  ATGCGTAAGT CTTTAGTCCT CAAAGCCTCC GTAGCCGTTG CTACCCTCGT
      TACGCATTCA GAAATCAGGA GTTTCGGAGG CATCGGCAAC GATGGGAGCA

1351  TCCGATGCTG TCTTTCGCTG CTGAGGGTGA CGATCCCGCA AAAGCGGCCT
      AGGCTACGAC AGAAAGCGAC GACTCCCACT GCTAGGGCGT TTTCGCCGGA

1401  TTGACTCCCT GCAAGCCTCA GCGACCGAAT ATATCGGTTA TGCGTGGGCG
      AACTGAGGGA CGTTCGGAGT CGCTGGCTTA TATAGCCAAT ACGCACCCGC

1451  ATGGTTGTTG TCATTGTCGG CGCAACTATC GGTATCAAGC TGTTTAAGAA
      TACCAACAAC AGTAACAGCC GCGTTGATAG CCATAGTTCG ACAAATTCTT

1501  ATTCACCTCG AAAGCAAGCT GATAAAGGAG GTTTCTCGAT CGAGACGTTN
      TAAGTGGAGC TTTCGTTCGA CTATTTCCTC CAAAGAGCTA GCTCTGCAAN

1551  NNNGAGGTTC CAACTTTCAC CATAATGAAA TAAGATCACT ACCGGGCGTA
      NNNCTCCAAG GTTGAAAGTG GTATTACTTT ATTCTAGTGA TGGCCCGCAT

1601  TTTTTTGAGT TATCGAGATT TTCAGGAGCT AAGGAAGCTA AAATGGAGAA
      AAAAAACTCA ATAGCTCTAA AAGTCCTCGA TTCCTTCGAT TTTACCTCTT

1651  AAAAATCACT GGATATACCA CCGTTGATAT ATCCCAATGG CATCGTAAAG
      TTTTTAGTGA CCTATATGGT GGCAACTATA TAGGGTTACC GTAGCATTTC
```

Figure 2D

```
1701  AACATTTTGA GGCATTTCAG TCAGTTGCTC AATGTACCTA TAACCAGACC
      TTGTAAAACT CCGTAAAGTC AGTCAACGAG TTACATGGAT ATTGGTCTGG

1751  GTTCAGCTGG ATATTACGGC CTTTTTAAAG ACCGTAAAGA AAAATAAGCA
      CAAGTCGACC TATAATGCCG GAAAAATTTC TGGCATTTCT TTTTATTCGT

1801  CAAGTTTTAT CCGGCCTTTA TTCACATTCT TGCCCGCCTG ATGAATGCTC
      GTTCAAAATA GGCCGGAAAT AAGTGTAAGA ACGGGCGGAC TACTTACGAG

1851  ATCCGGAGTT CCGTATGGCA ATGAAAGACG GTGAGCTGGT GATATGGGAT
      TAGGCCTCAA GGCATACCGT TACTTTCTGC CACTCGACCA CTATACCCTA

1901  AGTGTTCACC CTTGTTACAC CGTTTTCCAT GAGCAAACTG AAACGTTTTC
      TCACAAGTGG GAACAATGTG GCAAAAGGTA CTCGTTTGAC TTTGCAAAAG

1951  ATCGCTCTGG AGTGAATACC ACGACGATTT CCGGCAGTTT CTACACATAT
      TAGCGAGACC TCACTTATGG TGCTGCTAAA GGCCGTCAAA GATGTGTATA

2001  ATTCGCAAGA TGTGGCGTGT TACGGTGAAA ACCTGGCCTA TTTCCCTAAA
      TAAGCGTTCT ACACCGCACA ATGCCACTTT TGGACCGGAT AAAGGGATTT

2051  GGGTTTATTG AGAATATGTT TTTCGTCTCA GCCAATCCCT GGGTGAGTTT
      CCCAAATAAC TCTTATACAA AAAGCAGAGT CGGTTAGGGA CCCACTCAAA

2101  CACCAGTTTT GATTTAAACG TGGCCAATAT GGACAACTTC TTCGCCCCCG
      GTGGTCAAAA CTAAATTTGC ACCGGTTATA CCTGTTGAAG AAGCGGGGGC

NcoI
                 --------
2151  TTTTCACCAT GGGCAAATAT TATACGCAAG GCGACAAGGT GCTGATGCCG
      AAAAGTGGTA CCCGTTTATA ATATGCGTTC CGCTGTTCCA CGACTACGGC

2201  CTGGCGATTC AGGTTCATCA TGCCGTCTGT GATGGCTTCC ATGTCGGCAG
      GACCGCTAAG TCCAAGTAGT ACGGCAGACA CTACCGAAGG TACAGCCGTC

2251  AATGCTTAAT GAATTACAAC AGTACTGCGA TGAGTGGCAG GGCGGGGCGT
      TTACGAATTA CTTAATGTTG TCATGACGCT ACTCACCGTC CCGCCCCGCA

2301  AATTTTTTTA AGGCAGTTAT TGGTGCCCTT AAACGCCTGG TGCTACGCCT
      TTAAAAAAAT TCCGTCAATA ACCACGGGAA TTTGCGGACC ACGATGCGGA

2351  GAATAAGTGA TAATAAGCGG ATGAATGGCA GAAATTCGAA AGCAAATTCG
      CTTATTCACT ATTATTCGCC TACTTACCGT CTTTAAGCTT TCGTTTAAGC

2401  ACCCGGTCGT CGGTTCAGGG CAGGGTCGTT AAATAGCCGC TTATGTCTAT
      TGGGCCAGCA GCCAAGTCCC GTCCCAGCAA TTTATCGGCG AATACAGATA

2451  TGCTGGTTTA CCGGTTTATT GACTACCGGA AGCAGTGTGA CCGTGTGCTT
      ACGACCAAAT GGCCAAATAA CTGATGGCCT TCGTCACACT GGCACACGAA

2501  CTCAAATGCC TGAGGCCAGT TTGCTCAGGC TCTCCCCGTG GAGGTAATAA
      GAGTTTACGG ACTCCGGTCA AACGAGTCCG AGAGGGGCAC CTCCATTATT
```

Figure 2E

```
2551  TTGCTCGACC GATAAAAGCG GCTTCCTGAC AGGAGGCCGT TTTGTTTTGC
      AACGAGCTGG CTATTTTCGC CGAAGGACTG TCCTCCGGCA AAACAAAACG

2601  AGCCCACCTC AACGCAATTA ATGTGAGTTA GCTCACTCAT TAGGCACCCC
      TCGGGTGGAG TTGCGTTAAT TACACTCAAT CGAGTGAGTA ATCCGTGGGG

2651  AGGCTTTACA CTTTATGCTT CCGGCTCGTA TGTTGTGTGG AATTGTGAGC
      TCCGAAATGT GAAATACGAA GGCCGAGCAT ACAACACACC TTAACACTCG

2701  GGATAACAAT TTCACACAGG AAACAGCTAT GACCATGATT ACGAATTTCT
      CCTATTGTTA AAGTGTGTCC TTTGTCGATA CTGGTACTAA TGCTTAAAGA

2751  AGATAACGAG GGCAAATCAT GAAAAGACA GCTATCGCGA TTGCAGTGGC
      TCTATTGCTC CCGTTTAGTA CTTTTTCTGT CGATAGCGCT AACGTCACCG

2801  ACTGGCTGGT TTCGCTACCG TAGCGCAGGC CGACTACAAA GATATCGTTA
      TGACCGACCA AAGCGATGGC ATCGCGTCCG GCTGATGTTT CTATAGCAAT

2851  TGACCCAGTC ACCGTCCTCC CTGACCGTTA CCGCTGGTGA AAAAGTTACC
      ACTGGGTCAG TGGCAGGAGG GACTGGCAAT GGCGACCACT TTTTCAATGG

2901  ATGTCCTGCA CCTCCTCCCA GTCCTGTTC AACTCCGGTA AACAGAAAAA
      TACAGGACGT GGAGGAGGGT CAGGGACAAG TTGAGGCCAT TTGTCTTTTT

2951  CTACCTGACC TGGTATCAGC AGAAACCGGG TCAGCCACCG AAAGTTCTGA
      GATGGACTGG ACCATAGTCG TCTTTGGCCC AGTCGGTGGC TTTCAAGACT

3001  TCTACTGGGC TTCCACCCGT GAATCCGGTG TTCCAGACCG TTTCACCGGT
      AGATGACCCG AAGGTGGGCA CTTAGGCCAC AAGGTCTGGC AAAGTGGCCA

3051  TCCGGTTCCG GCACCGACTT CACCCTGACC ATCTCCTCCG TTCAGGCTGA
      AGGCCAAGGC CGTGGCTGAA GTGGGACTGG TAGAGGAGGC AAGTCCGACT

3101  AGACCTGGCT GTTTACTACT GCCAGAACGA CTACTCCAAC CCACTGACCT
      TCTGGACCGA CAAATGATGA CGGTCTTGCT GATGAGGTTG GGTGACTGGA

3151  TCGGTGGTGG CACCAAACTG GAACTTAAGC GCGCTGGTGG TGGAGGGTCT
      AGCCACCACC GTGGTTTGAC CTTGAATTCG CGCGACCACC ACCTCCCAGA

BamHI
                                      ------
3201  GGAGGAGGTG GGAGTGGGGG AGGTGGATCC GGCGGGGAG GTTCAGGGGG
      CCTCCTCCAC CCTCACCCCC TCCACCTAGG CCGCCCCTC CAAGTCCCCC

3251  TGGCGGTAGT GGAGGGGGCG GTTCAGAAGT TCAACTAGTT GAATCCGGTG
      ACCGCCATCA CCTCCCCCGC CAAGTCTTCA AGTTGATCAA CTTAGGCCAC

3301  GTGACCTGGT TAAACCGGGT GGTTCCCTGA AACTGTCCTG CGCTGCTTCC
      CACTGGACCA ATTTGGCCCA CCAAGGGACT TTGACAGGAC GCGACGAAGG
```

Figure 2F

```
3351  GGTTTCTCCT TCTCCTCCTA CGGTATGTCC TGGGTTCGTC AGACCCCGGA
      CCAAAGAGGA AGAGGAGGAT GCCATACAGG ACCCAAGCAG TCTGGGGCCT

3401  CAAACGTCTG GAATGGGTTG CTACCATCTC AACGGTGGT GGTTACACCT
      GTTTGCAGAC CTTACCCAAC GATGGTAGAG GTTGCCACCA CCAATGTGGA

3451  ACTACCCGGA CTCCGTTAAA GGTCGTTTCA CCATCTCCCG TGACAACGCT
      TGATGGGCCT GAGGCAATTT CCAGCAAAGT GGTAGAGGGC ACTGTTGCGA

PstI
                             -------
3501  AAAAACACCC TGTACCTGCA GATGTCCTCC CTGAAATCCG AAGACTCAGC
      TTTTTGTGGG ACATGGACGT CTACAGGAGG GACTTTAGGC TTCTGAGTCG

3551  TATGTACTAC TGCGCTCGTC GTGAACGTTA CGACGAAAAC GGTTTCGCTT
      ATACATGATG ACGCGAGCAG CACTTGCAAT GCTGCTTTTG CCAAAGCGAA

EcoRI
                                                   ------
3601  ACTGGGGTCA GGGTACCCTG GTTACCGTTT CAGCTTCCGG AGAATTCGAG
      TGACCCCAGT CCCATGGGAC CAATGGCAAA GTCGAAGGCC TCTTAAGCTC

AvaI
        ------
3651  GCCTCGGGGG CCGAGGGCGG CGGTTCTGGT TCCGGTGATT TTGATTATGA
      CGGAGCCCCC GGCTCCCGCC GCCAAGACCA AGGCCACTAA AACTAATACT

3701  AAAAATGGCA AACGCTAATA AGGGGGCTAT GACCGAAAAT GCCGATGAAA
      TTTTTACCGT TTGCGATTAT TCCCCCGATA CTGGCTTTTA CGGCTACTTT

3751  ACGCGCTACA GTCTGACGCT AAAGGCAAAC TTGATTCTGT CGCTACTGAT
      TGCGCGATGT CAGACTGCGA TTTCCGTTTG AACTAAGACA GCGATGACTA

ClaI
             ------
3801  TACGGTGCTG CTATCGATGG TTTCATTGGT GACGTTTCCG GCCTTGCTAA
      ATGCCACGAC GATAGCTACC AAAGTAACCA CTGCAAAGGC CGGAACGATT

3851  TGGTAATGGT GCTACTGGTG ATTTGCTGG CTCTAATTCC CAAATGGCTC
      ACCATTACCA CGATGACCAC TAAAACGACC GAGATTAAGG GTTTACCGAG

3901  AAGTCGGTGA CGGTGATAAT TCACCTTTAA TGAATAATTT CCGTCAATAT
      TTCAGCCACT GCCACTATTA AGTGGAAATT ACTTATTAAA GGCAGTTATA

3951  TTACCTTCCC TCCCTCAATC GGTTGAATGT CGCCCTTTTG TCTTTGGCGC
      AATGGAAGGG AGGGAGTTAG CCAACTTACA GCGGGAAAAC AGAAACCGCG

4001  TGGTAAACCA TATGAATTTT CTATTGATTG TGACAAAATA AACTTATTCC
      ACCATTTGGT ATACTTAAAA GATAACTAAC ACTGTTTTAT TTGAATAAGG

4051  GTGGTGTCTT TGCGTTTCTT TTATATGTTG CCACCTTTAT GTATGTATTT
      CACCACAGAA ACGCAAAGAA AATATACAAC GGTGGAAATA CATACATAAA
```

Figure 2G

```
                                                          HindIII
                                                          ------
4101  TCTACGTTTG CTAACATACT GCGTAATAAG GAGTCTTGAT AAGCTTCGAG
      AGATGCAAAC GATTGTATGA CGCATTATTC CTCAGAACTA TTCGAAGCTC 4151  AAATTCACCT CGAAAGCAAG CTGATAAACC GATACAATTA AAGGCTCCTT
      TTTAAGTGGA GCTTTCGTTC GACTATTTGG CTATGTTAAT TTCCGAGGAA EcoRI
                           ------
4201  TTGGAGCCTT TTTTTTTGGA GAATTCAATC ATGCCAGTTC TTTTGGGTAT
      AACCTCGGAA AAAAAAACCT CTTAAGTTAG TACGGTCAAG AAAACCCATA 4251  TCCGTTATTA TTGCGTTTCC TCGGTTTCCT TCTGGTAACT TTGTTCGGCT
      AGGCAATAAT AACGCAAAGG AGCCAAAGGA AGACCATTGA AACAAGCCGA 4301  ATCTGCTTAC TTTCCTTAAA AAGGGCTTCG GTAAGATAGC TATTGCTATT
      TAGACGAATG AAAGGAATTT TTCCCGAAGC CATTCTATCG ATAACGATAA 4351  TCATTGTTTC TTGCTCTTAT TATTGGGCTT AACTCAATTC TTGTGGGTTA
      AGTAACAAAG AACGAGAATA ATAACCCGAA TTGAGTTAAG AACACCCAAT 4401  TCTCTCTGAT ATTAGCGCAC AATTACCCTC TGATTTTGTT CAGGGCGTTC
      AGAGAGACTA TAATCGCGTG TTAATGGGAG ACTAAAACAA GTCCCGCAAG 4451  AGTTAATTCT CCCGTCTAAT GCGCTTCCCT GTTTTATGT  TATTCTCTCT
      TCAATTAAGA GGGCAGATTA CGCGAAGGGA CAAAAATACA ATAAGAGAGA 4501  GTAAAGGCTG CTATTTTCAT TTTTGACGTT AAACAAAAAA TCGTTTCTTA
      CATTTCCGAC GATAAAAGTA AAAACTGCAA TTTGTTTTTT AGCAAAGAAT 4551  TTTGGATTGG GATAAATAAA TATGGCTGTT TATTTGTAA  CTGGCAAATT
      AAACCTAACC CTATTTATTT ATACCGACAA ATAAACATT  GACCGTTTAA 4601  AGGCTCTGGA AAGACGCTCG TTAGCGTTGG TAAGATTCAG GATAAAATTG
      TCCGAGACCT TTCTGCGAGC AATCGCAACC ATTCTAAGTC CTATTTTAAC 4651  TAGCTGGGTG CAAAATAGCA ACTAATCTTG ATTTAAGGCT TCAAAACCTC
      ATCGACCCAC GTTTTATCGT TGATTAGAAC TAAATTCCGA AGTTTTGGAG 4701  CCGCAAGTCG GGAGGTTCGC TAAAACGCCT CGCGTTCTTA GAATACCGGA
      GGCGTTCAGC CCTCCAAGCG ATTTTGCGGA GCGCAAGAAT CTTATGGCCT 4751  TAAGCCTTCT ATTTCTGATT TGCTTGCTAT TGGTCGTGGT AATGATTCCT
      ATTCGGAAGA TAAAGACTAA ACGAACGATA ACCAGCACCA TTACTAAGGA 4801  ACGACGAAAA TAAAAACGGT TTGCTTGTTC TTGATGAATG CGGTACTTGG
      TGCTGCTTTT ATTTTTGCCA AACGAACAAG AACTACTTAC GCCATGAACC 4851  TTTAATACCC GTTCATGGAA TGACAAGGAA AGACAGCCGA TTATTGATTG
      AAATTATGGG CAAGTACCTT ACTGTTCCTT TCTGTCGGCT AATAACTAAC
```

Figure 2H

```
4901  GTTTCTTCAT GCTCGTAAAT TGGGATGGGA TATTATTTTT CTTGTTCAGG
      CAAAGAAGTA CGAGCATTTA ACCCTACCCT ATAATAAAAA GAACAAGTCC

4951  ATTTATCTAT TGTTGATAAA CAGGCGCGTT CTGCATTAGC TGAACACGTT
      TAAATAGATA ACAACTATTT GTCCGCGCAA GACGTAATCG ACTTGTGCAA

5001  GTTTATTGTC GCCGTCTGGA CAGAATTACT TTACCCTTTG TCGGCACTTT
      CAAATAACAG CGGCAGACCT GTCTTAATGA AATGGGAAAC AGCCGTGAAA

5051  ATATTCTCTT GTTACTGGCT CAAAAATGCC TCTGCCTAAA TTACATGTTG
      TATAAGAGAA CAATGACCGA GTTTTACGG  AGACGGATTT AATGTACAAC

5101  GTGTTGTTAA ATATGGTGAT TCTCAATTAA GCCCTACTGT TGAGCGTTGG
      CACAACAATT TATACCACTA AGAGTTAATT CGGGATGACA ACTCGCAACC

5151  CTTTATACTG GTAAGAATTT ATATAACGCA TATGACACTA AACAGGCTTT
      GAAATATGAC CATTCTTAAA TATATTGCGT ATACTGTGAT TTGTCCGAAA

5201  TTCCAGTAAT TATGATTCAG GTGTTTATTC ATATTTAACC CCTTATTTAT
      AAGGTCATTA ATACTAAGTC CACAAATAAG TATAAATTGG GGAATAAATA

5251  CACACGGTCG GTATTTCAAA CCATTAAATT TAGGTCAGAA GATGAAATTA
      GTGTGCCAGC CATAAAGTTT GGTAATTTAA ATCCAGTCTT CTACTTTAAT

5301  ACTAAAATAT ATTTGAAAAA GTTTTCTCGC GTTCTTTGTC TTGCGATAGG
      TGATTTTATA TAAACTTTTT CAAAAGAGCG CAAGAAACAG AACGCTATCC

5351  ATTTGCATCA GCATTTACAT ATAGTTATAT AACCCAACCT AAGCCGGAGG
      TAAACGTAGT CGTAAATGTA TATCAATATA TTGGGTTGGA TTCGGCCTCC

5401  TTAAAAAGGT AGTCTCTCAG ACCTATGATT TTGATAAATT CACTATTGAC
      AATTTTTCCA TCAGAGAGTC TGGATACTAA AACTATTTAA GTGATAACTG

5451  TCTTCTCAGC GTCTTAATCT AAGCTATCGC TATGTTTTCA AGGATTCTAA
      AGAAGAGTCG CAGAATTAGA TTCGATAGCG ATACAAAAGT TCCTAAGATT

5501  GGGAAAATTA ATTAATAGCG ACGATTTACA GAAGCAAGGT TATTCCATCA
      CCCTTTTAAT TAATTATCGC TGCTAAATGT CTTCGTTCCA ATAAGGTAGT

5551  CATATATTGA TTTATGTACT GTTTCAATTA AAAAAGGTAA TTCAAATGAA
      GTATATAACT AAATACATGA CAAAGTTAAT TTTTTCCATT AAGTTTACTT

5601  ATTGTTAAAT GTAATTAATT TTGTTTTCTT GATGTTTGTT TCATCATCTT
      TAACAATTTA CATTAATTAA AACAAAAGAA CTACAAACAA AGTAGTAGAA

5651  CTTTTGCTCA AGTAATTGAA ATGAATAATT CGCCTCTGCG CGATTTCGTG
      GAAAACGAGT TCATTAACTT TACTTATTAA GCGGAGACGC GCTAAAGCAC

5701  ACTTGGTATT CAAAGCAAAC AGGTGAATCT GTTATTGTCT CACCTGATGT
      TGAACCATAA GTTTCGTTTG TCCACTTAGA CAATAACAGA GTGGACTACA
```

Figure 2I

```
5751  TAAAGGTACA GTGACTGTAT ATTCCTCTGA CGTTAAGCCT GAAAATTTAC
      ATTTCCATGT CACTGACATA TAAGGAGACT GCAATTCGGA CTTTTAAATG

5801  GCAATTTCTT TATCTCTGTT TTACGTGCTA ATAATTTTGA TATGGTTGGC
      CGTTAAAGAA ATAGAGACAA AATGCACGAT TATTAAAACT ATACCAACCG

5851  TCAATTCCTT CCATAATTCA GAAATATAAC CCAAATAGTC AGGATTATAT
      AGTTAAGGAA GGTATTAAGT CTTTATATTG GGTTTATCAG TCCTAATATA

5901  TGATGAATTG CCATCATCTG ATATTCAGGA ATATGATGAT AATTCCGCTC
      ACTACTTAAC GGTAGTAGAC TATAAGTCCT TATACTACTA TTAAGGCGAG

5951  CTTCTGGTGG TTTCTTTGTT CCGCAAAATG ATAATGTTAC TCAAACATTT
      GAAGACCACC AAAGAAACAA GGCGTTTTAC TATTACAATG AGTTTGTAAA

6001  AAAATTAATA ACGTTCGCGC AAAGGATTTA ATAAGGGTTG TAGAATTGTT
      TTTTAATTAT TGCAAGCGCG TTTCCTAAAT TATTCCCAAC ATCTTAACAA

6051  TGTTAAATCT AATACATCTA AATCCTCAAA TGTATTATCT GTTGATGGTT
      ACAATTTAGA TTATGTAGAT TTAGGAGTTT ACATAATAGA CAACTACCAA

6101  CTAACTTATT AGTAGTTAGC GCCCCTAAAG ATATTTTAGA TAACCTTCCG
      GATTGAATAA TCATCAATCG CGGGGATTTC TATAAAATCT ATTGGAAGGC

6151  CAATTTCTTT CTACTGTTGA TTTGCCAACT GACCAGATAT TGATTGAAGG
      GTTAAAGAAA GATGACAACT AAACGGTTGA CTGGTCTATA ACTAACTTCC

6201  ATTAATTTTC GAGGTTCAGC AAGGTGATGC TTTAGATTTT TCCTTTGCTG
      TAATTAAAAG CTCCAAGTCG TTCCACTACG AAATCTAAAA AGGAAACGAC

6251  CTGGCTCTCA GCGCGGCACT GTTGCTGGTG GTGTTAATAC TGACCGTCTA
      GACCGAGAGT CGCGCCGTGA CAACGACCAC CACAATTATG ACTGGCAGAT

6301  ACCTCTGTTT TATCTTCTGC GGGTGGTTCG TTCGGTATTT TTAACGGCGA
      TGGAGACAAA ATAGAAGACG CCCACCAAGC AAGCCATAAA AATTGCCGCT

6351  TGTTTTAGGG CTATCAGTTC GCGCATTAAA GACTAATAGC CATTCAAAAA
      ACAAAATCCC GATAGTCAAG CGCGTAATTT CTGATTATCG GTAAGTTTTT

6401  TATTGTCTGT GCCTCGTATT CTTACGCTTT CAGGTCAGAA GGGTTCTATT
      ATAACAGACA CGGAGCATAA GAATGCGAAA GTCCAGTCTT CCCAAGATAA

6451  TCTGTTGGCC AGAATGTCCC TTTTATTACT GGTCGTGTAA CTGGTGAATC
      AGACAACCGG TCTTACAGGG AAAATAATGA CCAGCACATT GACCACTTAG

6501  TGCCAATGTA AATAATCCAT TTCAGACGGT TGAGCGTCAA AATGTTGGTA
      ACGGTTACAT TTATTAGGTA AAGTCTGCCA ACTCGCAGTT TTACAACCAT

6551  TTTCTATGAG TGTTTTTCCC GTTGCAATGG CTGGCGGTAA TATTGTTTTA
      AAAGATACTC ACAAAAGGG CAACGTTACC GACCGCCATT ATAACAAAAT
```

Figure 2J

```
6601  GATATAACCA GTAAGGCCGA TAGTTTGAGT TCTTCTACTC AGGCAAGTGA
      CTATATTGGT CATTCCGGCT ATCAAACTCA AGAAGATGAG TCCGTTCACT

6651  TGTTATTACT AATCAAAGAA GTATTGCGAC AACGGTTAAT TTGCGTGATG
      ACAATAATGA TTAGTTTCTT CATAACGCTG TTGCCAATTA AACGCACTAC

6701  GTCAGACTCT TTTGCTCGGT GGCCTCACTG ATTACAAAAA CACTTCTCAA
      CAGTCTGAGA AAACGAGCCA CCGGAGTGAC TAATGTTTTT GTGAAGAGTT

6751  GATTCTGGTG TGCCGTTCCT GTCTAAAATC CCTTTAATCG GCCTCCTGTT
      CTAAGACCAC ACGGCAAGGA CAGATTTTAG GGAAATTAGC CGGAGGACAA

6801  TAGCTCCCGT TCTGATTCTA ACGAGGAAAG CACGTTGTAC GTGCTCGTCA
      ATCGAGGGCA AGACTAAGAT TGCTCCTTTC GTGCAACATG CACGAGCAGT

6851  AAGCAACCAT AGTACGCGCC CTGTAGCGGC GCATTAAGCG CGGCGGGTGT
      TTCGTTGGTA TCATGCGCGG GACATCGCCG CGTAATTCGC GCCGCCCACA

6901  GGTGGTTACG CGCAGCGTGA CCGCTACACT TGCCAGCGCC CTAGCGCCCG
      CCACCAATGC GCGTCGCACT GGCGATGTGA ACGGTCGCGG GATCGCGGGC

6951  CTCCTTTCGC TTTCTTCCCT TCCTTTCTCG CCACGTTCTC CGGCTTTCCC
      GAGGAAAGCG AAAGAAGGGA AGGAAAGAGC GGTGCAAGAG GCCGAAAGGG

BamHI
                                    -------
7001  CGTCAAGCTC TAAATCGGGG GATCCCTTTA GGGTTCCGAT TTAGTGCTTT
      GCAGTTCGAG ATTTAGCCCC CTAGGGAAAT CCCAAGGCTA AATCACGAAA

7051  ACGGCACCTC GACCTCCAAA AACTTGATTT GGGTGATGGT TCACGTAGTG
      TGCCGTGGAG CTGGAGGTTT TTGAACTAAA CCCACTACCA AGTGCATCAC

7101  GGCCATCGCC CTGATAGACG GTTTTTCGCC CTTTGACGTT GGAGTCCACG
      CCGGTAGCGG GACTATCTGC CAAAAAGCGG GAAACTGCAA CCTCAGGTGC

7151  TTCTTTAATA GTGGACTCTT GTTCCAAACT GGAACAACAC TCACAACTAA
      AAGAAATTAT CACCTGAGAA CAAGGTTTGA CCTTGTTGTG AGTGTTGATT

7201  CTCGGCCTAT TCTTTTGATT TATAAGGATT TTTGTCATTT TCTGCTTACT
      GAGCCGGATA AGAAAACTAA ATATTCCTAA AAACAGTAAA AGACGAATGA

7251  GGTTAAAAAA TAAGCTGATT TAACAAATAT TTAACGCGAA ATTTAACAAA
      CCAATTTTTT ATTCGACTAA ATTGTTTATA AATTGCGCTT TAAATTGTTT

7301  ACATTAACGT TTACAATTTA AATATTTGCT TATACAATCA TCCTGTTTTT
      TGTAATTGCA AATGTTAAAT TTATAAACGA ATATGTTAGT AGGACAAAAA

7351  GGGGCTTTTC TGATTATCAA CCGGGGTACA TATGATTGAC ATGCTAGTTT
      CCCCGAAAAG ACTAATAGTT GGCCCCATGT ATACTAACTG TACGATCAAA
```

Figure 2K

```
                       ClaI
                      ------
7401  TACGATTACC GTTCATCGAT TCTCTTGTTT GCTCCAGACT TTCAGGTAAT
      ATGCTAATGG CAAGTAGCTA AGAGAACAAA CGAGGTCTGA AAGTCCATTA

7451  GACCTGATAG CCTTTGTAGA CCTCTCAAAA ATAGCTACCC TCTCCGGCAT
      CTGGACTATC GGAAACATCT GGAGAGTTTT TATCGATGGG AGAGGCCGTA

7501  GAATTTATCA GCTAGAACGG TTGAATATCA TATTGACGGT GATTTGACTG
      CTTAAATAGT CGATCTTGCC AACTTATAGT ATAACTGCCA CTAAACTGAC

7551  TCTCCGGCCT TTCTCACCCG TTTGAATCTT TGCCTACTCA TTACTCCGGC
      AGAGGCCGGA AAGAGTGGGC AAACTTAGAA ACGGATGAGT AATGAGGCCG

7601  ATTGCATTTA AAATATATGA GGGTTCTAAA AATTTTTATC CCTGCGTTGA
      TAACGTAAAT TTTATATACT CCCAAGATTT TTAAAAATAG GGACGCAACT

7651  AATTAAGGCT TCACCAGCAA AAGTATTACA GGGTCATAAT GTTTTTGGTA
      TTAATTCCGA AGTGGTCGTT TTCATAATGT CCCAGTATTA CAAAAACCAT

7701  CAACCGATTT AGCTTTATGC TCTGAGGCTT TATTGCTTAA TTTTGCTAAC
      GTTGGCTAAA TCGAAATACG AGACTCCGAA ATAACGAATT AAAACGATTG

7751  TCTCTGCCTT GCTTGTACGA TTTATTGGAT GTT
      AGAGACGGAA CGAACATGCT AAATAACCTA CAA
```

Figure 3B

```
  1   AACGCTACTA CCATTAGTAG AATTGATGCC ACCTTTTCAG CTCGCGCCCC
      TTGCGATGAT GGTAATCATC TTAACTACGG TGGAAAAGTC GAGCGCGGGG

51   AAATGAAAAT ATAGCTAAAC AGGTTATTGA CCATTTGCGA AATGTATCTA
      TTTACTTTTA TATCGATTTG TCCAATAACT GGTAAACGCT TTACATAGAT

101   ATGGTCAAAC TAAATCTACT CGTTCGCAGA ATTGGGAATC AACTGTTACA
      TACCAGTTTG ATTTAGATGA GCAAGCGTCT TAACCCTTAG TTGACAATGT

151   TGGAATGAAA CTTCCAGACA CCGTACTTTA GTTGCATATT TAAAACATGT
      ACCTTACTTT GAAGGTCTGT GGCATGAAAT CAACGTATAA ATTTTGTACA

201   TGAACTACAG CACCAGATTC AGCAATTAAG CTCTAAGCCA TCCGCAAAAA
      ACTTGATGTC GTGGTCTAAG TCGTTAATTC GAGATTCGGT AGGCGTTTTT

251   TGACCTCTTA TCAAAAGGAG CAATTAAAGG TACTGTCTAA TCCTGACCTG
      ACTGGAGAAT AGTTTTCCTC GTTAATTTCC ATGACAGATT AGGACTGGAC

301   TTGGAATTTG CTTCCGGTCT GGTTCGCTTT GAGGCTCGAA TTGAAACGCG
      AACCTTAAAC GAAGGCCAGA CCAAGCGAAA CTCCGAGCTT AACTTTGCGC

351   ATATTTGAAG TCTTTCGGGC TTCCTCTTAA TCTTTTTGAT GCAATTCGCT
      TATAAACTTC AGAAAGCCCG AAGGAGAATT AGAAAAACTA CGTTAAGCGA

401   TTGCTTCTGA CTATAATAGA CAGGGTAAAG ACCTGATTTT TGATTTATGG
      AACGAAGACT GATATTATCT GTCCCATTTC TGGACTAAAA ACTAAATACC

451   TCATTCTCGT TTTCTGAACT GTTTAAAGCA TTTGAGGGGG ATTCAATGAA
      AGTAAGAGCA AAAGACTTGA CAAATTTCGT AAACTCCCCC TAAGTTACTT

501   TATTTATGAC GATTCCGCAG TATTGGACGC TATCCAGTCT AAACATTTTA
      ATAAATACTG CTAAGGCGTC ATAACCTGCG ATAGGTCAGA TTTGTAAAAT

551   CAATTACCCC CTCTGGCAAA ACTTCCTTTG CAAAAGCCTC TCGCTATTTT
      GTTAATGGGG GAGACCGTTT TGAAGGAAAC GTTTTCGGAG AGCGATAAAA

601   GGTTTCTATC GTCGTCTGGT TAATGAGGGT TATGATAGTG TTGCTCTTAC
      CCAAAGATAG CAGCAGACCA ATTACTCCCA ATACTATCAC AACGAGAATG

651   CATGCCTCGT AATTCCTTTT GGCGTTATGT ATCTGCATTA GTTGAGTGTG
      GTACGGAGCA TTAAGGAAAA CCGCAATACA TAGACGTAAT CAACTCACAC

701   GTATTCCTAA ATCTCAATTG ATGAATCTTT CCACCTGTAA TAATGTTGTT
      CATAAGGATT TAGAGTTAAC TACTTAGAAA GGTGGACATT ATTACAACAA

751   CCGTTAGTTC GTTTTATTAA CGTAGATTTT TCCTCCCAAC GTCCTGACTG
      GGCAATCAAG CAAAATAATT GCATCTAAAA AGGAGGGTTG CAGGACTGAC

801   GTATAATGAG CCAGTTCTTA AAATCGCATA AGGTAATTCA AAATGATTAA
      CATATTACTC GGTCAAGAAT TTTAGCGTAT TCCATTAAGT TTTACTAATT
```

Figure 3C

```
 851  AGTTGAAATT AAACCGTCTC AAGCGCAATT TACTACCCGT TCTGGTGTTT
      TCAACTTTAA TTTGGCAGAG TTCGCGTTAA ATGATGGGCA AGACCACAAA

901  CTCGTCAGGG CAAGCCTTAT TCACTGAATG AGCAGCTTTG TTACGTTGAT
      GAGCAGTCCC GTTCGGAATA AGTGACTTAC TCGTCGAAAC AATGCAACTA

951  TTGGGTAATG AATATCCGGT GCTTGTCAAG ATTACTCTCG ACGAAGGTCA
      AACCCATTAC TTATAGGCCA CGAACAGTTC TAATGAGAGC TGCTTCCAGT

1001  GCCAGCGTAT GCGCCTGGTC TGTACACCGT GCATCTGTCC TCGTTCAAAG
      CGGTCGCATA CGCGGACCAG ACATGTGGCA CGTAGACAGG AGCAAGTTTC

1051  TTGGTCAGTT CGGTTCTCTT ATGATTGACC GTCTGCGCCT CGTTCCGGCT
      AACCAGTCAA GCCAAGAGAA TACTAACTGG CAGACGCGGA GCAAGGCCGA

1101  AAGTAACATG GAGCAGGTCG CGGATTTCGA CACAATTTAT CAGGCGATGA
      TTCATTGTAC CTCGTCCAGC GCCTAAAGCT GTGTTAAATA GTCCGCTACT

1151  TACAAATCTC CGTTGTACTT TGTTTCGCGC TTGGTATAAT CGCTGGGGGT
      ATGTTTAGAG GCAACATGAA ACAAAGCGCG AACCATATTA GCGACCCCCA

1201  CAAAGATGAG TGTTTTAGTG TATTCTTTCG CCTCTTTCGT TTTAGGTTGG
      GTTTCTACTC ACAAAATCAC ATAAGAAAGC GGAGAAAGCA AAATCCAACC

1251  TGCCTTCGTA GTGGCATTAC GTATTTTACC CGTTTAATGG AAACTTCCTC
      ACGGAAGCAT CACCGTAATG CATAAAATGG GCAAATTACC TTTGAAGGAG

1301  ATGCGTAAGT CTTTAGTCCT CAAAGCCTCC GTAGCCGTTG CTACCCTCGT
      TACGCATTCA GAAATCAGGA GTTTCGGAGG CATCGGCAAC GATGGGAGCA

1351  TCCGATGCTG TCTTTCGCTG CTGAGGGTGA CGATCCCGCA AAAGCGGCCT
      AGGCTACGAC AGAAAGCGAC GACTCCCACT GCTAGGGCGT TTTCGCCGGA

1401  TTGACTCCCT GCAAGCCTCA GCGACCGAAT ATATCGGTTA TGCGTGGGCG
      AACTGAGGGA CGTTCGGAGT CGCTGGCTTA TATAGCCAAT ACGCACCCGC

1451  ATGGTTGTTG TCATTGTCGG CGCAACTATC GGTATCAAGC TGTTTAAGAA
      TACCAACAAC AGTAACAGCC GCGTTGATAG CCATAGTTCG ACAAATTCTT

1501  ATTCACCTCG AAAGCAAGCT GATAAAGGAG GTTTCTCGAT CGAGACGTTN
      TAAGTGGAGC TTTCGTTCGA CTATTTCCTC CAAAGAGCTA GCTCTGCAAN

1551  NNNGAGGTTC CAACTTTCAC CATAATGAAA TAAGATCACT ACCGGGCGTA
      NNNCTCCAAG GTTGAAAGTG GTATTACTTT ATTCTAGTGA TGGCCCGCAT

1601  TTTTTTGAGT TATCGAGATT TTCAGGAGCT AAGGAAGCTA AAATGGAGAA
      AAAAAACTCA ATAGCTCTAA AAGTCCTCGA TTCCTTCGAT TTTACCTCTT

1651  AAAAATCACT GGATATACCA CCGTTGATAT ATCCCAATGG CATCGTAAAG
      TTTTTAGTGA CCTATATGGT GGCAACTATA TAGGGTTACC GTAGCATTTC
```

Figure 3D

```
1701  AACATTTTGA GGCATTTCAG TCAGTTGCTC AATGTACCTA TAACCAGACC
      TTGTAAAACT CCGTAAAGTC AGTCAACGAG TTACATGGAT ATTGGTCTGG

1751  GTTCAGCTGG ATATTACGGC CTTTTTAAAG ACCGTAAAGA AAAATAAGCA
      CAAGTCGACC TATAATGCCG GAAAAATTTC TGGCATTTCT TTTTATTCGT

1801  CAAGTTTTAT CCGGCCTTTA TTCACATTCT TGCCCGCCTG ATGAATGCTC
      GTTCAAAATA GGCCGGAAAT AAGTGTAAGA ACGGGCGGAC TACTTACGAG

1851  ATCCGGAGTT CCGTATGGCA ATGAAAGACG GTGAGCTGGT GATATGGGAT
      TAGGCCTCAA GGCATACCGT TACTTTCTGC CACTCGACCA CTATACCCTA

1901  AGTGTTCACC CTTGTTACAC CGTTTTCCAT GAGCAAACTG AAACGTTTTC
      TCACAAGTGG GAACAATGTG GCAAAAGGTA CTCGTTTGAC TTTGCAAAAG

1951  ATCGCTCTGG AGTGAATACC ACGACGATTT CCGGCAGTTT CTACACATAT
      TAGCGAGACC TCACTTATGG TGCTGCTAAA GGCCGTCAAA GATGTGTATA

2001  ATTCGCAAGA TGTGGCGTGT TACGGTGAAA ACCTGGCCTA TTTCCCTAAA
      TAAGCGTTCT ACACCGCACA ATGCCACTTT TGGACCGGAT AAAGGGATTT

2051  GGGTTTATTG AGAATATGTT TTTCGTCTCA GCCAATCCCT GGGTGAGTTT
      CCCAAATAAC TCTTATACAA AAAGCAGAGT CGGTTAGGGA CCCACTCAAA

2101  CACCAGTTTT GATTTAAACG TAGCCAATAT GGACAACTTC TTCGCCCCCG
      GTGGTCAAAA CTAAATTTGC ATCGGTTATA CCTGTTGAAG AAGCGGGGGC

2151  TTTTCACTAT GGGCAAATAT TATACGCAAG GCGACAAGGT GCTGATGCCG
      AAAAGTGATA CCCGTTTATA ATATGCGTTC CGCTGTTCCA CGACTACGGC

2201  CTGGCGATTC AGGTTCATCA TGCCGTTTGT GATGGCTTCC ATGTCGGCAG
      GACCGCTAAG TCCAAGTAGT ACGGCAAACA CTACCGAAGG TACAGCCGTC

2251  AATGCTTAAT GAATTACAAC AGTACTGCGA TGAGTGGCAG GGCGGGGCGT
      TTACGAATTA CTTAATGTTG TCATGACGCT ACTCACCGTC CCGCCCCGCA

2301  AATTTTTTTA AGGCAGTTAT TGGTGCCCTT AAACGCCTGG TGCTAGCCTG
      TTAAAAAAAT TCCGTCAATA ACCACGGGAA TTTGCGGACC ACGATCGGAC

2351  AGGCCAGTTT GCTCAGGCTC TCCCCGTGGA GGTAATAATT GCTCGACCGA
      TCCGGTCAAA CGAGTCCGAG AGGGGCACCT CCATTATTAA CGAGCTGGCT

2401  TAAAAGCGGC TTCCTGACAG GAGGCCGTTT TGTTTTGCAG CCCACCTCAA
      ATTTTCGCCG AAGGACTGTC CTCCGGCAAA ACAAAACGTC GGGTGGAGTT

2451  CGCAATTAAT GTGAGTTAGC TCACTCATTA GGCACCCCAG GCTTTACACT
      GCGTTAATTA CACTCAATCG AGTGAGTAAT CCGTGGGGTC CGAAATGTGA

2501  TTATGCTTCC GGCTCGTATG TTGTGTGGAA TTGTGAGCGG ATAACAATTT
      AATACGAAGG CCGAGCATAC AACACACCTT AACACTCGCC TATTGTTAAA
```

Figure 3E

```
2551  CACACAGGAA ACAGCTATGA CCATGATTAC GAATTTCTAG ATAACGAGGG
      GTGTGTCCTT TGTCGATACT GGTACTAATG CTTAAAGATC TATTGCTCCC

2601  CAAAAAATGA AAAAGACAGC TATCGCGATT GCAGTGGCAC TGGCTGGTTT
      GTTTTTTACT TTTTCTGTCG ATAGCGCTAA CGTCACCGTG ACCGACCAAA

2651  CGCTACCGTA GCGCAGGCCG ACTACAAAGA TGTCGACGCC GGTGGTCGGA
      GCGATGGCAT CGCGTCCGGC TGATGTTTCT ACAGCTGCGG CCACCAGCCT

2701  TCGCCCGGCT AGAGGAAAAA GTGAAAACCT GAAAGCGCA AAACTCCGAG
      AGCGGGCCGA TCTCCTTTTT CACTTTTGGA ACTTTCGCGT TTTGAGGCTC

2751  CTGGCGTCCA CGGCCAACAT GCTCAGGGAA CAGGTGGCAC AGCTTAAACA
      GACCGCAGGT GCCGGTTGTA CGAGTCCCTT GTCCACCGTG TCGAATTTGT

EcoRI
                                        -------
2801  GAAAGTCATG AACCACGGTG GTGCCGAATT CAATGCTGGC GGCGGCTCTG
      CTTTCAGTAC TTGGTGCCAC CACGGCTTAA GTTACGACCG CCGCCGAGAC

2851  GTGGTGGTTC TGGTGGCGGC TCTGAGGGTG GTGGCTCTGA GGGTGGCGGT
      CACCACCAAG ACCACCGCCG AGACTCCCAC CACCGAGACT CCCACCGCCA

2901  TCTGAGGGTG GCGGCTCTGA GGGAGGCGGT TCCGGTGGTG GCTCTGGTTC
      AGACTCCCAC CGCCGAGACT CCCTCCGCCA AGGCCACCAC CGAGACCAAG

2951  CGGTGATTTT GATTATGAAA AGATGGCAAA CGCTAATAAG GGGGCTATGA
      GCCACTAAAA CTAATACTTT TCTACCGTTT GCGATTATTC CCCCGATACT

3001  CCGAAAATGC CGATGAAAAC GCGCTACAGT CTGACGCTAA AGGCAAACTT
      GGCTTTTACG GCTACTTTTG CGCGATGTCA GACTGCGATT TCCGTTTGAA

ClaI
                                        -------
3051  GATTCTGTCG CTACTGATTA CGGTGCTGCT ATCGATGGTT TCATTGGTGA
      CTAAGACAGC GATGACTAAT GCCACGACGA TAGCTACCAA AGTAACCACT

3101  CGTTTCCGGC CTTGCTAATG GTAATGGTGC TACTGGTGAT TTTGCTGGCT
      GCAAAGGCCG GAACGATTAC CATTACCACG ATGACCACTA AAACGACCGA

3151  CTAATTCCCA AATGGCTCAA GTCGGTGACG GTGATAATTC ACCTTTAATG
      GATTAAGGGT TTACCGAGTT CAGCCACTGC CACTATTAAG TGGAAATTAC

3201  AATAATTTCC GTCAATATTT ACCTTCCCTC CCTCAATCGG TTGAATGTCG
      TTATTAAAGG CAGTTATAAA TGGAAGGGAG GGAGTTAGCC AACTTACAGC

3251  CCCTTTTGTC TTTAGCGCTG GTAAACCATA TGAATTTTCT ATTGATTGTG
      GGGAAAACAG AAATCGCGAC CATTTGGTAT ACTTAAAAGA TAACTAACAC

3301  ACAAAATAAA CTTATTCCGT GGTGTCTTTG CGTTTCTTTT ATATGTTGCC
      TGTTTTATTT GAATAAGGCA CCACAGAAAC GCAAAGAAAA TATACAACGG
```

Figure 3F

```
3351  ACCTTTATGT ATGTATTTTC TACGTTTGCT AACATACTGC GTAATAAGGA
      TGGAAATACA TACATAAAAG ATGCAAACGA TTGTATGACG CATTATTCCT

HindIII
                 -------
3401  GTCTTGATAA GCTTCGAGAA ATTCACCTCG AAAGCAAGCT GATAAACCGA
      CAGAACTATT CGAAGCTCTT TAAGTGGAGC TTTCGTTCGA CTATTTGGCT 3451  TACAATTAAA GGCTCCTTTT GGAGCCTTTT TTTTGGAGA  ATTAATTCAA
      ATGTTAATTT CCGAGGAAAA CCTCGGAAAA AAAAACCTCT TAATTAAGTT 3501  TCATGCCAGT TCTTTGGGT  ATTCCGTTAT TATTGCGTTT CCTCGGTTTC
      AGTACGGTCA AGAAAACCCA TAAGGCAATA ATAACGCAAA GGAGCCAAAG 3551  CTTCTGGTAA CTTTGTTCGG CTATCTGCTT ACTTTCCTTA AAAAGGGCTT
      GAAGACCATT GAAACAAGCC GATAGACGAA TGAAAGGAAT TTTTCCCGAA 3601  CGGTAAGATA GCTATTGCTA TTTCATTGTT TCTTGCTCTT ATTATTGGGC
      GCCATTCTAT CGATAACGAT AAAGTAACAA AGAACGAGAA TAATAACCCG 3651  TTAACTCAAT TCTTGTGGGT TATCTCTCTG ATATTAGCGC ACAATTACCC
      AATTGAGTTA AGAACACCCA ATAGAGAGAC TATAATCGCG TGTTAATGGG 3701  TCTGATTTTG TTCAGGGCGT TCAGTTAATT CTCCCGTCTA ATGCGCTTCC
      AGACTAAAAC AAGTCCCGCA AGTCAATTAA GAGGGCAGAT TACGCGAAGG 3751  CTGTTTTTAT GTTATTCTCT CTGTAAAGGC TGCTATTTC  ATTTTGACG
      GACAAAAATA CAATAAGAGA GACATTTCCG ACGATAAAAG TAAAAACTGC 3801  TTAAACAAAA AATCGTTTCT TATTTGGATT GGGATAAATA AATATGGCTG
      AATTTGTTTT TTAGCAAAGA ATAAACCTAA CCCTATTTAT TTATACCGAC 3851  TTTATTTTGT AACTGGCAAA TTAGGCTCTG GAAAGACGCT CGTTAGCGTT
      AAATAAAACA TTGACCGTTT AATCCGAGAC CTTTCTGCGA GCAATCGCAA 3901  GGTAAGATTC AGGATAAAAT TGTAGCTGGG TGCAAAATAG CAACTAATCT
      CCATTCTAAG TCCTATTTTA ACATCGACCC ACGTTTATC  GTTGATTAGA 3951  TGATTTAAGG CTTCAAAACC TCCCGCAAGT CGGGAGGTTC GCTAAAACGC
      ACTAAATTCC GAAGTTTTGG AGGGCGTTCA GCCCTCCAAG CGATTTTGCG 4001  CTCGCGTTCT TAGAATACCG GATAAGCCTT CTATTTCTGA TTTGCTTGCT
      GAGCGCAAGA ATCTTATGGC CTATTCGGAA GATAAAGACT AAACGAACGA 4051  ATTGGTCGTG GTAATGATTC CTACGACGAA AATAAAAACG GTTTGCTTGT
      TAACCAGCAC CATTACTAAG GATGCTGCTT TTATTTTTGC CAAACGAACA 4101  TCTTGATGAA TGCGGTACTT GGTTTAATAC CCGTTCATGG AATGACAAGG
      AGAACTACTT ACGCCATGAA CCAAATTATG GGCAAGTACC TTACTGTTCC
```

Figure 3G

```
4151  AAAGACAGCC GATTATTGAT TGGTTTCTTC ATGCTCGTAA ATTGGGATGG
      TTTCTGTCGG CTAATAACTA ACCAAAGAAG TACGAGCATT TAACCCTACC

4201  GATATTATTT TTCTTGTTCA GGATTTATCT ATTGTTGATA AACAGGCGCG
      CTATAATAAA AAGAACAAGT CCTAAATAGA TAACAACTAT TTGTCCGCGC

4251  TTCTGCATTA GCTGAACACG TTGTTTATTG TCGCCGTCTG GACAGAATTA
      AAGACGTAAT CGACTTGTGC AACAAATAAC AGCGGCAGAC CTGTCTTAAT

4301  CTTTACCCTT TGTCGGCACT TTATATTCTC TTGTTACTGG CTCAAAAATG
      GAAATGGGAA ACAGCCGTGA AATATAAGAG AACAATGACC GAGTTTTTAC

4351  CCTCTGCCTA AATTACATGT TGGTGTTGTT AAATATGGTG ATTCTCAATT
      GGAGACGGAT TTAATGTACA ACCACAACAA TTTATACCAC TAAGAGTTAA

4401  AAGCCCTACT GTTGAGCGTT GGCTTTATAC TGGTAAGAAT TTATATAACG
      TTCGGGATGA CAACTCGCAA CCGAAATATG ACCATTCTTA AATATATTGC

4451  CATATGACAC TAAACAGGCT TTTTCCAGTA ATTATGATTC AGGTGTTTAT
      GTATACTGTG ATTTGTCCGA AAAAGGTCAT TAATACTAAG TCCACAAATA

4501  TCATATTTAA CCCCTTATTT ATCACACGGT CGGTATTTCA AACCATTAAA
      AGTATAAATT GGGGAATAAA TAGTGTGCCA GCCATAAAGT TTGGTAATTT

4551  TTTAGGTCAG AAGATGAAAT TAACTAAAAT ATATTTGAAA AAGTTTTCTC
      AAATCCAGTC TTCTACTTTA ATTGATTTTA TATAAACTTT TTCAAAAGAG

4601  GCGTTCTTTG TCTTGCGATA GGATTTGCAT CAGCATTTAC ATATAGTTAT
      CGCAAGAAAC AGAACGCTAT CCTAAACGTA GTCGTAAATG TATATCAATA

4651  ATAACCCAAC CTAAGCCGGA GGTTAAAAAG GTAGTCTCTC AGACCTATGA
      TATTGGGTTG GATTCGGCCT CCAATTTTTC CATCAGAGAG TCTGGATACT

4701  TTTTGATAAA TTCACTATTG ACTCTTCTCA GCGTCTTAAT CTAAGCTATC
      AAAACTATTT AAGTGATAAC TGAGAAGAGT CGCAGAATTA GATTCGATAG

4751  GCTATGTTTT CAAGGATTCT AAGGGAAAAT TAATTAATAG CGACGATTTA
      CGATACAAAA GTTCCTAAGA TTCCCTTTTA ATTAATTATC GCTGCTAAAT

4801  CAGAAGCAAG GTTATTCCAT CACATATATT GATTTATGTA CTGTTTCAAT
      GTCTTCGTTC CAATAAGGTA GTGTATATAA CTAAATACAT GACAAAGTTA

4851  TAAAAAAGGT AATTCAAATG AAATTGTTAA ATGTAATTAA TTTTGTTTTC
      ATTTTTTCCA TTAAGTTTAC TTTAACAATT TACATTAATT AAAACAAAAG

4901  TTGATGTTTG TTTCATCATC TTCTTTTGCT CAAGTAATTG AAATGAATAA
      AACTACAAAC AAAGTAGTAG AAGAAAACGA GTTCATTAAC TTTACTTATT

4951  TTCGCCTCTG CGCGATTTCG TGACTTGGTA TTCAAAGCAA ACAGGTGAAT
      AAGCGGAGAC GCGCTAAAGC ACTGAACCAT AAGTTTCGTT TGTCCACTTA
```

Figure 3H

```
5001  CTGTTATTGT CTCACCTGAT GTTAAAGGTA CAGTGACTGT ATATTCCTCT
      GACAATAACA GAGTGGACTA CAATTTCCAT GTCACTGACA TATAAGGAGA

5051  GACGTTAAGC CTGAAAATTT ACGCAATTTC TTTATCTCTG TTTTACGTGC
      CTGCAATTCG GACTTTTAAA TGCGTTAAAG AAATAGAGAC AAAATGCACG

5101  TAATAATTTT GATATGGTTG GCTCAATTCC TTCCATAATT CAGAAATATA
      ATTATTAAAA CTATACCAAC CGAGTTAAGG AAGGTATTAA GTCTTTATAT

5151  ACCCAAATAG TCAGGATTAT ATTGATGAAT TGCCATCATC TGATATTCAG
      TGGGTTTATC AGTCCTAATA TAACTACTTA ACGGTAGTAG ACTATAAGTC

5201  GAATATGATG ATAATTCCGC TCCTTCTGGT GGTTTCTTTG TTCCGCAAAA
      CTTATACTAC TATTAAGGCG AGGAAGACCA CCAAAGAAAC AAGGCGTTTT

5251  TGATAATGTT ACTCAAACAT TTAAAATTAA TAACGTTCGC GCAAAGGATT
      ACTATTACAA TGAGTTTGTA AATTTTAATT ATTGCAAGCG CGTTTCCTAA

5301  TAATAAGGGT TGTAGAATTG TTTGTTAAAT CTAATACATC TAAATCCTCA
      ATTATTCCCA ACATCTTAAC AAACAATTTA GATTATGTAG ATTTAGGAGT

5351  AATGTATTAT CTGTTGATGG TTCTAACTTA TTAGTAGTTA GCGCCCCTAA
      TTACATAATA GACAACTACC AAGATTGAAT AATCATCAAT CGCGGGGATT

5401  AGATATTTTA GATAACCTTC CGCAATTTCT TTCTACTGTT GATTTGCCAA
      TCTATAAAAT CTATTGGAAG GCGTTAAAGA AAGATGACAA CTAAACGGTT

5451  CTGACCAGAT ATTGATTGAA GGATTAATTT TCGAGGTTCA GCAAGGTGAT
      GACTGGTCTA TAACTAACTT CCTAATTAAA AGCTCCAAGT CGTTCCACTA

5501  GCTTTAGATT TTTCCTTTGC TGCTGGCTCT CAGCGCGGCA CTGTTGCTGG
      CGAAATCTAA AAAGGAAACG ACGACCGAGA GTCGCGCCGT GACAACGACC

5551  TGGTGTTAAT ACTGACCGTC TAACCTCTGT TTTATCTTCT GCGGGTGGTT
      ACCACAATTA TGACTGGCAG ATTGGAGACA AAATAGAAGA CGCCCACCAA

5601  CGTTCGGTAT TTTTAACGGC GATGTTTTAG GGCTATCAGT TCGCGCATTA
      GCAAGCCATA AAAATTGCCG CTACAAAATC CCGATAGTCA AGCGCGTAAT

5651  AAGACTAATA GCCATTCAAA AATATTGTCT GTGCCTCGTA TTCTTACGCT
      TTCTGATTAT CGGTAAGTTT TTATAACAGA CACGGAGCAT AAGAATGCGA

5701  TTCAGGTCAG AAGGGTTCTA TTTCTGTTGG CCAGAATGTC CCTTTTATTA
      AAGTCCAGTC TTCCCAAGAT AAAGACAACC GGTCTTACAG GGAAAATAAT

5751  CTGGTCGTGT AACTGGTGAA TCTGCCAATG TAAATAATCC ATTTCAGACG
      GACCAGCACA TTGACCACTT AGACGGTTAC ATTTATTAGG TAAAGTCTGC

5801  GTTGAGCGTC AAAATGTTGG TATTTCTATG AGTGTTTTTC CCGTTGCAAT
      CAACTCGCAG TTTTACAACC ATAAAGATAC TCACAAAAAG GGCAACGTTA
```

Figure 3I

```
5851  GGCTGGCGGT AATATTGTTT TAGATATAAC CAGTAAGGCC GATAGTTTGA
      CCGACCGCCA TTATAACAAA ATCTATATTG GTCATTCCGG CTATCAAACT

5901  GTTCTTCTAC TCAGGCAAGT GATGTTATTA CTAATCAAAG AAGTATTGCG
      CAAGAAGATG AGTCCGTTCA CTACAATAAT GATTAGTTTC TTCATAACGC

5951  ACAACGGTTA ATTTGCGTGA TGGTCAGACT CTTTTGCTCG GTGGCCTCAC
      TGTTGCCAAT TAAACGCACT ACCAGTCTGA GAAAACGAGC CACCGGAGTG

6001  TGATTACAAA AACACTTCTC AAGATTCTGG TGTGCCGTTC CTGTCTAAAA
      ACTAATGTTT TTGTGAAGAG TTCTAAGACC ACACGGCAAG GACAGATTTT

6051  TCCCTTTAAT CGGCCTCCTG TTTAGCTCCC GTTCTGATTC TAACGAGGAA
      AGGGAAATTA GCCGGAGGAC AAATCGAGGG CAAGACTAAG ATTGCTCCTT

6101  AGCACGTTGT ACGTGCTCGT CAAAGCAACC ATAGTACGCG CCCTGTAGCG
      TCGTGCAACA TGCACGAGCA GTTTCGTTGG TATCATGCGC GGGACATCGC

6151  GCGCATTAAG CGCGGCGGGT GTGGTGGTTA CGCGCAGCGT GACCGCTACA
      CGCGTAATTC GCGCCGCCCA CACCACCAAT GCGCGTCGCA CTGGCGATGT

6201  CTTGCCAGCG CCCTAGCGCC CGCTCCTTTC GCTTTCTTCC CTTCCTTTCT
      GAACGGTCGC GGGATCGCGG GCGAGGAAAG CGAAAGAAGG GAAGGAAAGA

BamHI
                                                    ------
6251  CGCCACGTTC TCCGGCTTTC CCCGTCAAGC TCTAAATCGG GGGATCCCTT
      GCGGTGCAAG AGGCCGAAAG GGGCAGTTCG AGATTTAGCC CCCTAGGGAA

6301  TAGGGTTCCG ATTTAGTGCT TTACGGCACC TCGACCTCCA AAAACTTGAT
      ATCCCAAGGC TAAATCACGA AATGCCGTGG AGCTGGAGGT TTTTGAACTA

6351  TTGGGTGATG GTTCACGTAG TGGGCCATCG CCCTGATAGA CGGTTTTTCG
      AACCCACTAC CAAGTGCATC ACCCGGTAGC GGGACTATCT GCCAAAAAGC

6401  CCCTTTGACG TTGGAGTCCA CGTTCTTTAA TAGTGGACTC TTGTTCCAAA
      GGGAAACTGC AACCTCAGGT GCAAGAAATT ATCACCTGAG AACAAGGTTT

6451  CTGGAACAAC ACTCACAACT AACTCGGCCT ATTCTTTTGA TTTATAAGGA
      GACCTTGTTG TGAGTGTTGA TTGAGCCGGA TAAGAAAACT AAATATTCCT

6501  TTTTTGTCAT TTTCTGCTTA CTGGTTAAAA AATAAGCTGA TTTAACAAAT
      AAAAACAGTA AAAGACGAAT GACCAATTTT TTATTCGACT AAATTGTTTA

6551  ATTTAACGCG AAATTTAACA AAACATTAAC GTTTACAATT TAAATATTTG
      TAAATTGCGC TTTAAATTGT TTTGTAATTG CAAATGTTAA ATTTATAAAC

6601  CTTATACAAT CATCCTGTTT TTGGGGCTTT TCTGATTATC AACCGGGGTA
      GAATATGTTA GTAGGACAAA AACCCCGAAA AGACTAATAG TTGGCCCCAT
```

Figure 3J

```
                                              ClaI
                                            -------
6651   CATATGATTG ACATGCTAGT TTTACGATTA CCGTTCATCG ATTCTCTTGT
       GTATACTAAC TGTACGATCA AAATGCTAAT GGCAAGTAGC TAAGAGAACA

6701   TTGCTCCAGA CTTTCAGGTA ATGACCTGAT AGCCTTTGTA GACCTCTCAA
       AACGAGGTCT GAAAGTCCAT TACTGGACTA TCGGAAACAT CTGGAGAGTT

6751   AAATAGCTAC CCTCTCCGGC ATGAATTTAT CAGCTAGAAC GGTTGAATAT
       TTTATCGATG GGAGAGGCCG TACTTAAATA GTCGATCTTG CCAACTTATA

6801   CATATTGACG GTGATTTGAC TGTCTCCGGC CTTTCTCACC CGTTTGAATC
       GTATAACTGC CACTAAACTG ACAGAGGCCG GAAAGAGTGG GCAAACTTAG

6851   TTTGCCTACT CATTACTCCG GCATTGCATT TAAAATATAT GAGGGTTCTA
       AAACGGATGA GTAATGAGGC CGTAACGTAA ATTTTATATA CTCCCAAGAT

6901   AAAATTTTTA TCCCTGCGTT GAAATTAAGG CTTCACCAGC AAAAGTATTA
       TTTTAAAAAT AGGGACGCAA CTTTAATTCC GAAGTGGTCG TTTTCATAAT

6951   CAGGGTCATA ATGTTTTTGG TACAACCGAT TTAGCTTTAT GCTCTGAGGC
       GTCCCAGTAT TACAAAAACC ATGTTGGCTA AATCGAAATA CGAGACTCCG

7001   TTTATTGCTT AATTTTGCTA ACTCTCTGCC TTGCTTGTAC GATTTATTGG
       AAATAACGAA TTAAAACGAT TGAGAGACGG AACGAACATG CTAAATAACC

7051   ATGTT
       TACAA
```

Figure 4A:
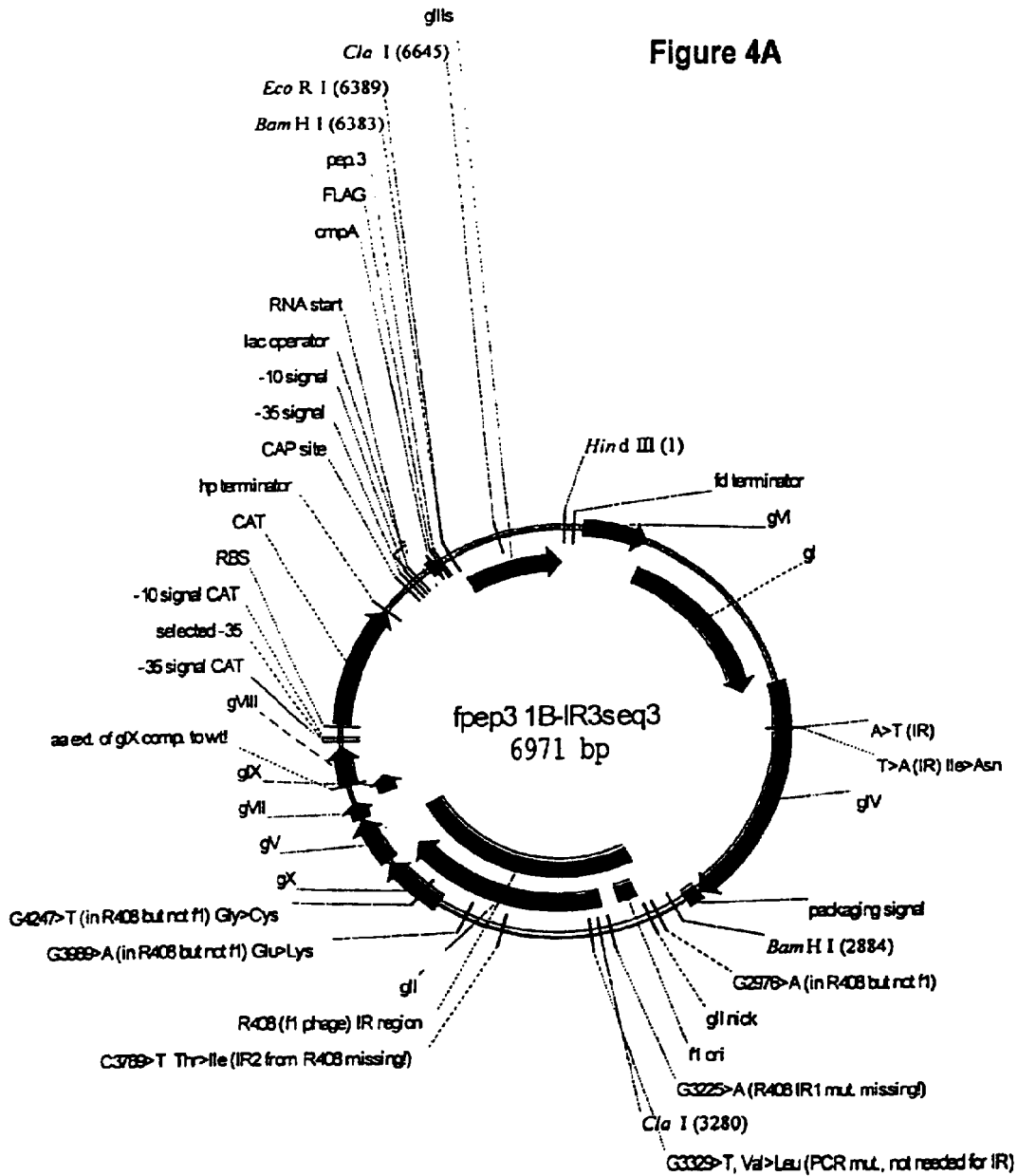

Figure 4B    HindIII
             -----

1  AGCTTCGAGA AATTCACCTC GAAAGCAAGC TGATAAACCG ATACAATTAA
        TCGAAGCTCT TTAAGTGGAG CTTTCGTTCG ACTATTTGGC TATGTTAATT

51  AGGCTCCTTT TGGAGCCTTT TTTTTGGAG AATTAATTCA ATCATGCCAG
        TCCGAGGAAA ACCTCGGAAA AAAAAACCTC TTAATTAAGT TAGTACGGTC

101  TTCTTTTGGG TATTCCGTTA TTATTGCGTT CCTCGGTTT CCTTCTGGTA
        AAGAAAACCC ATAAGGCAAT AATAACGCAA AGGAGCCAAA GGAAGACCAT

151  ACTTTGTTCG GCTATCTGCT TACTTTCCTT AAAAAGGGCT TCGGTAAGAT
        TGAAACAAGC CGATAGACGA ATGAAAGGAA TTTTTCCCGA AGCCATTCTA

201  AGCTATTGCT ATTTCATTGT TTCTTGCTCT TATTATTGGG CTTAACTCAA
        TCGATAACGA TAAAGTAACA AAGAACGAGA ATAATAACCC GAATTGAGTT

251  TTCTTGTGGG TTATCTCTCT GATATTAGCG CACAATTACC CTCTGATTTT
        AAGAACACCC AATAGAGAGA CTATAATCGC GTGTTAATGG GAGACTAAAA

301  GTTCAGGGCG TTCAGTTAAT TCTCCCGTCT AATGCGCTTC CCTGTTTTTA
        CAAGTCCCGC AAGTCAATTA AGAGGGCAGA TTACGCGAAG GGACAAAAAT

351  TGTTATTCTC TCTGTAAAGG CTGCTATTTT CATTTTTGAC GTTAAACAAA
        ACAATAAGAG AGACATTTCC GACGATAAAA GTAAAAACTG CAATTTGTTT

401  AAATCGTTTC TTATTTGGAT TGGGATAAAT AAATATGGCT GTTTATTTTG
        TTTAGCAAAG AATAAACCTA ACCCTATTTA TTTATACCGA CAAATAAAAC

451  TAACTGGCAA ATTAGGCTCT GGAAAGACGC TCGTTAGCGT TGGTAAGATT
        ATTGACCGTT TAATCCGAGA CCTTTCTGCG AGCAATCGCA ACCATTCTAA

501  CAGGATAAAA TTGTAGCTGG GTGCAAAATA GCAACTAATC TTGATTTAAG
        GTCCTATTTT AACATCGACC CACGTTTTAT CGTTGATTAG AACTAAATTC

551  GCTTCAAAAC CTCCCGCAAG TCGGGAGGTT CGCTAAAACG CCTCGCGTTC
        CGAAGTTTTG GAGGGCGTTC AGCCCTCCAA GCGATTTTGC GGAGCGCAAG

601  TTAGAATACC GGATAAGCCT TCTATTTCTG ATTTGCTTGC TATTGGTCGT
        AATCTTATGG CCTATTCGGA AGATAAAGAC TAAACGAACG ATAACCAGCA

651  GGTAATGATT CCTACGACGA AAATAAAAAC GGTTTGCTTG TTCTTGATGA
        CCATTACTAA GGATGCTGCT TTTATTTTTG CCAAACGAAC AAGAACTACT

701  ATGCGGTACT TGGTTTAATA CCCGTTCATG GAATGACAAG GAAAGACAGC
        TACGCCATGA ACCAAATTAT GGGCAAGTAC CTTACTGTTC CTTTCTGTCG

751  CGATTATTGA TTGGTTTCTT CATGCTCGTA AATTGGGATG GGATATTATT
        GCTAATAACT AACCAAAGAA GTACGAGCAT TTAACCCTAC CCTATAATAA

Figure 4C

```
 801   TTTCTTGTTC AGGATTTATC TATTGTTGAT AAACAGGCGC GTTCTGCATT
       AAAGAACAAG TCCTAAATAG ATAACAACTA TTTGTCCGCG CAAGACGTAA

851   AGCTGAACAC GTTGTTTATT GTCGCCGTCT GGACAGAATT ACTTTACCCT
       TCGACTTGTG CAACAAATAA CAGCGGCAGA CCTGTCTTAA TGAAATGGGA

901   TTGTCGGCAC TTTATATTCT CTTGTTACTG GCTCAAAAAT GCCTCTGCCT
       AACAGCCGTG AAATATAAGA GAACAATGAC CGAGTTTTTA CGGAGACGGA

951   AAATTACATG TTGGTGTTGT TAAATATGGT GATTCTCAAT TAAGCCCTAC
       TTTAATGTAC AACCACAACA ATTTATACCA CTAAGAGTTA ATTCGGGATG

1001   TGTTGAGCGT TGGCTTTATA CTGGTAAGAA TTTATATAAC GCATATGACA
       ACAACTCGCA ACCGAAATAT GACCATTCTT AAATATATTG CGTATACTGT

1051   CTAAACAGGC TTTTTCCAGT AATTATGATT CAGGTGTTTA TTCATATTTA
       GATTTGTCCG AAAAAGGTCA TTAATACTAA GTCCACAAAT AAGTATAAAT

1101   ACCCCTTATT TATCACACGG TCGGTATTTC AAACCATTAA ATTTAGGTCA
       TGGGGAATAA ATAGTGTGCC AGCCATAAAG TTTGGTAATT TAAATCCAGT

1151   GAAGATGAAA TTAACTAAAA TATATTTGAA AAAGTTTTCT CGCGTTCTTT
       CTTCTACTTT AATTGATTTT ATATAAACTT TTTCAAAAGA GCGCAAGAAA

1201   GTCTTGCGAT AGGATTTGCA TCAGCATTTA CATATAGTTA TATAACCCAA
       CAGAACGCTA TCCTAAACGT AGTCGTAAAT GTATATCAAT ATATTGGGTT

1251   CCTAAGCCGG AGGTTAAAAA GGTAGTCTCT CAGACCTATG ATTTTGATAA
       GGATTCGGCC TCCAATTTTT CCATCAGAGA GTCTGGATAC TAAAACTATT

1301   ATTCACTATT GACTCTTCTC AGCGTCTTAA TCTAAGCTAT CGCTATGTTT
       TAAGTGATAA CTGAGAAGAG TCGCAGAATT AGATTCGATA GCGATACAAA

1351   TCAAGGATTC TAAGGGAAAA TTAATTAATA GCGACGATTT ACAGAAGCAA
       AGTTCCTAAG ATTCCCTTTT AATTAATTAT CGCTGCTAAA TGTCTTCGTT

1401   GGTTATTCCA TCACATATAT TGATTTATGT ACTGTTTCAA TTAAAAAAGG
       CCAATAAGGT AGTGTATATA ACTAAATACA TGACAAAGTT AATTTTTTCC

1451   TAATTCAAAT GAAATTGTTA AATGTAATTA ATTTGTTTT CTTGATGTTT
       ATTAAGTTTA CTTTAACAAT TTACATTAAT TAAAACAAAA GAACTACAAA

1501   GTTTCATCAT CTTCTTTTGC TCAAGTAATT GAAATGAATA ATTCGCCTCT
       CAAAGTAGTA GAAGAAAACG AGTTCATTAA CTTTACTTAT TAAGCGGAGA

1551   GCGCGATTTC GTGACTTGGT ATTCAAAGCA AACAGGTGAA TCTGTTATTG
       CGCGCTAAAG CACTGAACCA TAAGTTTCGT TTGTCCACTT AGACAATAAC

1601   TCTCACCTGA TGTTAAAGGT ACAGTGACTG TATATTCCTC TGACGTTAAG
       AGAGTGGACT ACAATTTCCA TGTCACTGAC ATATAAGGAG ACTGCAATTC
```

Figure 4D

```
1651  CCTGAAAATT TACGCAATTT CTTTATCTCT GTTTTACGTG CTAATAATTT
      GGACTTTTAA ATGCGTTAAA GAAATAGAGA CAAAATGCAC GATTATTAAA

1701  TGATATGGTT GGCTCTAATC CTTCCATAAT TCAGAAATAT AACCCAAATA
      ACTATACCAA CCGAGATTAG GAAGGTATTA AGTCTTTATA TTGGGTTTAT

1751  GTCAGGATTA TATTGATGAA TTGCCATCAT CTGATATTCA GGAATATGAT
      CAGTCCTAAT ATAACTACTT AACGGTAGTA GACTATAAGT CCTTATACTA

1801  GATAATTCCG CTCCTTCTGG TGGTTTCTTT GTTCCGCAAA ATGATAATGT
      CTATTAAGGC GAGGAAGACC ACCAAAGAAA CAAGGCGTTT TACTATTACA

1851  TACTCAAACA TTTAAAATTA ATAACGTTCG CGCAAAGGAT TTAATAAGGG
      ATGAGTTTGT AAATTTTAAT TATTGCAAGC GCGTTTCCTA AATTATTCCC

1901  TTGTAGAATT GTTTGTTAAA TCTAATACAT CTAAATCCTC AAATGTATTA
      AACATCTTAA CAAACAATTT AGATTATGTA GATTTAGGAG TTTACATAAT

1951  TCTGTTGATG GTTCTAACTT ATTAGTAGTT AGCGCCCCTA AAGATATTTT
      AGACAACTAC CAAGATTGAA TAATCATCAA TCGCGGGGAT TTCTATAAAA

2001  AGATAACCTT CCGCAATTTC TTTCTACTGT TGATTTGCCA ACTGACCAGA
      TCTATTGGAA GGCGTTAAAG AAAGATGACA ACTAAACGGT TGACTGGTCT

2051  TATTGATTGA AGGATTAATT TTCGAGGTTC AGCAAGGTGA TGCTTTAGAT
      ATAACTAACT TCCTAATTAA AAGCTCCAAG TCGTTCCACT ACGAAATCTA

2101  TTTTCCTTTG CTGCTGGCTC TCAGCGCGGC ACTGTTGCTG GTGGTGTTAA
      AAAAGGAAAC GACGACCGAG AGTCGCGCCG TGACAACGAC CACCACAATT

2151  TACTGACCGT CTAACCTCTG TTTTATCTTC TGCGGGTGGT TCGTTCGGTA
      ATGACTGGCA GATTGGAGAC AAAATAGAAG ACGCCCACCA AGCAAGCCAT

2201  TTTTTAACGG CGATGTTTTA GGGCTATCAG TTCGCGCATT AAAGACTAAT
      AAAAATTGCC GCTACAAAAT CCCGATAGTC AAGCGCGTAA TTTCTGATTA

2251  AGCCATTCAA AAATATTGTC TGTGCCTCGT ATTCTTACGC TTTCAGGTCA
      TCGGTAAGTT TTTATAACAG ACACGGAGCA TAAGAATGCG AAAGTCCAGT

2301  GAAGGGTTCT ATTTCTGTTG GCCAGAATGT CCCTTTTATT ACTGGTCGTG
      CTTCCCAAGA TAAAGACAAC CGGTCTTACA GGGAAAATAA TGACCAGCAC

2351  TAACTGGTGA ATCTGCCAAT GTAAATAATC CATTTCAGAC AATTGAGCGT
      ATTGACCACT TAGACGGTTA CATTTATTAG GTAAAGTCTG TTAACTCGCA

2401  CAAAATGTTG GTATTTCTAT GAGTGTTTTT CCCGTTGCAA TGGCTGGCGG
      GTTTTACAAC CATAAAGATA CTCACAAAAA GGGCAACGTT ACCGACCGCC

2451  TAATATTGTT TTAGATATAA CCAGTAAGGC CGATAGTTTG AGTTCTTCTA
      ATTATAACAA AATCTATATT GGTCATTCCG GCTATCAAAC TCAAGAAGAT
```

Figure 4E

```
2501  CTCAGGCAAG TGATGTTATT ACTAATCAAA GAAGTATTGC GACAACGGTT
      GAGTCCGTTC ACTACAATAA TGATTAGTTT CTTCATAACG CTGTTGCCAA

2551  AATTTGCGTG ATGGTCAGAC TCTTTTGCTC GGTGGCCTCA CTGATTACAA
      TTAAACGCAC TACCAGTCTG AGAAAACGAG CCACCGGAGT GACTAATGTT

2601  AAACACTTCT CAAGATTCTG GTGTGCCGTT CCTGTCTAAA ATCCCTTTAA
      TTTGTGAAGA GTTCTAAGAC CACACGGCAA GGACAGATTT TAGGGAAATT

2651  TCGGCCTCCT GTTTAGCTCC CGTTCTGATT CTAACGAGGA AAGCACGTTG
      AGCCGGAGGA CAAATCGAGG GCAAGACTAA GATTGCTCCT TTCGTGCAAC

2701  TACGTGCTCG TCAAAGCAAC CATAGTACGC GCCCTGTAGC GGCGCATTAA
      ATGCACGAGC AGTTTCGTTG GTATCATGCG CGGGACATCG CCGCGTAATT

2751  GCGCGGCGGG TGTGGTGGTT ACGCGCAGCG TGACCGCTAC ACTTGCCAGC
      CGCGCCGCCC ACACCACCAA TGCGCGTCGC ACTGGCGATG TGAACGGTCG

2801  GCCCTAGCGC CCGCTCCTTT CGCTTTCTTC CCTTCCTTTC TCGCCACGTT
      CGGGATCGCG GGCGAGGAAA GCGAAAGAAG GGAAGGAAAG AGCGGTGCAA

BamHI
                                          ------
2851  CTCCGGCTTT CCCCGTCAAG CTCTAAATCG GGGGATCCCT TTAGGGTTCC
      GAGGCCGAAA GGGGCAGTTC GAGATTTAGC CCCCTAGGGA AATCCCAAGG

2901  GATTTAGTGC TTTACGGCAC CTCGACCTCC AAAAACTTGA TTTGGGTGAT
      CTAAATCACG AAATGCCGTG GAGCTGGAGG TTTTTGAACT AAACCCACTA

2951  GGTTCACGTA GTGGGCCATC GCCCTAATAG ACGGTTTTC GCCCTTTGAC
      CCAAGTGCAT CACCCGGTAG CGGGATTATC TGCCAAAAAG CGGGAAACTG

3001  GTTGGAGTCC ACGTTCTTTA ATAGTGGACT CTTGTTCCAA ACTGGAACAA
      CAACCTCAGG TGCAAGAAAT TATCACCTGA GAACAAGGTT TGACCTTGTT

3051  CACTCAACCC TATCTCGGTC TATTCTTTTG ATTTATAAGG GATTTTGCCG
      GTGAGTTGGG ATAGAGCCAG ATAAGAAAAC TAAATATTCC CTAAAACGGC

3101  ATTTCGGCCT ATTGGTTAAA AAATGAGCTG ATTTAACAAA AATTTAACGC
      TAAAGCCGGA TAACCAATTT TTTACTCGAC TAAATTGTTT TTAAATTGCG

3151  GAATTTTAAC AAAATATTAA CGTTTACAAT TTAAATATTT GCTTATACAA
      CTTAAAATTG TTTTATAATT GCAAATGTTA AATTTATAAA CGAATATGTT

3201  TCTTCCTGTT TTTGGGGCTT TTCTGATTAT CAACCGGGGT ACATATGATT
      AGAAGGACAA AAACCCCGAA AAGACTAATA GTTGGCCCCA TGTATACTAA

ClaI
                                          -------
3251  GACATGCTAG TTTTACGATT ACCGTTCATC GATTCTCTTG TTTGCTCCAG
      CTGTACGATC AAAATGCTAA TGGCAAGTAG CTAAGAGAAC AAACGAGGTC
```

Figure 4F

```
3301  ACTCTCAGGC AATGACCTGA TAGCCTTTTT AGACCTCTCA AAAATAGCTA
      TGAGAGTCCG TTACTGGACT ATCGGAAAAA TCTGGAGAGT TTTTATCGAT

3351  CCCTCTCCGG CATGAATTTA TCAGCTAGAA CGGTTGAATA TCATATTGAT
      GGGAGAGGCC GTACTTAAAT AGTCGATCTT GCCAACTTAT AGTATAACTA

3401  GGTGATTTGA CTGTCTCCGG CCTTTCTCAC CCGTTTGAAT CTTTACCTAC
      CCACTAAACT GACAGAGGCC GGAAAGAGTG GGCAAACTTA GAAATGGATG

3451  ACATTACTCA GGCATTGCAT TTAAAATATA TGAGGGTTCT AAAAATTTTT
      TGTAATGAGT CCGTAACGTA AATTTTATAT ACTCCCAAGA TTTTTAAAAA

3501  ATCCTTGCGT TGAAATAAAG GCTTCTCCCG CAAAAGTATT ACAGGGTCAT
      TAGGAACGCA ACTTTATTTC CGAAGAGGGC GTTTTCATAA TGTCCCAGTA

3551  AATGTTTTTG GTACAACCGA TTTAGCTTTA TGCTCTGAGG CTTTATTGCT
      TTACAAAAAC CATGTTGGCT AAATCGAAAT ACGAGACTCC GAAATAACGA

3601  TAATTTTGCT AATTCTTTGC CTTGCCTGTA TGATTTATTG GATGTTAACG
      ATTAAAACGA TTAAGAAACG GAACGGACAT ACTAAATAAC CTACAATTGC

3651  CTACTACTAT TAGTAGAATT GATGCCACCT TTTCAGCTCG CGCCCCAAAT
      GATGATGATA ATCATCTTAA CTACGGTGGA AAAGTCGAGC GCGGGGTTTA

3701  GAAAATATAG CTAAACAGGT TATTGACCAT TTGCGAAATG TATCTAATGG
      CTTTTATATC GATTTGTCCA ATAACTGGTA AACGCTTTAC ATAGATTACC

3751  TCAAACTAAA TCTACTCGTT CGCAGAATTG GGAATCAACT GTTACATGGA
      AGTTTGATTT AGATGAGCAA GCGTCTTAAC CCTTAGTTGA CAATGTACCT

3801  ATGAAACTTC CAGACACCGT ACTTAGTTG CATATTTAAA ACATGTTGAG
      TACTTTGAAG GTCTGTGGCA TGAAATCAAC GTATAAATTT TGTACAACTC

3851  CTACAGCACC AGATCCAGCA ATTAAGCTCT AAGCCATCCG CAAAAATGAC
      GATGTCGTGG TCTAGGTCGT TAATTCGAGA TTCGGTAGGC GTTTTTACTG

3901  CTCTTATCAA AAGGAGCAAT TAAAGGTACT CTCTAATCCT GACCTGTTGG
      GAGAATAGTT TTCCTCGTTA ATTCCATGA GAGATTAGGA CTGGACAACC

3951  AGTTTGCTTC CGGTCTGGTT CGCTTTGAAG CTCGAATTAA AACGCGATAT
      TCAAACGAAG GCCAGACCAA GCGAAACTTC GAGCTTAATT TTGCGCTATA

4001  TTGAAGTCTT TCGGGCTTCC TCTTAATCTT TTTGATGCAA TCCGCTTTGC
      AACTTCAGAA AGCCCGAAGG AGAATTAGAA AAACTACGTT AGGCGAAACG

4051  TTCTGACTAT AATAGTCAGG GTAAAGACCT GATTTTTGAT TTATGGTCAT
      AAGACTGATA TTATCAGTCC CATTTCTGGA CTAAAAACTA AATACCAGTA

4101  TCTCGTTTTC TGAACTGTTT AAAGCATTTG AGGGGGATTC AATGAATATT
      AGAGCAAAAG ACTTGACAAA TTTCGTAAAC TCCCCCTAAG TTACTTATAA
```

Figure 4G

```
4151  TATGACGATT CCGCAGTATT GGACGCTATC CAGTCTAAAC ATTTTACTAT
      ATACTGCTAA GGCGTCATAA CCTGCGATAG GTCAGATTTG TAAAATGATA

4201  TACCCCCTCT GGCAAAACTT CTTTTGCAAA AGCCTCTCGC TATTTTTGTT
      ATGGGGGAGA CCGTTTTGAA GAAAACGTTT TCGGAGAGCG ATAAAAACAA

4251  TTTATCGTCG TCTGGTAAAC GAGGGTTATG ATAGTGTTGC TCTTACTATG
      AAATAGCAGC AGACCATTTG CTCCCAATAC TATCACAACG AGAATGATAC

4301  CCTCGTAATT CCTTTTGGCG TTATGTATCT GCATTAGTTG AATGTGGTAT
      GGAGCATTAA GGAAAACCGC AATACATAGA CGTAATCAAC TTACACCATA

4351  TCCTAAATCT CAACTGATGA ATCTTTCTAC CTGTAATAAT GTTGTTCCGT
      AGGATTTAGA GTTGACTACT TAGAAAGATG GACATTATTA CAACAAGGCA

4401  TAGTTCGTTT TATTAACGTA GATTTTTCTT CCCAACGTCC TGACTGGTAT
      ATCAAGCAAA ATAATTGCAT CTAAAAAGAA GGGTTGCAGG ACTGACCATA

4451  AATGAGCCAG TTCTTAAAAT CGCATAAGGT AATTCACAAT GATTAAAGTT
      TTACTCGGTC AAGAATTTTA GCGTATTCCA TTAAGTGTTA CTAATTTCAA

4501  GAAATTAAAC CATCTCAAGC GCAATTCACT ACCCGTTCTG GTGTTTCTCG
      CTTTAATTTG GTAGAGTTCG CGTTAAGTGA TGGGCAAGAC CACAAAGAGC

4551  TCAGGGCAAG CCTTATTCAC TGAATGAGCA GCTTTGTTAC GTTGATTTGG
      AGTCCCGTTC GGAATAAGTG ACTTACTCGT CGAAACAATG CAACTAAACC

4601  GTAATGAATA TCCGGTGCTT GTCAAGATTA CTCTTGATGA AGGTCAGCCA
      CATTACTTAT AGGCCACGAA CAGTTCTAAT GAGAACTACT TCCAGTCGGT

4651  GCCTATGCGC CTGGTCTGTA CACCGTGCAT CTGTCCTCGT TCAAAGTTGG
      CGGATACGCG GACCAGACAT GTGGCACGTA GACAGGAGCA AGTTTCAACC

4701  TCAGTTCGGT TCTCTTATGA TTGACCGTCT GCGCCTCGTT CCGGCTAAGT
      AGTCAAGCCA AGAGAATACT AACTGGCAGA CGCGGAGCAA GGCCGATTCA

4751  AACATGGAGC AGGTCGCGGA TTTCGACACA ATTTATCAGG CGATGATACA
      TTGTACCTCG TCCAGCGCCT AAAGCTGTGT TAAATAGTCC GCTACTATGT

4801  AATCTCCGTT GTACTTTGTT TCGCGCTTGG TATAATCGCT GGGGGTCAAA
      TTAGAGGCAA CATGAAACAA AGCGCGAACC ATATTAGCGA CCCCCAGTTT

4851  GATGAGTGTT TTAGTGTATT CTTTCGCCTC TTTCGTTTTA GGTTGGTGCC
      CTACTCACAA AATCACATAA GAAAGCGGAG AAAGCAAAAT CCAACCACGG

4901  TTCGTAGTGG CATTACGTAT TTACCCGTT TAATGGAAAC TTCCTCATGC
      AAGCATCACC GTAATGCATA AAATGGGCAA ATTACCTTTG AAGGAGTACG

4951  GTAAGTCTTT AGTCCTCAAA GCCTCCGTAG CCGTTGCTAC CCTCGTTCCG
      CATTCAGAAA TCAGGAGTTT CGGAGGCATC GGCAACGATG GGAGCAAGGC
```

Figure 4H

```
5001  ATGCTGTCTT TCGCTGCTGA GGGTGACGAT CCCGCAAAAG CGGCCTTTGA
      TACGACAGAA AGCGACGACT CCCACTGCTA GGGCGTTTTC GCCGGAAACT

5051  CTCCCTGCAA GCCTCAGCGA CCGAATATAT CGGTTATGCG TGGGCGATGG
      GAGGGACGTT CGGAGTCGCT GGCTTATATA GCCAATACGC ACCCGCTACC

5101  TTGTTGTCAT TGTCGGCGCA ACTATCGGTA TCAAGCTGTT TAAGAAATTC
      AACAACAGTA ACAGCCGCGT TGATAGCCAT AGTTCGACAA ATTCTTTAAG

5151  ACCTCGAAAG CAAGCTGATA AAGGAGGTTT CTCGATCGAG ACGTTGGGTG
      TGGAGCTTTC GTTCGACTAT TTCCTCCAAA GAGCTAGCTC TGCAACCCAC

5201  AGGTTCCAAC TTTCACCATA ATGAAATAAG ATCACTACCG GGCGTATTTT
      TCCAAGGTTG AAAGTGGTAT TACTTTATTC TAGTGATGGC CCGCATAAAA

5251  TTGAGTTATC GAGATTTTCA GGAGCTAAGG AAGCTAAAAT GGAGAAAAAA
      AACTCAATAG CTCTAAAAGT CCTCGATTCC TTCGATTTTA CCTCTTTTTT

5301  ATCACTGGAT ATACCACCGT TGATATATCC CAATGGCATC GTAAAGAACA
      TAGTGACCTA TATGGTGGCA ACTATATAGG GTTACCGTAG CATTTCTTGT

5351  TTTTGAGGCA TTTCAGTCAG TTGCTCAATG TACCTATAAC CAGACCGTTC
      AAAACTCCGT AAAGTCAGTC AACGAGTTAC ATGGATATTG GTCTGGCAAG

5401  AGCTGGATAT TACGGCCTTT TTAAAGACCG TAAAGAAAAA TAAGCACAAG
      TCGACCTATA ATGCCGGAAA AATTTCTGGC ATTTCTTTTT ATTCGTGTTC

5451  TTTTATCCGG CCTTTATTCA CATTCTTGCC CGCCTGATGA ATGCTCATCC
      AAAATAGGCC GGAAATAAGT GTAAGAACGG GCGGACTACT TACGAGTAGG

5501  GGAGTTCCGT ATGGCAATGA AAGACGGTGA GCTGGTGATA TGGGATAGTG
      CCTCAAGGCA TACCGTTACT TTCTGCCACT CGACCACTAT ACCCTATCAC

5551  TTCACCCTTG TTACACCGTT TTCCATGAGC AAACTGAAAC GTTTTCATCG
      AAGTGGGAAC AATGTGGCAA AAGGTACTCG TTTGACTTTG CAAAAGTAGC

5601  CTCTGGAGTG AATACCACGA CGATTTCCGG CAGTTTCTAC ACATATATTC
      GAGACCTCAC TTATGGTGCT GCTAAAGGCC GTCAAAGATG TGTATATAAG

5651  GCAAGATGTG GCGTGTTACG GTGAAAACCT GGCCTATTTC CCTAAAGGGT
      CGTTCTACAC CGCACAATGC CACTTTTGGA CCGGATAAAG GGATTTCCCA

5701  TTATTGAGAA TATGTTTTTC GTCTCAGCCA ATCCCTGGGT GAGTTTCACC
      AATAACTCTT ATACAAAAAG CAGAGTCGGT TAGGGACCCA CTCAAAGTGG

5751  AGTTTTGATT TAAACGTAGC CAATATGGAC AACTTCTTCG CCCCGTTTT
      TCAAAACTAA ATTTGCATCG GTTATACCTG TTGAAGAAGC GGGGGCAAAA

5801  CACTATGGGC AAATATTATA CGCAAGGCGA CAAGGTGCTG ATGCCGCTGG
      GTGATACCCG TTTATAATAT GCGTTCCGCT GTTCCACGAC TACGGCGACC
```

Figure 4I

```
5851  CGATTCAGGT TCATCATGCC GTTTGTGATG GCTTCCATGT CGGCAGAATG
      GCTAAGTCCA AGTAGTACGG CAAACACTAC CGAAGGTACA GCCGTCTTAC

5901  CTTAATGAAT TACAACAGTA CTGCGATGAG TGGCAGGGCG GGGCGTAATT
      GAATTACTTA ATGTTGTCAT GACGCTACTC ACCGTCCCGC CCCGCATTAA

5951  TTTTTAAGGC AGTTATTGGT GCCCTTAAAC GCCTGGTGCT AGCCTGAGGC
      AAAAATTCCG TCAATAACCA CGGGAATTTG CGGACCACGA TCGGACTCCG

6001  CAGTTTGCTC AGGCTCTCCC CGTGGAGGTA ATAATTGCTC GACCGATAAA
      GTCAAACGAG TCCGAGAGGG GCACCTCCAT TATTAACGAG CTGGCTATTT

6051  AGCGGCTTCC TGACAGGAGG CCGTTTTGTT TTGCAGCCCA CCTCAACGCA
      TCGCCGAAGG ACTGTCCTCC GGCAAAACAA AACGTCGGGT GGAGTTGCGT

6101  ATTAATGTGA GTTAGCTCAC TCATTAGGCA CCCCAGGCTT TACACTTTAT
      TAATTACACT CAATCGAGTG AGTAATCCGT GGGGTCCGAA ATGTGAAATA

6151  GCTTCCGGCT CGTATGTTGT GTGGAATTGT GAGCGGATAA CAATTTCACA
      CGAAGGCCGA GCATACAACA CACCTTAACA CTCGCCTATT GTTAAAGTGT

6201  CAGGAAACAG CTATGACCAT GATTACGAAT TCTAGATAA CGAGGGCAAA
      GTCCTTTGTC GATACTGGTA CTAATGCTTA AAGATCTATT GCTCCCGTTT

6251  AAATGAAAAA GACAGCTATC GCGATTGCAG TGGCACTGGC TGGTTTCGCT
      TTTACTTTTT CTGTCGATAG CGCTAACGTC ACCGTGACCG ACCAAAGCGA

6301  ACCGTAGCGC AGGCCGACTA CAAAGATGTC GACTGTATTG TTTATCATGC
      TGGCATCGCG TCCGGCTGAT GTTTCTACAG CTGACATAAC AAATAGTACG

BamHI EcoRI
                                                 - - - - - - - - - - - - - -
6351  TCATTATCTT GTTGCTAAGT GTGGTGGTGG AGGATCCGAA TTCAATGCTG
      AGTAATAGAA CAACGATTCA CACCACCACC TCCTAGGCTT AAGTTACGAC

6401  GCGGCGGCTC TGGTGGTGGT TCTGGTGGCG GCTCTGAGGG TGGTGGCTCT
      CGCCGCCGAG ACCACCACCA AGACCACCGC CGAGACTCCC ACCACCGAGA

6451  GAGGGTGGCG GTTCTGAGGG TGGCGGCTCT GAGGGAGGCG GTTCCGGTGG
      CTCCCACCGC CAAGACTCCC ACCGCCGAGA CTCCCTCCGC CAAGGCCACC

6501  TGGCTCTGGT TCCGGTGATT TTGATTATGA AAAGATGGCA AACGCTAATA
      ACCGAGACCA AGGCCACTAA AACTAATACT TTTCTACCGT TTGCGATTAT

6551  AGGGGGCTAT GACCGAAAAT GCCGATGAAA ACGCGCTACA GTCTGACGCT
      TCCCCCGATA CTGGCTTTTA CGGCTACTTT TGCGCGATGT CAGACTGCGA
```

Figure 4J

```
                                                         ClaI
                                                        ------
6601    AAAGGCAAAC  TTGATTCTGT  CGCTACTGAT  TACGGTGCTG  CTATCGATGG
        TTTCCGTTTG  AACTAAGACA  GCGATGACTA  ATGCCACGAC  GATAGCTACC

6651    TTTCATTGGT  GACGTTTCCG  GCCTTGCTAA  TGGTAATGGT  GCTACTGGTG
        AAAGTAACCA  CTGCAAAGGC  CGGAACGATT  ACCATTACCA  CGATGACCAC

6701    ATTTTGCTGG  CTCTAATTCC  CAAATGGCTC  AAGTCGGTGA  CGGTGATAAT
        TAAAACGACC  GAGATTAAGG  GTTTACCGAG  TTCAGCCACT  GCCACTATTA

6751    TCACCTTTAA  TGAATAATTT  CCGTCAATAT  TTACCTTCCC  TCCCTCAATC
        AGTGGAAATT  ACTTATTAAA  GGCAGTTATA  AATGGAAGGG  AGGGAGTTAG

6801    GGTTGAATGT  CGCCCTTTTG  TCTTTGGCGC  TGGTAAACCA  TATGAATTTT
        CCAACTTACA  GCGGGAAAAC  AGAAACCGCG  ACCATTTGGT  ATACTTAAAA

6851    CTATTGATTG  TGACAAAATA  AACTTATTCC  GTGGTGTCTT  TGCGTTTCTT
        GATAACTAAC  ACTGTTTTAT  TTGAATAAGG  CACCACAGAA  ACGCAAAGAA

6901    TTATATGTTG  CCACCTTTAT  GTATGTATTT  TCTACGTTTG  CTAACATACT
        AATATACAAC  GGTGGAAATA  CATACATAAA  AGATGCAAAC  GATTGTATGA

HindIII

6951    GCGTAATAAG  GAGTCTTGAT  A
        CGCATTATTC  CTCAGAACTA  T
```

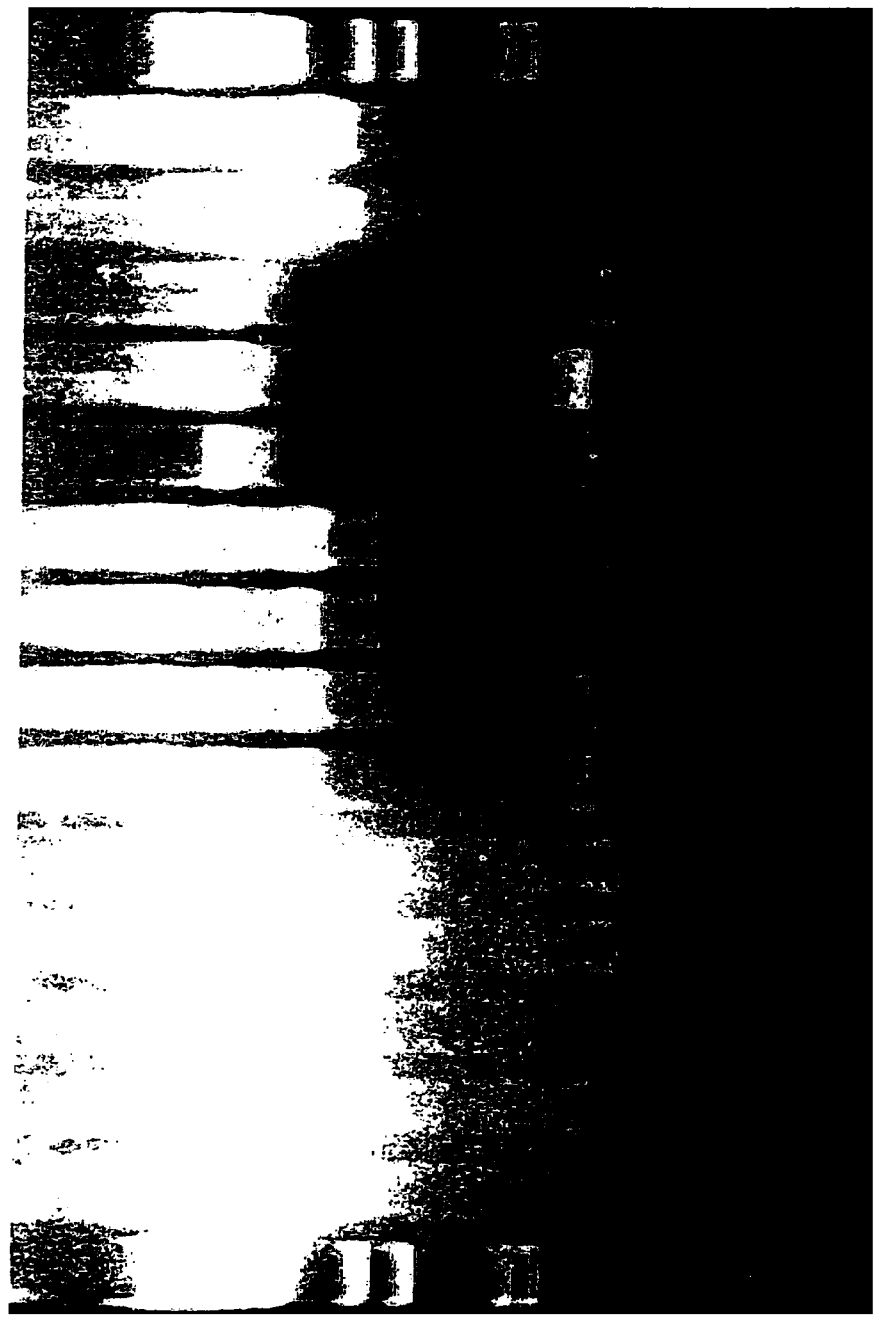

Figure 7

| pep3/p75ICD | jun/p75ICD | transductants (t.u./ml)* |
|---|---|---|
| 1 | pos. control | $6 \times 10^5$ |
| - | neg. control | 0 |
| 1 | $10^2$ | $1.2 \times 10^4$ |
| 1 | $10^3$ | $8.6 \times 10^2$ |
| 1 | $10^4$ | $1.2 \times 10^2$ |
| 1 | $10^5$ | $12^{\#}$ |
| 1 | $10^6$ | $1.2^{\#}$ |
| 1 | $10^7$ | $0.12^{\#}$ |

SEQUENCE LISTING

```
<160> NUMBER OF SEQ ID NOS: 50

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: primer
      CAT_BspEI(for)

<400> SEQUENCE: 1
gaatgctcat ccggagttc                                                  19

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: primer
      CAT_Bsu36I(rev)

<400> SEQUENCE: 2
tttcactggc ctcaggctag caccaggcgt ttaag                                35

<210> SEQ ID NO 3
<211> LENGTH: 7783
<212> TYPE: DNA
<213> ORGANISM: Artificial Sequence
<220> FEATURE:
<223> OTHER INFORMATION: Description of Artificial Sequence: phage
      vector fhag1A (circular)
<220> FEATURE:
<221> NAME/KEY: gene
<222> LOCATION: (1)..(828)
<223> OTHER INFORMATION: C-terminus gene II
<220> FEATURE:
<221> NAME/KEY: gene
<222> LOCATION: (496)..(828)
<223> OTHER INFORMATION: gene X
<220> FEATURE:
<221> NAME/KEY: gene
<222> LOCATION: (843)..(1103)
<223> OTHER INFORMATION: gene V
```

```
<220> FEATURE:
<221> NAME/KEY: gene
<222> LOCATION: (1108)..(1206)
<223> OTHER INFORMATION: gene VII
<220> FEATURE:
<221> NAME/KEY: gene
<222> LOCATION: (1206)..(1313)
<223> OTHER INFORMATION: gene IX
<220> FEATURE:
<221> NAME/KEY: gene
<222> LOCATION: (1301)..(1519)
<223> OTHER INFORMATION: gene VIII
<220> FEATURE:
<221> NAME/KEY: gene
<222> LOCATION: (1643)..(2299)
<223> OTHER INFORMATION: cat resistance gene
<220> FEATURE:
<221> NAME/KEY: gene
<222> LOCATION: (2769)..(4136)
<223> OTHER INFORMATION: ompA-FLAG-scFv(anti-HAG)-gene IIIss
<220> FEATURE:
<221> NAME/KEY: misc_feature
<222> LOCATION: (2769)..(2831)
<223> OTHER INFORMATION: ompA signal sequence
<220> FEATURE:
<221> NAME/KEY: misc_feature
<222> LOCATION: (2832)..(2843)
<223> OTHER INFORMATION: FLAG peptide
<220> FEATURE:
<221> NAME/KEY: misc_feature
<222> LOCATION: (2844)..(3641)
<223> OTHER INFORMATION: scFv (anti-HAG)
<220> FEATURE:
<221> NAME/KEY: misc_feature
<222> LOCATION: (3666)..(4139)
<223> OTHER INFORMATION: gene IIIss
<220> FEATURE:
<221> NAME/KEY: gene
<222> LOCATION: (4231)..(4566)
<223> OTHER INFORMATION: gene VI
<220> FEATURE:
<221> NAME/KEY: gene
<222> LOCATION: (4572)..(5615)
<223> OTHER INFORMATION: gene I
<220> FEATURE:
<221> NAME/KEY: gene
<222> LOCATION: (5596)..(6873)
<223> OTHER INFORMATION: gene IV
<220> FEATURE:
<221> NAME/KEY: gene
<222> LOCATION: (7382)..(7783)
<223> OTHER INFORMATION: N-terminus gene II
<220> FEATURE:
<221> NAME/KEY: -10_signal
<222> LOCATION: (2679)..(2683)
<220> FEATURE:
<221> NAME/KEY: -35_signal
<222> LOCATION: (2656)..(2660)
<220> FEATURE:
<221> NAME/KEY: misc_feature
<222> LOCATION: (2684)..(2718)
<223> OTHER INFORMATION: lac operator
<220> FEATURE:
<221> NAME/KEY: rep_origin
<222> LOCATION: (6992)..(7137)
<223> OTHER INFORMATION: fd ori
<220> FEATURE:
<221> NAME/KEY: misc_signal
<222> LOCATION: (6874)..(6952)
<223> OTHER INFORMATION: packaging signal
<220> FEATURE:
<221> NAME/KEY: terminator
<222> LOCATION: (4178)..(4220)
<223> OTHER INFORMATION: fd terminator
<220> FEATURE:
<221> NAME/KEY: modified_base
<222> LOCATION: (1550)..(1553)
<223> OTHER INFORMATION: a, t, c, g, other or unknown
```

<400> SEQUENCE: 3

```
aacgctacta ccattagtag aattgatgcc accttttcag ctcgcgcccc aaatgaaaat      60
atagctaaac aggttattga ccatttgcga aatgtatcta atggtcaaac taaatctact     120
cgttcgcaga attgggaatc aactgttaca tggaatgaaa cttccagaca ccgtacttta     180
gttgcatatt taaaacatgt tgaactacag caccagattc agcaattaag ctctaagcca     240
tccgcaaaaa tgacctctta tcaaaaggag caattaaagg tactgtctaa tcctgacctg     300
ttggaatttg cttccggtct ggttcgcttt gaggctcgaa ttgaaacgcg atatttgaag     360
tctttcgggc ttcctcttaa tcttttttgat gcaattcgct ttgcttctga ctataataga     420
cagggtaaag acctgatttt tgatttatgg tcattctcgt tttctgaact gtttaaagca     480
tttgaggggg attcaatgaa tatttatgac gattccgcag tattggacgc tatccagtct     540
aaacatttta caattacccc ctctggcaaa acttcctttg caaaagcctc tcgctatttt     600
ggtttctatc gtcgtctggt taatgagggt tatgatagtg ttgctcttac catgcctcgt     660
aattcctttt ggcgttatgt atctgcatta gttgagtgtg gtattcctaa atctcaattg     720
atgaatcttt ccacctgtaa taatgttgtt ccgttagttc gttttattaa cgtagatttt     780
tcctcccaac gtcctgactg gtataatgag ccagttctta aaatcgcata aggtaattca     840
aaatgattaa agttgaaatt aaaccgtctc aagcgcaatt tactacccgt tctggtgttt     900
ctcgtcaggg caagccttat tcactgaatg agcagctttg ttacgttgat tgggtaatg      960
aatatccggt gcttgtcaag attactctcg acgaaggtca gccagcgtat gcgcctggtc    1020
tgtacaccgt gcatctgtcc tcgttcaaag ttggtcagtt cggttctctt atgattgacc    1080
gtctgcgcct cgttccggct aagtaacatg gagcaggtcg cggatttcga cacaatttat    1140
caggcgatga tacaaatctc cgttgtactt tgtttcgcgc ttggtataat cgctgggggt    1200
caaagatgag tgttttagtg tattcttttcg cctctttcgt tttaggttgg tgccttcgta    1260
gtggcattac gtatttttacc cgtttaatgg aaacttcctc atgcgtaagt ctttagtcct    1320
caaagcctcc gtagccgttg ctaccctcgt tccgatgctg tctttcgctg ctgagggtga    1380
cgatcccgca aaagcggcct ttgactccct gcaagcctca gcgaccgaat atatcggtta    1440
tgcgtgggcg atggttgttg tcattgtcgg cgcaactatc ggtatcaagc tgtttaagaa    1500
attcacctcg aaagcaagct gataaaggag gtttctcgat cgagacgttn nngaggttc     1560
caactttcac cataatgaaa taagatcact accgggcgta ttttttgagt tatcgagatt    1620
ttcaggagct aaggaagcta aaatggagaa aaaaatcact ggatatacca ccgttgatat    1680
atcccaatgg catcgtaaag aacattttga ggcatttcag tcagttgctc aatgtaccta    1740
taaccagacc gttcagctgg atattacggc ctttttaaag accgtaaaga aaataagca     1800
caagttttat ccggccttta ttcacattct tgcccgcctg atgaatgctc atccggagtt    1860
ccgtatggca atgaaagacg gtgagctggt gatatgggat agtgttcacc cttgttacac    1920
cgttttccat gagcaaactg aaacgttttc atcgctctgg agtgaatacc acgacgattt    1980
ccggcagttt ctacacatat attcgcaaga tgtggcgtgt tacggtgaaa acctggccta    2040
tttccctaaa gggtttattg agaatatgtt tttcgtctca gccaatccct gggtgagttt    2100
caccagtttt gatttaaacg tggccaatat ggacaacttc ttcgcccccg ttttcaccat    2160
gggcaaatat tatacgcaag gcgacaaggt gctgatgccg ctggcgattc aggttcatca    2220
tgccgtctgt gatggcttcc atgtcggcag aatgcttaat gaattacaac agtactgcga    2280
tgagtggcag ggcggggcgt aatttttttta aggcagttat tggtgccctt aaacgcctgg    2340
```

-continued

```
tgctacgcct gaataagtga taataagcgg atgaatggca gaaattcgaa agcaaattcg    2400
acccggtcgt cggttcaggg cagggtcgtt aaatagccgc ttatgtctat tgctggttta    2460
ccggtttatt gactaccgga agcagtgtga ccgtgtgctt ctcaaatgcc tgaggccagt    2520
ttgctcaggc tctcccgtg gaggtaataa ttgctcgacc gataaaagcg gcttcctgac    2580
aggaggccgt tttgttttgc agcccacctc aacgcaatta atgtgagtta gctcactcat    2640
taggcacccc aggctttaca ctttatgctt ccggctcgta tgttgtgtgg aattgtgagc    2700
ggataacaat ttcacacagg aaacagctat gaccatgatt acgaatttct agataacgag    2760
ggcaaatcat gaaaaagaca gctatcgcga ttgcagtggc actggctggt ttcgctaccg    2820
tagcgcaggc cgactacaaa gatatcgtta tgacccagtc accgtcctcc ctgaccgtta    2880
ccgctggtga aaaagttacc atgtcctgca cctcctccca gtccctgttc aactccggta    2940
aacagaaaaa ctacctgacc tggtatcagc agaaaccggg tcagccaccg aaagttctga    3000
tctactgggg ttccacccgt gaatccgtg ttccagaccg tttcaccggt tccggttccg    3060
gcaccgactt caccctgacc atctcctccg ttcaggctga agacctggct gtttactact    3120
gccagaacga ctactccaac ccactgacct tcggtggtgg caccaaactg gaacttaagc    3180
gcgctggtgg tggagggtct ggaggaggtg ggagtggggg aggtggatcc ggcgggggag    3240
gttcaggggg tggcggtagt ggaggggcg gttcagaagt tcaactagtt gaatccggtg    3300
gtgacctggt taaaccgggt ggttccctga actgtcctg cgctgcttcc ggtttctcct    3360
tctcctccta cggtatgtcc tgggttcgtc agacccgga caaacgtctg gaatgggttg    3420
ctaccatctc caacggtggt ggttacacct actacccgga ctccgttaaa ggtcgtttca    3480
ccatctcccg tgacaacgct aaaaacaccc tgtacctgca gatgtcctcc ctgaaatccg    3540
aagactcagc tatgtactac tgcgctcgtc gtgaacgtta cgacgaaaac ggtttcgctt    3600
actggggtca gggtaccctg gttaccgttt cagcttccgg agaattcgag gcctcggggg    3660
ccgagggcgg cggttctggt tccggtgatt ttgattatga aaaaatggca aacgctaata    3720 aggggggctat gaccgaaaat gccgatgaaa acgcgctaca gtctgacgct aaaggcaaac    3780
ttgattctgt cgctactgat tacggtgctg ctatcgatgg tttcattggt gacgtttccg    3840
gccttgctaa tggtaatggt gctactggtg attttgctgg ctctaattcc caaatggctc    3900
aagtcggtga cggtgataat tcacctttaa tgaataattt ccgtcaatat ttaccttccc    3960
tccctcaatc ggttgaatgt cgcccttttg tctttggcgc tggtaaacca tatgaatttt    4020
ctattgattg tgacaaaata aacttattcc gtggtgtctt tgcgtttctt ttatatgttg    4080
ccacctttat gtatgtattt tctacgtttg ctaacatact gcgtaataag gagtcttgat    4140
aagcttcgag aaattcacct cgaaagcaag ctgataaacc gatacaatta aaggctcctt    4200
ttggagcctt ttttttgga gaattcaatc atgccagttc ttttgggtat tccgttatta    4260
ttgcgtttcc tcggttcct tctggtaact ttgttcggct atctgcttac tttccttaaa    4320
aagggcttcg gtaagatagc tattgctatt tcattgtttc ttgctcttat tattgggctt    4380
aactcaattc ttgtgggtta tctctctgat attagcgcac aattaccctc tgattttgtt    4440
cagggcgttc agttaattct cccgtctaat gcgcttccct gtttttatgt tattctctct    4500
gtaaaggctg ctattttcat ttttgacgtt aaacaaaaaa tcgtttctta tttggattgg    4560
gataaataaa tatggctgtt tattttgtaa ctggcaaatt aggctctgga agacgctcg    4620 ttagcgttgg taagattcag gataaaattg tagctgggtg caaaatagca actaatcttg    4680
atttaaggct tcaaaacctc ccgcaagtcg ggaggttcgc taaaacgcct cgcgttctta    4740
```

```
gaataccgga taagccttct atttctgatt tgcttgctat tggtcgtggt aatgattcct    4800
acgacgaaaa taaaaacggt ttgcttgttc ttgatgaatg cggtacttgg tttaataccc    4860
gttcatggaa tgacaaggaa agacagccga ttattgattg gtttcttcat gctcgtaaat    4920
tgggatggga tattattttt cttgttcagg atttatctat tgttgataaa caggcgcgtt    4980
ctgcattagc tgaacacgtt gtttattgtc gccgtctgga cagaattact ttaccctttg    5040
tcggcacttt atattctctt gttactggct caaaaatgcc tctgcctaaa ttacatgttg    5100
gtgttgttaa atatggtgat tctcaattaa gccctactgt tgagcgttgg ctttatactg    5160
gtaagaattt atataacgca tatgacacta acaggctttt tccagtaat tatgattcag     5220
gtgtttattc atatttaacc ccttatttat cacacggtcg gtatttcaaa ccattaaatt    5280
taggtcagaa gatgaaatta actaaaatat atttgaaaaa gttttctcgc gttctttgtc    5340
ttgcgatagg atttgcatca gcatttacat atagttatat aacccaacct aagccggagg    5400
ttaaaaaggt agtctctcag acctatgatt ttgataaatt cactattgac tcttctcagc    5460
gtcttaatct aagctatcgc tatgttttca aggattctaa gggaaaatta attaatagcg    5520
acgatttaca gaagcaaggt tattccatca catatattga tttatgtact gtttcaatta    5580
aaaaaggtaa ttcaaatgaa attgttaaat gtaattaatt ttgttttctt gatgtttgtt    5640
tcatcatctt cttttgctca gtaattgaa atgaataatt cgcctctgcg cgatttcgtg    5700
acttggtatt caaagcaaac aggtgaatct gttattgtct cacctgatgt taaaggtaca    5760
gtgactgtat attcctctga cgttaagcct gaaaatttac gcaatttctt tatctctgtt    5820
ttacgtgcta ataattttga tatggttggc tcaattcctt ccataattca gaaatataac    5880
ccaaatagtc aggattatat tgatgaattg ccatcatctg atattcagga atatgatgat    5940
aattccgctc cttctggtgg tttctttgtt ccgcaaaatg ataatgttac tcaaacattt    6000
aaaattaata acgttcgcgc aaaggattta ataagggttg tagaattgtt tgttaaatct    6060
aatacatcta atcctcaaa tgtattatct gttgatggt ctaacttatt agtagttagc      6120
gcccctaaag atattttaga taaccttccg caatttcttt ctactgttga tttgccaact    6180
gaccagatat tgattgaagg attaattttc gaggttcagc aaggtgatgc tttagatttt    6240
tcctttgctg ctggctctca gcgcggcact gttgctggtg tgttaatac tgaccgtcta     6300
acctctgttt tatcttctgc gggtggttcg ttcggtattt taacggcga tgttttaggg    6360
ctatcagttc gcgcattaaa gactaatagc cattcaaaaa tattgtctgt gcctcgtatt    6420
cttacgcttt caggtcagaa gggttctatt tctgttggcc agaatgtccc ttttattact    6480
ggtcgtgtaa ctggtgaatc tgccaatgta aataatccat tcagacggt tgagcgtcaa     6540
aatgttggta tttctatgag tgttttccc gttgcaatgg ctggcggtaa tattgtttta     6600
gatataacca gtaaggccga tagtttgagt tcttctactc aggcaagtga tgttattact    6660
aatcaaagaa gtattgcgac aacggttaat ttgcgtgatg tcagactct tttgctcggt     6720
ggcctcactg attacaaaaa cacttctcaa gattctggtg tgccgttcct gtctaaaatc    6780
cctttaatcg gcctcctgtt tagctcccgt tctgattcta acgaggaaag cacgttgtac    6840
gtgctcgtca aagcaaccat agtacgcgcc ctgtagcggc gcattaagcg cggcgggtgt    6900
ggtggttacg cgcagcgtga ccgctacact tgccagcgcc ctagcgcccg ctcctttcgc    6960
tttcttccct tcctttctcg ccacgttctc cggctttccc cgtcaagctc taaatcgggg    7020
gatcccttta gggttccgat ttagtgcttt acggcacctc gaccccaaa aacttgattt     7080
gggtgatggt tcacgtagtg ggccatcgcc ctgatagacg gttttcgcc ctttgacgtt      7140
```

-continued

```
ggagtccacg ttctttaata gtggactctt gttccaaact ggaacaacac tcacaactaa    7200
ctcggcctat tcttttgatt tataaggatt tttgtcattt tctgcttact ggttaaaaaa    7260
taagctgatt taacaaatat ttaacgcgaa atttaacaaa acattaacgt ttacaattta    7320
aatatttgct tatacaatca tcctgttttt ggggcttttc tgattatcaa ccggggtaca    7380
tatgattgac atgctagttt tacgattacc gttcatcgat tctcttgttt gctccagact    7440
ttcaggtaat gacctgatag cctttgtaga cctctcaaaa atagctaccc ctccggcat    7500 gaatttatca gctagaacgg ttgaatatca tattgacggt gatttgactg tctccggcct    7560
ttctcacccg tttgaatctt tgcctactca ttactccggc attgcattta aaatatatga    7620
gggttctaaa aatttttatc cctgcgttga aattaaggct tcaccagcaa agtattaca    7680 gggtcataat gttttggta caaccgattt agctttatgc tctgaggctt tattgcttaa    7740 ttttgctaa ctctctgcct tgcttgtacg atttattggat gtt                      7783
```

<210> SEQ ID NO 4
<211> LENGTH: 276
<212> TYPE: PRT
<213> ORGANISM: Artificial Sequence
<220> FEATURE:
<223> OTHER INFORMATION: Description of Artificial Sequence: C-terminus of gene II protein encoded by phage vector fhag1A (circular)

<400> SEQUENCE: 4

```
Asn Ala Thr Thr Ile Ser Arg Ile Asp Ala Thr Phe Ser Ala Arg Ala
 1               5                  10                  15

Pro Asn Glu Asn Ile Ala Lys Gln Val Ile Asp His Leu Arg Asn Val
            20                  25                  30

Ser Asn Gly Gln Thr Lys Ser Thr Arg Ser Gln Asn Trp Glu Ser Thr
        35                  40                  45

Val Thr Trp Asn Glu Thr Ser Arg His Arg Thr Leu Val Ala Tyr Leu
    50                  55                  60

Lys His Val Glu Leu Gln His Gln Ile Gln Gln Leu Ser Ser Lys Pro
65                  70                  75                  80

Ser Ala Lys Met Thr Ser Tyr Gln Lys Glu Gln Leu Lys Val Leu Ser
                85                  90                  95

Asn Pro Asp Leu Leu Glu Phe Ala Ser Gly Leu Val Arg Phe Glu Ala
            100                 105                 110

Arg Ile Glu Thr Arg Tyr Leu Lys Ser Phe Gly Leu Pro Leu Asn Leu
        115                 120                 125

Phe Asp Ala Ile Arg Phe Ala Ser Asp Tyr Asn Arg Gln Gly Lys Asp
    130                 135                 140

Leu Ile Phe Asp Leu Trp Ser Phe Ser Phe Ser Glu Leu Phe Lys Ala
145                 150                 155                 160

Phe Glu Gly Asp Ser Met Asn Ile Tyr Asp Asp Ser Ala Val Leu Asp
                165                 170                 175

Ala Ile Gln Ser Lys His Phe Thr Ile Thr Pro Ser Gly Lys Thr Ser
            180                 185                 190

Phe Ala Lys Ala Ser Arg Tyr Phe Gly Phe Tyr Arg Arg Leu Val Asn
        195                 200                 205

Glu Gly Tyr Asp Ser Val Ala Leu Thr Met Pro Arg Asn Ser Phe Trp
    210                 215                 220

Arg Tyr Val Ser Ala Leu Val Glu Cys Gly Ile Pro Lys Ser Gln Leu
225                 230                 235                 240
```

```
Met Asn Leu Ser Thr Cys Asn Val Val Pro Leu Val Arg Phe Ile
            245                 250                 255

Asn Val Asp Phe Ser Ser Gln Arg Pro Asp Trp Tyr Asn Glu Pro Val
            260                 265                 270

Leu Lys Ile Ala
        275

<210> SEQ ID NO 5
<211> LENGTH: 111
<212> TYPE: PRT
<213> ORGANISM: Artificial Sequence
<220> FEATURE:
<223> OTHER INFORMATION: Description of Artificial Sequence: gene X
      protein encoded by phage vector fhag1A (circular)

<400> SEQUENCE: 5

Met Asn Ile Tyr Asp Asp Ser Ala Val Leu Asp Ala Ile Gln Ser Lys
  1               5                  10                  15

His Phe Thr Ile Thr Pro Ser Gly Lys Thr Ser Phe Ala Lys Ala Ser
             20                  25                  30

Arg Tyr Phe Gly Phe Tyr Arg Arg Leu Val Asn Glu Gly Tyr Asp Ser
         35                  40                  45

Val Ala Leu Thr Met Pro Arg Asn Ser Phe Trp Arg Tyr Val Ser Ala
     50                  55                  60

Leu Val Glu Cys Gly Ile Pro Lys Ser Gln Leu Met Asn Leu Ser Thr
 65                  70                  75                  80

Cys Asn Asn Val Val Pro Leu Val Arg Phe Ile Asn Val Asp Phe Ser
                 85                  90                  95

Ser Gln Arg Pro Asp Trp Tyr Asn Glu Pro Val Leu Lys Ile Ala
            100                 105                 110

<210> SEQ ID NO 6
<211> LENGTH: 87
<212> TYPE: PRT
<213> ORGANISM: Artificial Sequence
<220> FEATURE:
<223> OTHER INFORMATION: Description of Artificial Sequence: gene V
      protein encoded by phage vector fhag1A (circular)

<400> SEQUENCE: 6

Met Ile Lys Val Glu Ile Lys Pro Ser Gln Ala Gln Phe Thr Thr Arg
  1               5                  10                  15

Ser Gly Val Ser Arg Gln Gly Lys Pro Tyr Ser Leu Asn Glu Gln Leu
             20                  25                  30

Cys Tyr Val Asp Leu Gly Asn Glu Tyr Pro Val Leu Val Lys Ile Thr
         35                  40                  45

Leu Asp Glu Gly Gln Pro Ala Tyr Ala Pro Gly Leu Tyr Thr Val His
     50                  55                  60

Leu Ser Ser Phe Lys Val Gly Gln Phe Gly Ser Leu Met Ile Asp Arg
 65                  70                  75                  80

Leu Arg Leu Val Pro Ala Lys
                85

<210> SEQ ID NO 7
<211> LENGTH: 33
<212> TYPE: PRT
<213> ORGANISM: Artificial Sequence
<220> FEATURE:
<223> OTHER INFORMATION: Description of Artificial Sequence: gene VII
      protein encoded by phage vector fhag1A (circular)
```

-continued

<400> SEQUENCE: 7

Met Glu Gln Val Ala Asp Phe Asp Thr Ile Tyr Gln Ala Met Ile Gln
1               5                   10                  15

Ile Ser Val Val Leu Cys Phe Ala Leu Gly Ile Ile Ala Gly Gly Gln
            20                  25                  30

Arg

<210> SEQ ID NO 8
<211> LENGTH: 36
<212> TYPE: PRT
<213> ORGANISM: Artificial Sequence
<220> FEATURE:
<223> OTHER INFORMATION: Description of Artificial Sequence: gene IX
      protein encoded by phage vector fhag1A (circular)

<400> SEQUENCE: 8

Met Ser Val Leu Val Tyr Ser Phe Ala Ser Phe Val Leu Gly Trp Cys
1               5                   10                  15

Leu Arg Ser Gly Ile Thr Tyr Phe Thr Arg Leu Met Glu Thr Ser Ser
            20                  25                  30

Cys Val Ser Leu
        35

<210> SEQ ID NO 9
<211> LENGTH: 73
<212> TYPE: PRT
<213> ORGANISM: Artificial Sequence
<220> FEATURE:
<223> OTHER INFORMATION: Description of Artificial Sequence: gene VIII
      protein encoded by phage vector fhag1A (circular)

<400> SEQUENCE: 9

Met Arg Lys Ser Leu Val Leu Lys Ala Ser Val Ala Val Ala Thr Leu
1               5                   10                  15

Val Pro Met Leu Ser Phe Ala Ala Glu Gly Asp Asp Pro Ala Lys Ala
            20                  25                  30

Ala Phe Asp Ser Leu Gln Ala Ser Ala Thr Glu Tyr Ile Gly Tyr Ala
        35                  40                  45

Trp Ala Met Val Val Val Ile Val Gly Ala Thr Ile Gly Ile Lys Leu
    50                  55                  60

Phe Lys Lys Phe Thr Ser Lys Ala Ser
65                  70

<210> SEQ ID NO 10
<211> LENGTH: 219
<212> TYPE: PRT
<213> ORGANISM: Artificial Sequence
<220> FEATURE:
<223> OTHER INFORMATION: Description of Artificial Sequence: cat protein
      encoded by phage vector fhag1A (circular)

<400> SEQUENCE: 10

Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
            20                  25                  30

Tyr Asn Gln Thr Val Gln Leu Asp Ile Thr Ala Phe Leu Lys Thr Val
        35                  40                  45

Lys Lys Asn Lys His Lys Phe Tyr Pro Ala Phe Ile His Ile Leu Ala
    50                  55                  60

```
Arg Leu Met Asn Ala His Pro Glu Phe Arg Met Ala Met Lys Asp Gly
 65                  70                  75                  80

Glu Leu Val Ile Trp Asp Ser Val His Pro Cys Tyr Thr Val Phe His
                 85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Met Leu Asn Glu Leu
        195                 200                 205

Gln Gln Tyr Cys Asp Glu Trp Gln Gly Gly Ala
    210                 215

<210> SEQ ID NO 11
<211> LENGTH: 456
<212> TYPE: PRT
<213> ORGANISM: Artificial Sequence
<220> FEATURE:
<223> OTHER INFORMATION: Description of Artificial Sequence: ompA-FLAG-
      scFv (anti-HAG)-gene IIIss encoded by phage vector fhag1A
      (circular)

<400> SEQUENCE: 11

Met Lys Lys Thr Ala Ile Ala Ile Ala Val Ala Leu Ala Gly Phe Ala
  1               5                  10                  15

Thr Val Ala Gln Ala Asp Tyr Lys Asp Ile Val Met Thr Gln Ser Pro
             20                  25                  30

Ser Ser Leu Thr Val Thr Ala Gly Glu Lys Val Thr Met Ser Cys Thr
         35                  40                  45

Ser Ser Gln Ser Leu Phe Asn Ser Gly Lys Gln Lys Asn Tyr Leu Thr
     50                  55                  60

Trp Tyr Gln Gln Lys Pro Gly Gln Pro Pro Lys Val Leu Ile Tyr Trp
 65                  70                  75                  80

Ala Ser Thr Arg Glu Ser Gly Val Pro Asp Arg Phe Thr Gly Ser Gly
                 85                  90                  95

Ser Gly Thr Asp Phe Thr Leu Thr Ile Ser Ser Val Gln Ala Glu Asp
            100                 105                 110

Leu Ala Val Tyr Tyr Cys Gln Asn Asp Tyr Ser Asn Pro Leu Thr Phe
        115                 120                 125

Gly Gly Gly Thr Lys Leu Glu Leu Lys Arg Ala Gly Gly Gly Gly Ser
    130                 135                 140

Gly Gly Gly Gly Ser Gly Gly Gly Ser Gly Gly Gly Gly Ser Gly
145                 150                 155                 160

Gly Gly Ser Gly Gly Gly Gly Ser Glu Val Gln Leu Val Glu Ser
                165                 170                 175

Gly Gly Asp Leu Val Lys Pro Gly Gly Ser Leu Lys Leu Ser Cys Ala
            180                 185                 190
```

-continued

```
Ala Ser Gly Phe Ser Phe Ser Ser Tyr Gly Met Ser Trp Val Arg Gln
            195                 200                 205

Thr Pro Asp Lys Arg Leu Glu Trp Val Ala Thr Ile Ser Asn Gly Gly
    210                 215                 220

Gly Tyr Thr Tyr Tyr Pro Asp Ser Val Lys Gly Arg Phe Thr Ile Ser
225                 230                 235                 240

Arg Asp Asn Ala Lys Asn Thr Leu Tyr Leu Gln Met Ser Ser Leu Lys
                245                 250                 255

Ser Glu Asp Ser Ala Met Tyr Tyr Cys Ala Arg Arg Glu Arg Tyr Asp
            260                 265                 270

Glu Asn Gly Phe Ala Tyr Trp Gly Gln Gly Thr Leu Val Thr Val Ser
        275                 280                 285

Ala Ser Gly Glu Phe Glu Ala Ser Gly Ala Glu Gly Gly Ser Gly
    290                 295                 300

Ser Gly Asp Phe Asp Tyr Glu Lys Met Ala Asn Ala Asn Lys Gly Ala
305                 310                 315                 320

Met Thr Glu Asn Ala Asp Glu Asn Ala Leu Gln Ser Asp Ala Lys Gly
                325                 330                 335

Lys Leu Asp Ser Val Ala Thr Asp Tyr Gly Ala Ala Ile Asp Gly Phe
            340                 345                 350

Ile Gly Asp Val Ser Gly Leu Ala Asn Gly Asn Gly Ala Thr Gly Asp
        355                 360                 365

Phe Ala Gly Ser Asn Ser Gln Met Ala Gln Val Gly Asp Gly Asp Asn
    370                 375                 380

Ser Pro Leu Met Asn Asn Phe Arg Gln Tyr Leu Pro Ser Leu Pro Gln
385                 390                 395                 400

Ser Val Glu Cys Arg Pro Phe Val Phe Gly Ala Gly Lys Pro Tyr Glu
                405                 410                 415

Phe Ser Ile Asp Cys Asp Lys Ile Asn Leu Phe Arg Gly Val Phe Ala
            420                 425                 430

Phe Leu Leu Tyr Val Ala Thr Phe Met Tyr Val Phe Ser Thr Phe Ala
        435                 440                 445

Asn Ile Leu Arg Asn Lys Glu Ser
    450                 455
```

<210> SEQ ID NO 12
<211> LENGTH: 112
<212> TYPE: PRT
<213> ORGANISM: Artificial Sequence
<220> FEATURE:
<223> OTHER INFORMATION: Description of Artificial Sequence: gene VI
    protein encoded by phage vector fhag1A (circular)

<400> SEQUENCE: 12

```
Met Pro Val Leu Leu Gly Ile Pro Leu Leu Arg Phe Leu Gly Phe
 1               5                  10                  15

Leu Leu Val Thr Leu Phe Gly Tyr Leu Leu Thr Phe Leu Lys Lys Gly
            20                  25                  30

Phe Gly Lys Ile Ala Ile Ala Ile Ser Leu Phe Leu Ala Leu Ile Ile
        35                  40                  45

Gly Leu Asn Ser Ile Leu Val Gly Tyr Leu Ser Asp Ile Ser Ala Gln
    50                  55                  60

Leu Pro Ser Asp Phe Val Gln Gly Val Gln Leu Ile Leu Pro Ser Asn
65                  70                  75                  80
```

-continued

```
Ala Leu Pro Cys Phe Tyr Val Ile Leu Ser Val Lys Ala Ala Ile Phe
                85                  90                  95

Ile Phe Asp Val Lys Gln Lys Ile Val Ser Tyr Leu Asp Trp Asp Lys
            100                 105                 110
```

<210> SEQ ID NO 13
<211> LENGTH: 348
<212> TYPE: PRT
<213> ORGANISM: Artificial Sequence
<220> FEATURE:
<223> OTHER INFORMATION: Description of Artificial Sequence: gene I
      protein encoded by phage vector fhag1A (circular)

<400> SEQUENCE: 13

```
Met Ala Val Tyr Phe Val Thr Gly Lys Leu Gly Ser Gly Lys Thr Leu
  1               5                  10                  15

Val Ser Val Gly Lys Ile Gln Asp Lys Ile Val Ala Gly Cys Lys Ile
             20                  25                  30

Ala Thr Asn Leu Asp Leu Arg Leu Gln Asn Leu Pro Gln Val Gly Arg
         35                  40                  45

Phe Ala Lys Thr Pro Arg Val Leu Arg Ile Pro Asp Lys Pro Ser Ile
     50                  55                  60

Ser Asp Leu Leu Ala Ile Gly Arg Gly Asn Asp Ser Tyr Asp Glu Asn
 65                  70                  75                  80

Lys Asn Gly Leu Leu Val Leu Asp Glu Cys Gly Thr Trp Phe Asn Thr
                 85                  90                  95

Arg Ser Trp Asn Asp Lys Glu Arg Gln Pro Ile Ile Asp Trp Phe Leu
            100                 105                 110

His Ala Arg Lys Leu Gly Trp Asp Ile Ile Phe Leu Val Gln Asp Leu
        115                 120                 125

Ser Ile Val Asp Lys Gln Ala Arg Ser Ala Leu Ala Glu His Val Val
130                 135                 140

Tyr Cys Arg Arg Leu Asp Arg Ile Thr Leu Pro Phe Val Gly Thr Leu
145                 150                 155                 160

Tyr Ser Leu Val Thr Gly Ser Lys Met Pro Leu Pro Lys Leu His Val
                165                 170                 175

Gly Val Val Lys Tyr Gly Asp Ser Gln Leu Ser Pro Thr Val Glu Arg
            180                 185                 190

Trp Leu Tyr Thr Gly Lys Asn Leu Tyr Asn Ala Tyr Asp Thr Lys Gln
        195                 200                 205

Ala Phe Ser Ser Asn Tyr Asp Ser Gly Val Tyr Ser Tyr Leu Thr Pro
    210                 215                 220

Tyr Leu Ser His Gly Arg Tyr Phe Lys Pro Leu Asn Leu Gly Gln Lys
225                 230                 235                 240

Met Lys Leu Thr Lys Ile Tyr Leu Lys Lys Phe Ser Arg Val Leu Cys
                245                 250                 255

Leu Ala Ile Gly Phe Ala Ser Ala Phe Thr Tyr Ser Tyr Ile Thr Gln
            260                 265                 270

Pro Lys Pro Glu Val Lys Val Val Ser Gln Thr Tyr Asp Phe Asp
        275                 280                 285

Lys Phe Thr Ile Asp Ser Ser Gln Arg Leu Asn Leu Ser Tyr Arg Tyr
    290                 295                 300

Val Phe Lys Asp Ser Lys Gly Lys Leu Ile Asn Ser Asp Asp Leu Gln
305                 310                 315                 320
```

-continued

```
Lys Gln Gly Tyr Ser Ile Thr Tyr Ile Asp Leu Cys Thr Val Ser Ile
                325                 330                 335

Lys Lys Gly Asn Ser Asn Glu Ile Val Lys Cys Asn
            340                 345

<210> SEQ ID NO 14
<211> LENGTH: 426
<212> TYPE: PRT
<213> ORGANISM: Artificial Sequence
<220> FEATURE:
<223> OTHER INFORMATION: Description of Artificial Sequence: gene IV
      protein encoded by phage vector fhag1A (circular)

<400> SEQUENCE: 14

Met Lys Leu Leu Asn Val Ile Asn Phe Val Phe Leu Met Phe Val Ser
 1               5                  10                  15

Ser Ser Ser Phe Ala Gln Val Ile Glu Met Asn Asn Ser Pro Leu Arg
                20                  25                  30

Asp Phe Val Thr Trp Tyr Ser Lys Gln Thr Gly Glu Ser Val Ile Val
            35                  40                  45

Ser Pro Asp Val Lys Gly Thr Val Thr Val Tyr Ser Ser Asp Val Lys
 50                  55                  60

Pro Glu Asn Leu Arg Asn Phe Phe Ile Ser Val Leu Arg Ala Asn Asn
 65                  70                  75                  80

Phe Asp Met Val Gly Ser Ile Pro Ser Ile Ile Gln Lys Tyr Asn Pro
                 85                  90                  95

Asn Ser Gln Asp Tyr Ile Asp Glu Leu Pro Ser Ser Asp Ile Gln Glu
            100                 105                 110

Tyr Asp Asp Asn Ser Ala Pro Ser Gly Gly Phe Phe Val Pro Gln Asn
        115                 120                 125

Asp Asn Val Thr Gln Thr Phe Lys Ile Asn Asn Val Arg Ala Lys Asp
130                 135                 140

Leu Ile Arg Val Val Glu Leu Phe Val Lys Ser Asn Thr Ser Lys Ser
145                 150                 155                 160

Ser Asn Val Leu Ser Val Asp Gly Ser Asn Leu Leu Val Val Ser Ala
                165                 170                 175

Pro Lys Asp Ile Leu Asp Asn Leu Pro Gln Phe Leu Ser Thr Val Asp
            180                 185                 190

Leu Pro Thr Asp Gln Ile Leu Ile Glu Gly Leu Ile Phe Glu Val Gln
        195                 200                 205

Gln Gly Asp Ala Leu Asp Phe Ser Phe Ala Ala Gly Ser Gln Arg Gly
    210                 215                 220

Thr Val Ala Gly Gly Val Asn Thr Asp Arg Leu Thr Ser Val Leu Ser
225                 230                 235                 240

Ser Ala Gly Gly Ser Phe Gly Ile Phe Asn Gly Asp Val Leu Gly Leu
                245                 250                 255

Ser Val Arg Ala Leu Lys Thr Asn Ser His Ser Lys Ile Leu Ser Val
            260                 265                 270

Pro Arg Ile Leu Thr Leu Ser Gly Gln Lys Gly Ser Ile Ser Val Gly
        275                 280                 285

Gln Asn Val Pro Phe Ile Thr Gly Arg Val Thr Gly Glu Ser Ala Asn
    290                 295                 300

Val Asn Asn Pro Phe Gln Thr Val Glu Arg Gln Asn Val Gly Ile Ser
305                 310                 315                 320

Met Ser Val Phe Pro Val Ala Met Ala Gly Gly Asn Ile Val Leu Asp
                325                 330                 335
```

-continued

```
Ile Thr Ser Lys Ala Asp Ser Leu Ser Ser Thr Gln Ala Ser Asp
            340                 345                 350

Val Ile Thr Asn Gln Arg Ser Ile Ala Thr Thr Val Asn Leu Arg Asp
        355                 360                 365

Gly Gln Thr Leu Leu Gly Gly Leu Thr Asp Tyr Lys Asn Thr Ser
    370                 375                 380

Gln Asp Ser Gly Val Pro Phe Leu Ser Lys Ile Pro Leu Ile Gly Leu
385                 390                 395                 400

Leu Phe Ser Ser Arg Ser Asp Ser Asn Glu Glu Ser Thr Leu Tyr Val
                405                 410                 415

Leu Val Lys Ala Thr Ile Val Arg Ala Leu
            420                 425
```

<210> SEQ ID NO 15
<211> LENGTH: 134
<212> TYPE: PRT
<213> ORGANISM: Artificial Sequence
<220> FEATURE:
<223> OTHER INFORMATION: Description of Artificial Sequence: N-terminus
      of gene II protein encoded by phage vector fhag1A (circular)

<400> SEQUENCE: 15

```
Met Ile Asp Met Leu Val Leu Arg Leu Pro Phe Ile Asp Ser Leu Val
  1               5                  10                  15

Cys Ser Arg Leu Ser Gly Asn Asp Leu Ile Ala Phe Val Asp Leu Ser
                20                  25                  30

Lys Ile Ala Thr Leu Ser Gly Met Asn Leu Ser Ala Arg Thr Val Glu
            35                  40                  45

Tyr His Ile Asp Gly Asp Leu Thr Val Ser Gly Leu Ser His Pro Phe
        50                  55                  60

Glu Ser Leu Pro Thr His Tyr Ser Gly Ile Ala Phe Lys Ile Tyr Glu
 65                  70                  75                  80

Gly Ser Lys Asn Phe Tyr Pro Cys Val Glu Ile Lys Ala Ser Pro Ala
                85                  90                  95

Lys Val Leu Gln Gly His Asn Val Phe Gly Thr Thr Asp Leu Ala Leu
                100                 105                 110

Cys Ser Glu Ala Leu Leu Leu Asn Phe Ala Asn Ser Leu Pro Cys Leu
            115                 120                 125

Tyr Asp Leu Leu Asp Val
        130
```

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: primer gIII
      short(for)

<400> SEQUENCE: 16
gcttccggag aattcaatgc tggcggcggc tct                          33

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence: primer gIII
      short(rev)

<400> SEQUENCE: 17
cccccccaag cttatcaaga ctccttatta cg        32

<210> SEQ ID NO 18
<211> LENGTH: 7055
<212> TYPE: DNA
<213> ORGANISM: Artificial Sequence
<220> FEATURE:
<223> OTHER INFORMATION: Description of Artificial Sequence: phage
      vector fhag1A and fjun_1B (circular)
<220> FEATURE:
<221> NAME/KEY: gene
<222> LOCATION: (1)..(828)
<223> OTHER INFORMATION: C-terminus gene II
<220> FEATURE:
<221> NAME/KEY: gene
<222> LOCATION: (496)..(828)
<223> OTHER INFORMATION: gene X
<220> FEATURE:
<221> NAME/KEY: gene
<222> LOCATION: (843)..(1103)
<223> OTHER INFORMATION: gene V
<220> FEATURE:
<221> NAME/KEY: gene
<222> LOCATION: (1108)..(1206)
<223> OTHER INFORMATION: gene VII
<220> FEATURE:
<221> NAME/KEY: gene
<222> LOCATION: (1206)..(1313)
<223> OTHER INFORMATION: gene IX
<220> FEATURE:
<221> NAME/KEY: gene
<222> LOCATION: (1301)..(1519)
<223> OTHER INFORMATION: gene VIII
<220> FEATURE:
<221> NAME/KEY: gene
<222> LOCATION: (1301)..(1519)
<223> OTHER INFORMATION: gene VIII
<220> FEATURE:
<221> NAME/KEY: gene
<222> LOCATION: (1643)..(2302)
<223> OTHER INFORMATION: cat resistance gene
<220> FEATURE:
<221> NAME/KEY: gene
<222> LOCATION: (2607)..(3404)
<223> OTHER INFORMATION: ompA-FLAG-jun-gene IIIc
<220> FEATURE:
<221> NAME/KEY: misc_feature
<222> LOCATION: (2607)..(2669)
<223> OTHER INFORMATION: ompA signal sequence
<220> FEATURE:
<221> NAME/KEY: misc_feature
<222> LOCATION: (2670)..(2681)
<223> OTHER INFORMATION: FLAG peptide
<220> FEATURE:
<221> NAME/KEY: misc_feature
<222> LOCATION: (2697)..(2816)
<223> OTHER INFORMATION: jun peptide
<220> FEATURE:
<221> NAME/KEY: misc_feature
<222> LOCATION: (2832)..(3404)
<223> OTHER INFORMATION: gene III C-terminal domain
<220> FEATURE:
<221> NAME/KEY: gene
<222> LOCATION: (3503)..(3838)
<223> OTHER INFORMATION: gene VI
<220> FEATURE:
<221> NAME/KEY: gene
<222> LOCATION: (3844)..(4887)
<223> OTHER INFORMATION: gene I
<220> FEATURE:
<221> NAME/KEY: gene
<222> LOCATION: (4868)..(6145)
<223> OTHER INFORMATION: gene IV

```
<220> FEATURE:
<221> NAME/KEY: gene
<222> LOCATION: (6654)..(7055)
<223> OTHER INFORMATION: N-terminus gene II
<220> FEATURE:
<221> NAME/KEY: -10_signal
<222> LOCATION: (2517)..(2521)
<220> FEATURE:
<221> NAME/KEY: -35_signal
<222> LOCATION: (2494)..(2498)
<220> FEATURE:
<221> NAME/KEY: misc_feature
<222> LOCATION: (2522)..(2556)
<223> OTHER INFORMATION: lac operator
<220> FEATURE:
<221> NAME/KEY: misc_signal
<222> LOCATION: (6146)..(6224)
<223> OTHER INFORMATION: packaging signal
<220> FEATURE:
<221> NAME/KEY: rep_origin
<222> LOCATION: (6264)..(6409)
<223> OTHER INFORMATION: fd ori
<220> FEATURE:
<221> NAME/KEY: terminator
<222> LOCATION: (3446)..(3488)
<223> OTHER INFORMATION: fd terminator
<220> FEATURE:
<221> NAME/KEY: modified_base
<222> LOCATION: (1550)..(1553)
<223> OTHER INFORMATION: a, t, c, g, other or unknown

<400> SEQUENCE: 18
aacgctacta ccattagtag aattgatgcc accttttcag ctcgcgcccc aaatgaaaat      60
atagctaaac aggttattga ccatttgcga atgtatcta atggtcaaac taaatctact     120
cgttcgcaga attgggaatc aactgttaca tggaatgaaa cttccagaca ccgtacttta    180
gttgcatatt taaaacatgt tgaactacag caccagattc agcaattaag ctctaagcca    240
tccgcaaaaa tgacctctta tcaaaaggag caattaaagg tactgtctaa tcctgacctg    300
ttggaatttg cttccggtct ggttcgcttt gaggctcgaa ttgaaacgcg atatttgaag    360
tctttcgggc ttcctcttaa tcttttgat gcaattcgct ttgcttctga ctataatga     420 cagggtaaag acctgatttt tgattatgg tcattctcgt tttctgaact gtttaaagca    480 tttgagggg attcaatgaa tatttatgac gattccgcag tattggacgc tatccagtct    540 aaacattta caattacccc ctctggcaaa acttcctttg caaagcctc tcgctatttt    600 ggtttctatc gtcgtctggt aatgagggt tatgatagtg ttgctcttac catgcctcgt    660 aattccttt ggcgttatgt atctgcatta gttgagtgtg gtattcctaa atctcaattg    720
atgaatcttt ccacctgtaa taatgttgtt ccgttagttc gttttattaa cgtagatttt    780
tcctcccaac gtcctgactg gtataatgag ccagttctta aaatcgcata aggtaattca    840
aaatgattaa agttgaaatt aaaccgtctc aagcgcaatt tactacccgt tctggtgttt    900
ctcgtcaggg caagccttat tcactgaatg agcagctttg ttacgttgat ttgggtaatg    960
aatatccggt gcttgtcaag attactctcg acgaaggtca gccagcgtat gcgcctggtc   1020
tgtacaccgt gcatctgtcc tcgttcaaag ttggtcagtt cggttctctt atgattgacc   1080
gtctgcgcct cgttccggct aagtaacatg gagcaggtcg cggatttcga cacaatttat   1140
caggcgatga tacaaatctc cgttgtactt tgtttcgcgc ttggtataat cgctgggggt   1200
caaagatgag tgttttagtg tattcttcg cctctttcgt tttaggttgg tgccttcgta    1260
gtggcattac gtatttacc cgtttaatgg aaacttcctc atgcgtaagt ctttagtcct   1320
caaagcctcc gtagccgttg ctaccctcgt tccgatgctg tctttcgctg ctgagggtga   1380
```

```
cgatcccgca aaagcggcct ttgactccct gcaagcctca gcgaccgaat atatcggtta    1440
tgcgtgggcg atggttgttg tcattgtcgg cgcaactatc ggtatcaagc tgtttaagaa    1500
attcacctcg aaagcaagct gataaaggag gtttctcgat cgagacgttn nnngaggttc    1560
caactttcac cataatgaaa taagatcact accgggcgta ttttttgagt tatcgagatt    1620
ttcaggagct aaggaagcta aaatggagaa aaaaatcact ggatatacca ccgttgatat    1680
atcccaatgg catcgtaaag aacattttga ggcatttcag tcagttgctc aatgtaccta    1740
taaccagacc gttcagctgg atattacggc cttttttaaag accgtaaaga aaaataagca    1800 caagtttttat ccggccttta ttcacattct tgcccgcctg atgaatgctc atccggagtt    1860
ccgtatggca atgaaagacg gtgagctggt gatatgggat agtgttcacc cttgttacac    1920
cgttttccat gagcaaactg aaacgttttc atcgctctgg agtgaatacc acgacgattt    1980
ccggcagttt ctacacatat attcgcaaga tgtggcgtgt tacggtgaaa acctggccta    2040
tttccctaaa gggtttattg agaatatgtt tttcgtctca gccaatccct gggtgagttt    2100
caccagtttt gatttaaacg tagccaatat ggacaacttc ttcgccccg ttttcactat    2160 gggcaaatat tatacgcaag cgacaaggt gctgatgccg ctggcgattc aggttcatca    2220
tgccgtttgt gatggcttcc atgtcggcag aatgcttaat gaattacaac agtactgcga    2280
tgagtggcag ggcggggcgt aattttttta aggcagttat tggtgccctt aaacgcctgg    2340
tgctagcctg aggccagttt gctcaggctc tccccgtgga ggtaataatt gctcgaccga    2400
taaaagcggc ttcctgacag gaggccgttt tgttttgcag cccacctcaa cgcaattaat    2460
gtgagttagc tcactcatta ggcaccccag gctttacact ttatgcttcc ggctcgtatg    2520
ttgtgtggaa ttgtgagcgg ataacaattt cacacaggaa acagctatga ccatgattac    2580
gaatttctag ataacgaggg caaaaaatga aaagacagc tatcgcgatt gcagtggcac    2640
tggctggttt cgctaccgta gcgcaggccg actacaaaga tgtcgacgcc ggtggtcgga    2700
tcgcccggct agaggaaaaa gtgaaaacct tgaaagcgca aaactccgag ctggcgtcca    2760
cggccaacat gctcagggaa caggtggcac agcttaaaca gaaagtcatg aaccacggtg    2820
gtgccgaatt caatgctggc ggcggctctg gtggtggttc tggtggcggc tctgagggtg    2880
gtggctctga gggtggcggt tctgagggtg gcggctctga gggaggcggt tccggtggtg    2940
gctctggttc cggtgatttt gattatgaaa agatggcaaa cgctaataag ggggctatga    3000
ccgaaaatgc cgatgaaaac gcgctacagt ctgacgctaa aggcaaactt gattctgtcg    3060
ctactgatta cggtgctgct atcgatggtt tcattggtga cgtttccggc cttgctaatg    3120
gtaatggtgc tactggtgat tttgctggct ctaattccca aatggctcaa gtcggtgacg    3180
gtgataattc acctttaatg aataatttcc gtcaatattt accttccctc cctcaatcgg    3240
ttgaatgtcg cccttttgtc tttagcgctg gtaaaccata tgaattttct attgattgtg    3300
acaaaataaa cttattccgt ggtgtctttg cgtttctttt atatgttgcc acctttatgt    3360 atgtatttc tacgtttgct aacatactgc gtaataagga gtcttgataa gcttcgagaa    3420
attcacctcg aaagcaagct gataaaccga tacaattaaa ggctccttttt ggagcctttt    3480 ttttggaga attaattcaa tcatgccagt tcttttgggt attccgttat tattgcgttt    3540
cctcggtttc cttctggtaa ctttgttcgg ctatctgctt acttttcctta aaagggctt    3600 cggtaagata gctattgcta tttcattgtt tcttgctctt attattgggc ttaactcaat    3660
tcttgtgggt tatctctctg atattagcgc acaattaccc tctgattttg ttcagggcgt    3720
tcagttaatt ctcccgtcta atgcgcttcc ctgttttat gttattctct ctgtaaaggc    3780
```

```
tgctattttc attttttgacg ttaaacaaaa aatcgtttct tatttggatt gggataaata    3840
aatatggctg tttattttgt aactggcaaa ttaggctctg gaaagacgct cgttagcgtt    3900
ggtaagattc aggataaaat tgtagctggg tgcaaaatag caactaatct tgatttaagg    3960
cttcaaaacc tcccgcaagt cgggaggttc gctaaaacgc ctcgcgttct tagaataccg    4020
gataagcctt ctatttctga tttgcttgct attggtcgtg gtaatgattc ctacgacgaa    4080
aataaaaacg gtttgcttgt tcttgatgaa tgcggtactt ggtttaatac ccgttcatgg    4140
aatgacaagg aaagacagcc gattattgat tggtttcttc atgctcgtaa attgggatgg    4200
gatattattt ttcttgttca ggatttatct attgttgata acaggcgcg ttctgcatta    4260 gctgaacacg ttgtttattg tcgccgtctg gacagaatta ctttacccct tgtcggcact    4320
ttatattctc ttgttactgg ctcaaaaatg cctctgccta aattacatgt tggtgttgtt    4380
aaatatggtg attctcaatt aagccctact gttgagcgtt ggctttatac tggtaagaat    4440
ttatataacg catatgacac taaacaggct ttttccagta attatgattc aggtgtttat    4500
tcatatttaa ccccttattt atcacacggt cggtatttca aaccattaaa tttaggtcag    4560
aagatgaaat taactaaaat atatttgaaa agtttttctc gcgttctttg tcttgcgata    4620
ggatttgcat cagcatttac atatagttat ataacccaac ctaagccgga ggttaaaaag    4680
gtagtctctc agacctatga ttttgataaa ttcactattg actcttctca gcgtcttaat    4740
ctaagctatc gctatgtttt caaggattct aagggaaaat taattaatag cgacgattta    4800
cagaagcaag gttattccat cacatatatt gatttatgta ctgtttcaat taaaaaaggt    4860
aattcaaatg aaattgttaa atgtaattaa ttttgttttc ttgatgtttg tttcatcatc    4920
ttcttttgct caagtaattg aaatgaataa ttcgcctctg cgcgatttcg tgacttggta    4980
ttcaaagcaa acaggtgaat ctgttattgt ctcacctgat gttaaaggta cagtgactgt    5040
atattcctct gacgttaagc ctgaaaaattt acgcaatttc tttatctctg ttttacgtgc    5100
taataatttt gatatggttg gctcaattcc ttccataatt cagaaatata acccaaatag    5160
tcaggattat attgatgaat tgccatcatc tgatattcag gaatatgatg ataattccgc    5220
tccttctggt ggtttctttg ttccgcaaaa tgataatgtt actcaaacat ttaaaattaa    5280
taacgttcgc gcaaaggatt aataagggt tgtagaattg tttgttaaat ctaatacatc    5340
taaatcctca aatgtattat ctgttgatgg ttctaactta ttagtagtta gcgcccctaa    5400
agatatttta gataaccttc gcaatttct ttctactgtt gatttgccaa ctgaccagat    5460
attgattgaa ggattaattt tcgaggttca gcaaggtgat gctttagatt tttcctttgc    5520
tgctggctct cagcgcggca ctgttgctgg tggtgttaat actgaccgtc taacctctgt    5580
tttatcttct gcgggtggtt cgttcggtat ttttaacggc gatgttttag ggctatcagt    5640
tcgcgcatta aagactaata gccattcaaa atattgtct gtgcctcgta ttcttacgct    5700
ttcaggtcag aagggttcta tttctgttgg ccagaatgtc cctttttatta ctggtcgtgt    5760 aactggtgaa tctgccaatg taaataatcc atttcagacg ttgagcgtc aaaatgttgg    5820 tatttctatg agtgtttttc ccgttgcaat ggctggcggt aatattgttt tagatataac    5880
cagtaaggcc gatagtttga gttcttctac tcaggcaagt gatgttatta ctaatcaaag    5940
aagtattgcg acaacggtta atttgcgtga tggtcagact cttttgctcg gtggcctcac    6000
tgattacaaa aacacttctc aagattctgg tgtgccgttc ctgtctaaaa tccctttaat    6060
cggcctcctg tttagctccc gttctgattc taacgaggaa agcacgttgt acgtgctcgt    6120
caaagcaacc atagtacgcg ccctgtagcg gcgcattaag cgcggcgggt gtggtggtta    6180
```

```
cgcgcagcgt gaccgctaca cttgccagcg ccctagcgcc cgctcctttc gctttcttcc    6240
cttcctttct cgccacgttc tccggctttc cccgtcaagc tctaaatcgg gggatccctt    6300
tagggttccg atttagtgct ttacggcacc tcgacctcca aaaacttgat ttgggtgatg    6360
gttcacgtag tgggccatcg ccctgataga cggttttcg cccttgacg ttggagtcca     6420 cgttctttaa tagtggactc ttgttccaaa ctggaacaac actcacaact aactcggcct    6480
attcttttga ttatatagga ttttgtcat tttctgctta ctggttaaaa ataagctga      6540 tttaacaaat atttaacgcg aaatttaaca aaacattaac gtttacaatt taaatatttg    6600
cttatacaat catcctgttt tgggctttt tctgattatc aaccggggta catatgattg     6660
acatgctagt tttacgatta ccgttcatcg attctcttgt ttgctccaga ctttcaggta    6720
atgacctgat agcctttgta gacctctcaa aaatagctac cctctccggc atgaattat     6780 cagctagaac ggttgaatat catattgacg gtgatttgac tgtctccggc ctttctcacc    6840
cgtttgaatc tttgcctact cattactccg gcattgcatt taaaatatat gagggttcta    6900 aaaatttta tccctgcgtt gaattaagg cttcaccagc aaaagtatta cagggtcata      6960
atgtttttgg tacaaccgat ttagctttat gctctgaggc tttattgctt aatttttgcta   7020 actctctgcc ttgcttgtac gatttattgg atgtt                               7055
```

<210> SEQ ID NO 19
<211> LENGTH: 276
<212> TYPE: PRT
<213> ORGANISM: Artificial Sequence
<220> FEATURE:
<223> OTHER INFORMATION: Description of Artificial Sequence: C-terminus
      of gene II protein encoded by phage vector fjun_1B (circular)

<400> SEQUENCE: 19

```
Asn Ala Thr Thr Ile Ser Arg Ile Asp Ala Thr Phe Ser Ala Arg Ala
  1               5                  10                  15

Pro Asn Glu Asn Ile Ala Lys Gln Val Ile Asp His Leu Arg Asn Val
             20                  25                  30

Ser Asn Gly Gln Thr Lys Ser Thr Arg Ser Gln Asn Trp Glu Ser Thr
         35                  40                  45

Val Thr Trp Asn Glu Thr Ser Arg His Arg Thr Leu Val Ala Tyr Leu
     50                  55                  60

Lys His Val Glu Leu Gln His Gln Ile Gln Gln Leu Ser Ser Lys Pro
 65                  70                  75                  80

Ser Ala Lys Met Thr Ser Tyr Gln Lys Glu Gln Leu Lys Val Leu Ser
                 85                  90                  95

Asn Pro Asp Leu Leu Glu Phe Ala Ser Gly Leu Val Arg Phe Glu Ala
            100                 105                 110

Arg Ile Glu Thr Arg Tyr Leu Lys Ser Phe Gly Leu Pro Leu Asn Leu
        115                 120                 125

Phe Asp Ala Ile Arg Phe Ala Ser Asp Tyr Asn Arg Gln Gly Lys Asp
    130                 135                 140

Leu Ile Phe Asp Leu Trp Ser Phe Ser Phe Ser Glu Leu Phe Lys Ala
145                 150                 155                 160

Phe Glu Gly Asp Ser Met Asn Ile Tyr Asp Asp Ser Ala Val Leu Asp
                165                 170                 175

Ala Ile Gln Ser Lys His Phe Thr Ile Thr Pro Ser Gly Lys Thr Ser
            180                 185                 190

Phe Ala Lys Ala Ser Arg Tyr Phe Gly Phe Tyr Arg Arg Leu Val Asn
        195                 200                 205
```

-continued

```
Glu Gly Tyr Asp Ser Val Ala Leu Thr Met Pro Arg Asn Ser Phe Trp
        210                 215                 220
Arg Tyr Val Ser Ala Leu Val Glu Cys Gly Ile Pro Lys Ser Gln Leu
225                 230                 235                 240
Met Asn Leu Ser Thr Cys Asn Asn Val Val Pro Leu Val Arg Phe Ile
                245                 250                 255
Asn Val Asp Phe Ser Ser Gln Arg Pro Asp Trp Tyr Asn Glu Pro Val
            260                 265                 270
Leu Lys Ile Ala
        275
```

<210> SEQ ID NO 20
<211> LENGTH: 111
<212> TYPE: PRT
<213> ORGANISM: Artificial Sequence
<220> FEATURE:
<223> OTHER INFORMATION: Description of Artificial Sequence: gene X
     protein encoded by phage vector fjun_1B (circular)

<400> SEQUENCE: 20

```
Met Asn Ile Tyr Asp Asp Ser Ala Val Leu Asp Ala Ile Gln Ser Lys
  1               5                  10                  15
His Phe Thr Ile Thr Pro Ser Gly Lys Thr Ser Phe Ala Lys Ala Ser
                 20                  25                  30
Arg Tyr Phe Gly Phe Tyr Arg Arg Leu Val Asn Glu Gly Tyr Asp Ser
             35                  40                  45
Val Ala Leu Thr Met Pro Arg Asn Ser Phe Trp Arg Tyr Val Ser Ala
         50                  55                  60
Leu Val Glu Cys Gly Ile Pro Lys Ser Gln Leu Met Asn Leu Ser Thr
 65                  70                  75                  80
Cys Asn Asn Val Val Pro Leu Val Arg Phe Ile Asn Val Asp Phe Ser
                 85                  90                  95
Ser Gln Arg Pro Asp Trp Tyr Asn Glu Pro Val Leu Lys Ile Ala
            100                 105                 110
```

<210> SEQ ID NO 21
<211> LENGTH: 87
<212> TYPE: PRT
<213> ORGANISM: Artificial Sequence
<220> FEATURE:
<223> OTHER INFORMATION: Description of Artificial Sequence: gene V
     protein encoded by phage vector fjun_1B (circular)

<400> SEQUENCE: 21

```
Met Ile Lys Val Glu Ile Lys Pro Ser Gln Ala Gln Phe Thr Thr Arg
  1               5                  10                  15
Ser Gly Val Ser Arg Gln Gly Lys Pro Tyr Ser Leu Asn Glu Gln Leu
                 20                  25                  30
Cys Tyr Val Asp Leu Gly Asn Glu Tyr Pro Val Leu Val Lys Ile Thr
             35                  40                  45
Leu Asp Glu Gly Gln Pro Ala Tyr Ala Pro Gly Leu Tyr Thr Val His
         50                  55                  60
Leu Ser Ser Phe Lys Val Gly Gln Phe Gly Ser Leu Met Ile Asp Arg
 65                  70                  75                  80
Leu Arg Leu Val Pro Ala Lys
                 85
```

```
<210> SEQ ID NO 22
<211> LENGTH: 33
<212> TYPE: PRT
<213> ORGANISM: Artificial Sequence
<220> FEATURE:
<223> OTHER INFORMATION: Description of Artificial Sequence: gene VII
      protein encoded by phage vector fjun_1B (circular)

<400> SEQUENCE: 22
```

Met Gln Val Ala Asp Phe Asp Thr Ile Tyr Gln Ala Met Ile Gln
 1               5                  10                  15

Ile Ser Val Val Leu Cys Phe Ala Leu Gly Ile Ile Ala Gly Gly Gln
            20                  25                  30

Arg

```
<210> SEQ ID NO 23
<211> LENGTH: 36
<212> TYPE: PRT
<213> ORGANISM: Artificial Sequence
<220> FEATURE:
<223> OTHER INFORMATION: Description of Artificial Sequence: gene IX
      protein encoded by phage vector fjun_1B (circular)

<400> SEQUENCE: 23
```

Met Ser Val Leu Val Tyr Ser Phe Ala Ser Phe Val Leu Gly Trp Cys
 1               5                  10                  15

Leu Arg Ser Gly Ile Thr Tyr Phe Thr Arg Leu Met Glu Thr Ser Ser
            20                  25                  30

Cys Val Ser Leu
        35

```
<210> SEQ ID NO 24
<211> LENGTH: 73
<212> TYPE: PRT
<213> ORGANISM: Artificial Sequence
<220> FEATURE:
<223> OTHER INFORMATION: Description of Artificial Sequence: gene VIII
      protein encoded by phage vector fjun_1B (circular)

<400> SEQUENCE: 24
```

Met Arg Lys Ser Leu Val Leu Lys Ala Ser Val Ala Val Ala Thr Leu
 1               5                  10                  15

Val Pro Met Leu Ser Phe Ala Ala Glu Gly Asp Asp Pro Ala Lys Ala
            20                  25                  30

Ala Phe Asp Ser Leu Gln Ala Ser Ala Thr Glu Tyr Ile Gly Tyr Ala
        35                  40                  45

Trp Ala Met Val Val Val Ile Val Gly Ala Thr Ile Gly Ile Lys Leu
    50                  55                  60

Phe Lys Lys Phe Thr Ser Lys Ala Ser
65                  70

```
<210> SEQ ID NO 25
<211> LENGTH: 219
<212> TYPE: PRT
<213> ORGANISM: Artificial Sequence
<220> FEATURE:
<223> OTHER INFORMATION: Description of Artificial Sequence: cat protein
      encoded by phage vector fjun_1B (circular)
```

<400> SEQUENCE: 25

```
Met Glu Lys Lys Ile Thr Gly Tyr Thr Thr Val Asp Ile Ser Gln Trp
 1               5                  10                  15

His Arg Lys Glu His Phe Glu Ala Phe Gln Ser Val Ala Gln Cys Thr
            20                  25                  30

Tyr Asn Gln Thr Val Gln Leu Asp Ile Thr Ala Phe Leu Lys Thr Val
        35                  40                  45

Lys Lys Asn Lys His Lys Phe Tyr Pro Ala Phe Ile His Ile Leu Ala
    50                  55                  60

Arg Leu Met Asn Ala His Pro Glu Phe Arg Met Ala Met Lys Asp Gly
65                  70                  75                  80

Glu Leu Val Ile Trp Asp Ser Val His Pro Cys Tyr Thr Val Phe His
                85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Met Leu Asn Glu Leu
        195                 200                 205

Gln Gln Tyr Cys Asp Glu Trp Gln Gly Gly Ala
    210                 215
```

<210> SEQ ID NO 26
<211> LENGTH: 266
<212> TYPE: PRT
<213> ORGANISM: Artificial Sequence
<220> FEATURE:
<223> OTHER INFORMATION: Description of Artificial Sequence: ompA-FLAG-
      jun peptide-gene IIIc encoded by phage vector fjun_1B (circular)

<400> SEQUENCE: 26

```
Met Lys Lys Thr Ala Ile Ala Ile Ala Val Ala Leu Ala Gly Phe Ala
 1               5                  10                  15

Thr Val Ala Gln Ala Asp Tyr Lys Asp Val Asp Ala Gly Gly Arg Ile
            20                  25                  30

Ala Arg Leu Glu Glu Lys Val Lys Thr Leu Lys Ala Gln Asn Ser Glu
        35                  40                  45

Leu Ala Ser Thr Ala Asn Met Leu Arg Glu Gln Val Ala Gln Leu Lys
    50                  55                  60

Gln Lys Val Met Asn His Gly Ala Glu Phe Asn Ala Gly Gly Gly
65                  70                  75                  80

Ser Gly Gly Gly Ser Gly Gly Ser Glu Gly Gly Ser Glu Gly
                85                  90                  95

Gly Gly Ser Glu Gly Gly Ser Glu Gly Gly Ser Gly Gly Gly
            100                 105                 110

Ser Gly Ser Gly Asp Phe Asp Tyr Glu Lys Met Ala Asn Ala Asn Lys
        115                 120                 125
```

```
Gly Ala Met Thr Glu Asn Ala Asp Glu Asn Ala Leu Gln Ser Asp Ala
        130                 135                 140

Lys Gly Lys Leu Asp Ser Val Ala Thr Asp Tyr Gly Ala Ala Ile Asp
145                 150                 155                 160

Gly Phe Ile Gly Asp Val Ser Gly Leu Ala Asn Gly Asn Gly Ala Thr
                165                 170                 175

Gly Asp Phe Ala Gly Ser Asn Ser Gln Met Ala Gln Val Gly Asp Gly
            180                 185                 190

Asp Asn Ser Pro Leu Met Asn Asn Phe Arg Gln Tyr Leu Pro Ser Leu
        195                 200                 205

Pro Gln Ser Val Glu Cys Arg Pro Phe Val Phe Ser Ala Gly Lys Pro
210                 215                 220

Tyr Glu Phe Ser Ile Asp Cys Asp Lys Ile Asn Leu Phe Arg Gly Val
225                 230                 235                 240

Phe Ala Phe Leu Leu Tyr Val Ala Thr Phe Met Tyr Val Phe Ser Thr
                245                 250                 255

Phe Ala Asn Ile Leu Arg Asn Lys Glu Ser
            260                 265
```

<210> SEQ ID NO 27
<211> LENGTH: 112
<212> TYPE: PRT
<213> ORGANISM: Artificial Sequence
<220> FEATURE:
<223> OTHER INFORMATION: Description of Artificial Sequence: gene VI
      protein encoded by phage vector fjun_1B (circular)

<400> SEQUENCE: 27

```
Met Pro Val Leu Leu Gly Ile Pro Leu Leu Arg Phe Leu Gly Phe
 1               5                  10                  15

Leu Leu Val Thr Leu Phe Gly Tyr Leu Leu Thr Phe Leu Lys Lys Gly
                20                  25                  30

Phe Gly Lys Ile Ala Ile Ala Ile Ser Leu Phe Leu Ala Leu Ile Ile
            35                  40                  45

Gly Leu Asn Ser Ile Leu Val Gly Tyr Leu Ser Asp Ile Ser Ala Gln
        50                  55                  60

Leu Pro Ser Asp Phe Val Gln Gly Val Gln Leu Ile Leu Pro Ser Asn
65                  70                  75                  80

Ala Leu Pro Cys Phe Tyr Val Ile Leu Ser Val Lys Ala Ala Ile Phe
                85                  90                  95

Ile Phe Asp Val Lys Gln Lys Ile Val Ser Tyr Leu Asp Trp Asp Lys
                100                 105                 110
```

<210> SEQ ID NO 28
<211> LENGTH: 348
<212> TYPE: PRT
<213> ORGANISM: Artificial Sequence
<220> FEATURE:
<223> OTHER INFORMATION: Description of Artificial Sequence: gene I
      protein encoded by phage vector fjun_1B (circular)

<400> SEQUENCE: 28

```
Met Ala Val Tyr Phe Val Thr Gly Lys Leu Gly Ser Gly Lys Thr Leu
 1               5                  10                  15

Val Ser Val Gly Lys Ile Gln Asp Lys Ile Val Ala Gly Cys Lys Ile
                20                  25                  30

Ala Thr Asn Leu Asp Leu Arg Leu Gln Asn Leu Pro Gln Val Gly Arg
            35                  40                  45
```

```
Phe Ala Lys Thr Pro Arg Val Leu Arg Ile Pro Asp Lys Pro Ser Ile
 50                  55                  60

Ser Asp Leu Leu Ala Ile Gly Arg Gly Asn Asp Ser Tyr Asp Glu Asn
 65                  70                  75                  80

Lys Asn Gly Leu Leu Val Leu Asp Glu Cys Gly Thr Trp Phe Asn Thr
                 85                  90                  95

Arg Ser Trp Asn Asp Lys Glu Arg Gln Pro Ile Ile Asp Trp Phe Leu
                100                 105                 110

His Ala Arg Lys Leu Gly Trp Asp Ile Ile Phe Leu Val Gln Asp Leu
                115                 120                 125

Ser Ile Val Asp Lys Gln Ala Arg Ser Ala Leu Ala Glu His Val Val
        130                 135                 140

Tyr Cys Arg Arg Leu Asp Arg Ile Thr Leu Pro Phe Val Gly Thr Leu
145                 150                 155                 160

Tyr Ser Leu Val Thr Gly Ser Lys Met Pro Leu Pro Lys Leu His Val
                165                 170                 175

Gly Val Val Lys Tyr Gly Asp Ser Gln Leu Ser Pro Thr Val Glu Arg
                180                 185                 190

Trp Leu Tyr Thr Gly Lys Asn Leu Tyr Asn Ala Tyr Asp Thr Lys Gln
            195                 200                 205

Ala Phe Ser Ser Asn Tyr Asp Ser Gly Val Tyr Ser Tyr Leu Thr Pro
    210                 215                 220

Tyr Leu Ser His Gly Arg Tyr Phe Lys Pro Leu Asn Leu Gly Gln Lys
225                 230                 235                 240

Met Lys Leu Thr Lys Ile Tyr Leu Lys Lys Phe Ser Arg Val Leu Cys
                245                 250                 255

Leu Ala Ile Gly Phe Ala Ser Ala Phe Thr Tyr Ser Tyr Ile Thr Gln
                260                 265                 270

Pro Lys Pro Glu Val Lys Lys Val Ser Gln Thr Tyr Asp Phe Asp
            275                 280                 285

Lys Phe Thr Ile Asp Ser Ser Gln Arg Leu Asn Leu Ser Tyr Arg Tyr
    290                 295                 300

Val Phe Lys Asp Ser Lys Gly Lys Leu Ile Asn Ser Asp Asp Leu Gln
305                 310                 315                 320

Lys Gln Gly Tyr Ser Ile Thr Tyr Ile Asp Leu Cys Thr Val Ser Ile
                325                 330                 335

Lys Lys Gly Asn Ser Asn Glu Ile Val Lys Cys Asn
                340                 345

<210> SEQ ID NO 29
<211> LENGTH: 426
<212> TYPE: PRT
<213> ORGANISM: Artificial Sequence
<220> FEATURE:
<223> OTHER INFORMATION: Description of Artificial Sequence: gene IV
      protein encoded by phage vector fjun_1B (circular)

<400> SEQUENCE: 29

Met Lys Leu Leu Asn Val Ile Asn Phe Val Phe Leu Met Phe Val Ser
 1               5                  10                  15

Ser Ser Ser Phe Ala Gln Val Ile Glu Met Asn Asn Ser Pro Leu Arg
                20                  25                  30

Asp Phe Val Thr Trp Tyr Ser Lys Gln Thr Gly Glu Ser Val Ile Val
            35                  40                  45

Ser Pro Asp Val Lys Gly Thr Val Thr Val Tyr Ser Ser Asp Val Lys
 50                  55                  60
```

-continued

Pro Glu Asn Leu Arg Asn Phe Phe Ile Ser Val Leu Arg Ala Asn Asn
 65                  70                  75                  80

Phe Asp Met Val Gly Ser Ile Pro Ser Ile Ile Gln Lys Tyr Asn Pro
                 85                  90                  95

Asn Ser Gln Asp Tyr Ile Asp Glu Leu Pro Ser Ser Asp Ile Gln Glu
            100                 105                 110

Tyr Asp Asp Asn Ser Ala Pro Ser Gly Gly Phe Phe Val Pro Gln Asn
        115                 120                 125

Asp Asn Val Thr Gln Thr Phe Lys Ile Asn Asn Val Arg Ala Lys Asp
130                 135                 140

Leu Ile Arg Val Val Glu Leu Phe Val Lys Ser Asn Thr Ser Lys Ser
145                 150                 155                 160

Ser Asn Val Leu Ser Val Asp Gly Ser Asn Leu Leu Val Ser Ala
                165                 170                 175

Pro Lys Asp Ile Leu Asp Asn Leu Pro Gln Phe Leu Ser Thr Val Asp
            180                 185                 190

Leu Pro Thr Asp Gln Ile Leu Ile Glu Gly Leu Ile Phe Glu Val Gln
        195                 200                 205

Gln Gly Asp Ala Leu Asp Phe Ser Phe Ala Ala Gly Ser Gln Arg Gly
210                 215                 220

Thr Val Ala Gly Gly Val Asn Thr Asp Arg Leu Thr Ser Val Leu Ser
225                 230                 235                 240

Ser Ala Gly Gly Ser Phe Gly Ile Phe Asn Gly Asp Val Leu Gly Leu
                245                 250                 255

Ser Val Arg Ala Leu Lys Thr Asn Ser His Ser Lys Ile Leu Ser Val
            260                 265                 270

Pro Arg Ile Leu Thr Leu Ser Gly Gln Lys Gly Ser Ile Ser Val Gly
        275                 280                 285

Gln Asn Val Pro Phe Ile Thr Gly Arg Val Thr Gly Glu Ser Ala Asn
290                 295                 300

Val Asn Asn Pro Phe Gln Thr Val Glu Arg Gln Asn Val Gly Ile Ser
305                 310                 315                 320

Met Ser Val Phe Pro Val Ala Met Ala Gly Gly Asn Ile Val Leu Asp
                325                 330                 335

Ile Thr Ser Lys Ala Asp Ser Leu Ser Ser Ser Thr Gln Ala Ser Asp
            340                 345                 350

Val Ile Thr Asn Gln Arg Ser Ile Ala Thr Thr Val Asn Leu Arg Asp
        355                 360                 365

Gly Gln Thr Leu Leu Leu Gly Gly Leu Thr Asp Tyr Lys Asn Thr Ser
370                 375                 380

Gln Asp Ser Gly Val Pro Phe Leu Ser Lys Ile Pro Leu Ile Gly Leu
385                 390                 395                 400

Leu Phe Ser Ser Arg Ser Asp Ser Asn Glu Glu Ser Thr Leu Tyr Val
                405                 410                 415

Leu Val Lys Ala Thr Ile Val Arg Ala Leu
            420                 425

<210> SEQ ID NO 30
<211> LENGTH: 134
<212> TYPE: PRT
<213> ORGANISM: Artificial Sequence
<220> FEATURE:
<223> OTHER INFORMATION: Description of Artificial Sequence: N-terminus
      of gene II protein encoded by phage vector fjun_1B (circular)

<400> SEQUENCE: 30

```
Met Ile Asp Met Leu Val Leu Arg Leu Pro Phe Ile Asp Ser Leu Val
 1               5                  10                  15
Cys Ser Arg Leu Ser Gly Asn Asp Leu Ile Ala Phe Val Asp Leu Ser
             20                  25                  30
Lys Ile Ala Thr Leu Ser Gly Met Asn Leu Ser Ala Arg Thr Val Glu
         35                  40                  45
Tyr His Ile Asp Gly Asp Leu Thr Val Ser Gly Leu Ser His Pro Phe
     50                  55                  60
Glu Ser Leu Pro Thr His Tyr Ser Gly Ile Ala Phe Lys Ile Tyr Glu
 65                  70                  75                  80
Gly Ser Lys Asn Phe Tyr Pro Cys Val Glu Ile Lys Ala Ser Pro Ala
                 85                  90                  95
Lys Val Leu Gln Gly His Asn Val Phe Gly Thr Thr Asp Leu Ala Leu
            100                 105                 110
Cys Ser Glu Ala Leu Leu Leu Asn Phe Ala Asn Ser Leu Pro Cys Leu
        115                 120                 125
Tyr Asp Leu Leu Asp Val
    130
```

<210> SEQ ID NO 31
<211> LENGTH: 6971
<212> TYPE: DNA
<213> ORGANISM: Artificial Sequence
<220> FEATURE:
<223> OTHER INFORMATION: Description of Artificial Sequence: phage
      vector fpep3_1B-IR3seq (circular)
<220> FEATURE:
<221> NAME/KEY: gene
<222> LOCATION: (94)..(429)
<223> OTHER INFORMATION: gene VI
<220> FEATURE:
<221> NAME/KEY: gene
<222> LOCATION: (435)..(1478)
<223> OTHER INFORMATION: gene I
<220> FEATURE:
<221> NAME/KEY: gene
<222> LOCATION: (1459)..(2736)
<223> OTHER INFORMATION: gene IV
<220> FEATURE:
<221> NAME/KEY: gene
<222> LOCATION: (3245)..(4474)
<223> OTHER INFORMATION: gene II
<220> FEATURE:
<221> NAME/KEY: gene
<222> LOCATION: (4142)..(4474)
<223> OTHER INFORMATION: gene X
<220> FEATURE:
<221> NAME/KEY: gene
<222> LOCATION: (4489)..(4749)
<223> OTHER INFORMATION: gene V
<220> FEATURE:
<221> NAME/KEY: gene
<222> LOCATION: (4754)..(4852)
<223> OTHER INFORMATION: gene VII
<220> FEATURE:
<221> NAME/KEY: gene
<222> LOCATION: (4852)..(4959)
<223> OTHER INFORMATION: gene IX
<220> FEATURE:
<221> NAME/KEY: gene
<222> LOCATION: (4947)..(5165)
<223> OTHER INFORMATION: gene VIII
<220> FEATURE:
<221> NAME/KEY: gene
<222> LOCATION: (5289)..(5945)
<223> OTHER INFORMATION: cat resistance gene

```
<220> FEATURE:
<221> NAME/KEY: gene
<222> LOCATION: (6253)..(6969)
<223> OTHER INFORMATION: ompA-FLAG-pep3-gIIIs
<220> FEATURE:
<221> NAME/KEY: misc_feature
<222> LOCATION: (6253)..(6315)
<223> OTHER INFORMATION: ompA signal sequence
<220> FEATURE:
<221> NAME/KEY: misc_feature
<222> LOCATION: (6316)..(6327)
<223> OTHER INFORMATION: FLAG peptide
<220> FEATURE:
<221> NAME/KEY: misc_feature
<222> LOCATION: (6334)..(6372)
<223> OTHER INFORMATION: peptide 3
<220> FEATURE:
<221> NAME/KEY: misc_feature
<222> LOCATION: (6394)..(6969)
<223> OTHER INFORMATION: gene IIIs
<220> FEATURE:
<221> NAME/KEY: -10_signal
<222> LOCATION: (6140)..(6144)
<220> FEATURE:
<221> NAME/KEY: -35_signal
<222> LOCATION: (6163)..(6167)
<220> FEATURE:
<221> NAME/KEY: misc_feature
<222> LOCATION: (6168)..(6202)
<223> OTHER INFORMATION: lac operator
<220> FEATURE:
<221> NAME/KEY: misc_signal
<222> LOCATION: (2737)..(2815)
<223> OTHER INFORMATION: packaging signal
<220> FEATURE:
<221> NAME/KEY: rep_origin
<222> LOCATION: (3033)..(3149)
<223> OTHER INFORMATION: f1 ori
<220> FEATURE:
<221> NAME/KEY: terminator
<222> LOCATION: (49)..(70)
<223> OTHER INFORMATION: fd terminator

<400> SEQUENCE: 31
agcttcgaga aattcacctc gaaagcaagc tgataaaccg atacaattaa aggctccttt        60
tggagccttt ttttttggag aattaattca atcatgccag ttcttttggg tattccgtta       120
ttattgcgtt tcctcggttt ccttctggta actttgttcg gctatctgct tactttcctt       180
aaaaagggct tcggtaagat agctattgct atttcattgt ttcttgctct tattattggg       240
cttaactcaa ttcttgtggg ttatctctct gatattagcg cacaattacc ctctgatttt       300
gttcagggcg ttcagttaat tctcccgtct aatgcgcttc cctgttttta tgttattctc       360
tctgtaaagg ctgctatttt cattttttgac gttaaacaaa aaatcgtttc ttatttggat      420
tgggataaat aaatatggct gtttattttg taactggcaa attaggctct ggaaagacgc       480
tcgttagcgt tggtaagatt caggataaaa ttgtagctgg gtgcaaaata gcaactaatc       540
ttgatttaag gcttcaaaac ctcccgcaag tcgggaggtt cgctaaaacg cctcgcgttc       600
ttagaatacc ggataagcct tctatttctg atttgcttgc tattggtcgt ggtaatgatt       660
cctacgacga aaataaaaac ggtttgcttg ttcttgatga atgcggtact tggtttaata       720
cccgttcatg gaatgacaag gaaagacagc cgattattga ttggtttctt catgctcgta       780
aattgggatg ggatattatt tttcttgttc aggatttatc tattgttgat aaacaggcgc       840
gttctgcatt agctgaacac gttgtttatt gtcgccgtct ggacagaatt actttaccct      900
ttgtcggcac tttatattct cttgttactg gctcaaaaat gcctctgcct aaattacatg      960
ttggtgttgt taaatatggt gattctcaat taagccctac tgttgagcgt tggctttata     1020
```

```
ctggtaagaa tttatataac gcatatgaca ctaaacaggc ttttccagt aattatgatt      1080 caggtgttta ttcatattta accccttatt tatcacacgt tcggtatttc aaaccattaa      1140
atttaggtca gaagatgaaa ttaactaaaa tatatttgaa aaagttttct cgcgttcttt      1200
gtcttgcgat aggatttgca tcagcattta catatagtta tataacccaa cctaagccgg      1260
aggttaaaaa ggtagtctct cagacccatg attttgataa attcactatt gactcttctc      1320
agcgtcttaa tctaagctat cgctatgttt tcaaggattc taagggaaaa ttaattaata      1380
gcgacgattt acagaagcaa ggttattcca tcacatatat tgattatgt actgtttcaa      1440 ttaaaaaagg taattcaaat gaattgtta aatgtaatta attttgtttt cttgatgttt      1500
gtttcatcat cttcttttgc tcaagtaatt gaaatgaata attcgcctct gcgcgatttc      1560
gtgacttggt attcaaagca aacaggtgaa tctgttattg tctcacctga tgttaaaggt      1620
acagtgactg tatattcctc tgacgttaag cctgaaaatt tacgcaattt ctttatctct      1680
gttttacgtg ctaataattt tgatatggtt ggctctaatc cttccataat tcagaaatat      1740
aacccaaata gtcaggatta tattgatgaa ttgccatcat ctgatattca ggaatatgat      1800
gataattccg ctccttctgg tggtttcttt gttccgcaaa atgataatgt tactcaaaca      1860
tttaaaatta ataacgttcg cgcaaaggat ttaataaggg ttgtagaatt gtttgttaaa      1920
tctaatacat ctaaatcctc aaatgtatta tctgttgatg gttctaactt attagtagtt      1980
agcgccccta agatattttt agataacctt ccgcaatttc tttctactgt tgatttgcca      2040
actgaccaga tattgattga aggattaatt ttcgaggttc agcaaggtga tgctttagat      2100
ttttcctttg ctgctggctc tcagcgcggc actgttgctg gtggtgttaa tactgaccgt      2160
ctaacctctg ttttatcttc tgcgggtggt tcgttcggta tttttaacgg cgatgtttta      2220
gggctatcag ttcgcgcatt aaagactaat agccattcaa aaatattgtc tgtgcctcgt      2280
attcttacgc tttcaggtca gaagggttct atttctgttg ccagaatgt ccctttatt      2340 actggtcgtg taactggtga atctgccaat gtaaataatc catttcagac aattgagcgt      2400
caaaatgttg gtatttctat gagtgttttt cccgttgcaa tggctggcgg taatattgtt      2460
ttagatataa ccagtaaggc cgatagtttg agttcttcta ctcaggcaag tgatgttatt      2520
actaatcaaa gaagtattgc gacaacggtt aatttgcgtg atggtcagac tcttttgctc      2580
ggtggcctca ctgattacaa aaacacttct caagattctg gtgtgccgtt cctgtctaaa      2640 atcccttttaa tcggcctcct gtttagctcc cgttctgatt ctaacgagga aagcacgttg      2700
tacgtgctcg tcaaagcaac catagtacgc gccctgtagc ggcgcattaa gcgcggcggg      2760
tgtggtggtt acgcgcagcg tgaccgctac acttgccagc gccctagcgc ccgctccttt      2820
cgctttcttc ccttcctttc tcgccacgtt ctccggcttt cccgtcaag ctctaaatcg      2880 ggggatccct ttagggttcc gatttagtgc tttacggcac ctcgacctcc aaaaacttga      2940
tttgggtgat ggttcacgta gtgggccatc gccctaatag acgttttttc gcctttgac      3000 gttggagtcc acgttcttta atagtggact cttgttccaa actggaacaa cactcaaccc      3060
tatctcggtc tattcttttg atttataagg gattttgccg atttcggcct attggttaaa      3120
aaatgagctg atttaacaaa aatttaacgc gaattttaac aaaatattaa cgtttacaat      3180
ttaaatattt gcttatacaa tcttcctgtt tttgggcttt ttctgattat caaccggggt      3240
acatatgatt gacatgctag ttttacgatt accgttcatc gattctcttg tttgctccag      3300
actctcaggc aatgacctga tagccttttt agacctctca aaaatagcta ccctctccgg      3360
catgaattta tcagctagaa cggttgaata tcatattgat ggtgatttga ctgtctccgg      3420
```

| | | |
|---|---|---|
| cctttctcac | ccgtttgaat ctttacctac acattactca ggcattgcat ttaaaatata | 3480 |
| tgagggttct | aaaaatttt atccttgcgt tgaaataaag gcttctcccg caaaagtatt | 3540 |
| acagggtcat | aatgttttg gtacaaccga tttagcttta tgctctgagg ctttattgct | 3600 |
| taatttgct | aattctttgc cttgcctgta tgatttattg gatgttaacg ctactactat | 3660 |
| tagtagaatt | gatgccacct tttcagctcg cgccccaaat gaaaatatag ctaaacaggt | 3720 |
| tattgaccat | ttgcgaaatg tatctaatgg tcaaactaaa tctactcgtt cgcagaattg | 3780 |
| ggaatcaact | gttacatgga atgaaacttc cagacaccgt actttagttg catatttaaa | 3840 |
| acatgttgag | ctacagcacc agatccagca attaagctct aagccatccg caaaaatgac | 3900 |
| ctcttatcaa | aaggagcaat taaaggtact ctctaatcct gacctgttgg agtttgcttc | 3960 |
| cggtctggtt | cgctttgaag ctcgaattaa aacgcgatat ttgaagtctt tcgggcttcc | 4020 |
| tcttaatctt | tttgatgcaa tccgctttgc ttctgactat aatagtcagg gtaaagacct | 4080 |
| gatttttgat | ttatggtcat tctcgttttc tgaactgttt aaagcatttg aggggggattc | 4140 |
| aatgaatatt | tatgacgatt ccgcagtatt ggacgctatc cagtctaaac attttactat | 4200 |
| tacccctct | ggcaaaactt cttttgcaaa agcctctcgc tattttgtt tttatcgtcg | 4260 |
| tctggtaaac | gagggttatg atagtgttgc tcttactatg cctcgtaatt ccttttggcg | 4320 |
| ttatgtatct | gcattagttg aatgtggtat tcctaaatct caactgatga atctttctac | 4380 |
| ctgtaataat | gttgttccgt tagttcgttt tattaacgta gattttctt cccaacgtcc | 4440 |
| tgactggtat | aatgagccag ttcttaaaat cgcataaggt aattcacaat gattaaagtt | 4500 |
| gaaattaaac | catctcaagc gcaattcact acccgttctg gtgtttctcg tcagggcaag | 4560 |
| ccttattcac | tgaatgagca gctttgttac gttgatttgg gtaatgaata ccggtgctt | 4620 |
| gtcaagatta | ctcttgatga aggtcagcca gcctatgcgc ctggtctgta caccgtgcat | 4680 |
| ctgtcctcgt | tcaaagttgg tcagttcggt tctcttatga ttaccgtct gcgcctcgtt | 4740 |
| ccggctaagt | aacatggagc aggtcgcgga tttcgacaca atttatcagg cgatgataca | 4800 |
| aatctccgtt | gtactttgtt tcgcgcttgg tataatcgct gggggtcaaa gatgagtgtt | 4860 |
| ttagtgtatt | ctttcgcctc tttcgtttta ggttggtgcc ttcgtagtgg cattacgtat | 4920 |
| tttacccgtt | taatggaaac ttcctcatgc gtaagtcttt agtcctcaaa gcctccgtag | 4980 |
| ccgttgctac | cctcgttccg atgctgtctt tcgctgctga gggtgacgat cccgcaaaag | 5040 |
| cggcctttga | ctcccctgcaa gcctcagcga ccgaatatat cggttatgcg tgggcgatgg | 5100 |
| ttgttgtcat | tgtcggcgca actatcggta tcaagctgtt taagaaattc acctcgaaag | 5160 |
| caagctgata | aaggaggttt ctcgatcgag acgttgggtg aggttccaac tttcaccata | 5220 |
| atgaaataag | atcactaccg ggcgtatttt ttgagttatc gagattttca ggagctaagg | 5280 |
| aagctaaaat | ggagaaaaaa atcactggat ataccaccgt tgatatatcc caatggcatc | 5340 |
| gtaaagaaca | ttttgaggca tttcagtcag ttgctcaatg tacctataac cagaccgttc | 5400 |
| agctggatat | tacggccttt ttaaagaccg taaagaaaaa taagcacaag ttttatccgg | 5460 |
| cctttattca | cattcttgcc cgcctgatga atgctcatcc ggagttccgt atggcaatga | 5520 |
| aagacggtga | gctggtgata tgggatagtg ttcacccttg ttacaccgtt ttccatgagc | 5580 |
| aaactgaaac | gttttcatcg ctctggagtg aataccacga cgatttccgg cagtttctac | 5640 |
| acatatattc | gcaagatgtg gcgtgttacg gtgaaaacct ggcctatttc cctaaagggt | 5700 |
| ttattgagaa | tatgtttttc gtctcagcca atccctgggt gagtttcacc agttttgatt | 5760 |
| taaacgtagc | caatatggac aacttcttcg cccccgtttt cactatgggc aaatattata | 5820 |

-continued

```
cgcaaggcga caaggtgctg atgccgctgg cgattcaggt tcatcatgcc gtttgtgatg    5880
gcttccatgt cggcagaatg cttaatgaat acaacagta ctgcgatgag tggcagggcg     5940
gggcgtaatt ttttaaggc agttattggt gcccttaaac gcctggtgct agcctgaggc     6000
cagtttgctc aggctctccc cgtggaggta ataattgctc gaccgataaa agcggcttcc    6060
tgacaggagg ccgttttgtt ttgcagccca cctcaacgca attaatgtga gttagctcac    6120
tcattaggca ccccaggctt tacactttat gcttccggct cgtatgttgt gtggaattgt    6180
gagcggataa caatttcaca caggaaacag ctatgaccat gattacgaat tctagataa     6240 cgagggcaaa aaatgaaaaa gacagctatc gcgattgcag tggcactggc tggtttcgct    6300
accgtagcgc aggccgacta caaagatgtc gactgtattg tttatcatgc tcattatctt    6360
gttgctaagt gtggtggtgg aggatccgaa ttcaatgctg gcggcggctc tggtggtggt    6420
tctggtggcg gctctgaggg tggtggctct gagggtggcg ttctgaggg tggcggctct    6480 gagggaggcg gttccggtgg tggctctggt tccggtgatt ttgattatga aaagatggca    6540
aacgctaata agggggctat gaccgaaaat gccgatgaaa acgcgctaca gtctgacgct    6600
aaaggcaaac ttgattctgt cgctactgat tacggtgctg ctatcgatgg tttcattggt    6660
gacgtttccg gccttgctaa tggtaatggt gctactggtg attttgctgg ctctaattcc    6720
caaatggctc aagtcggtga cggtgataat tcacctttaa tgaataattt ccgtcaatat    6780
ttaccttccc tccctcaatc ggttgaatgt cgccctttg tctttggcgc tggtaaacca    6840
tatgaatttt ctattgattg tgacaaaata aacttattcc gtggtgtctt tgcgtttctt    6900
ttatatgttg ccacctttat gtatgtattt tctacgtttg ctaacatact gcgtaataag    6960
gagtcttgat a                                                          6971
```

<210> SEQ ID NO 32
<211> LENGTH: 112
<212> TYPE: PRT
<213> ORGANISM: Artificial Sequence
<220> FEATURE:
<223> OTHER INFORMATION: Description of Artificial Sequence: gene VI
      protein encoded by phage vector fpep3_1B-IR3seq (circular)

<400> SEQUENCE: 32

```
Met Pro Val Leu Leu Gly Ile Pro Leu Leu Leu Arg Phe Leu Gly Phe
  1               5                  10                  15

Leu Leu Val Thr Leu Phe Gly Tyr Leu Leu Thr Phe Leu Lys Lys Gly
             20                  25                  30

Phe Gly Lys Ile Ala Ile Ala Ile Ser Leu Phe Leu Ala Leu Ile Ile
         35                  40                  45

Gly Leu Asn Ser Ile Leu Val Gly Tyr Leu Ser Asp Ile Ser Ala Gln
     50                  55                  60

Leu Pro Ser Asp Phe Val Gln Gly Val Gln Leu Ile Leu Pro Ser Asn
 65                  70                  75                  80

Ala Leu Pro Cys Phe Tyr Val Ile Leu Ser Val Lys Ala Ala Ile Phe
                 85                  90                  95

Ile Phe Asp Val Lys Gln Lys Ile Val Ser Tyr Leu Asp Trp Asp Lys
                100                 105                 110
```

<210> SEQ ID NO 33
<211> LENGTH: 348
<212> TYPE: PRT
<213> ORGANISM: Artificial Sequence

```
<220> FEATURE:
<223> OTHER INFORMATION: Description of Artificial Sequence: gene I
      protein encoded by phage vector fpep3_1B-IR3seq (circular)

<400> SEQUENCE: 33

Met Ala Val Tyr Phe Val Thr Gly Lys Leu Gly Ser Gly Lys Thr Leu
  1               5                  10                  15

Val Ser Val Gly Lys Ile Gln Asp Lys Ile Val Ala Gly Cys Lys Ile
                 20                  25                  30

Ala Thr Asn Leu Asp Leu Arg Leu Gln Asn Leu Pro Gln Val Gly Arg
             35                  40                  45

Phe Ala Lys Thr Pro Arg Val Leu Arg Ile Pro Asp Lys Pro Ser Ile
 50                  55                  60

Ser Asp Leu Leu Ala Ile Gly Arg Gly Asn Asp Ser Tyr Asp Glu Asn
 65                  70                  75                  80

Lys Asn Gly Leu Leu Val Leu Asp Glu Cys Gly Thr Trp Phe Asn Thr
                 85                  90                  95

Arg Ser Trp Asn Asp Lys Glu Arg Gln Pro Ile Ile Asp Trp Phe Leu
                100                 105                 110

His Ala Arg Lys Leu Gly Trp Asp Ile Ile Phe Leu Val Gln Asp Leu
            115                 120                 125

Ser Ile Val Asp Lys Gln Ala Arg Ser Ala Leu Ala Glu His Val Val
130                 135                 140

Tyr Cys Arg Arg Leu Asp Arg Ile Thr Leu Pro Phe Val Gly Thr Leu
145                 150                 155                 160

Tyr Ser Leu Val Thr Gly Ser Lys Met Pro Leu Pro Lys Leu His Val
                165                 170                 175

Gly Val Val Lys Tyr Gly Asp Ser Gln Leu Ser Pro Thr Val Glu Arg
            180                 185                 190

Trp Leu Tyr Thr Gly Lys Asn Leu Tyr Asn Ala Tyr Asp Thr Lys Gln
            195                 200                 205

Ala Phe Ser Ser Asn Tyr Asp Ser Gly Val Tyr Ser Tyr Leu Thr Pro
210                 215                 220

Tyr Leu Ser His Gly Arg Tyr Phe Lys Pro Leu Asn Leu Gly Gln Lys
225                 230                 235                 240

Met Lys Leu Thr Lys Ile Tyr Leu Lys Lys Phe Ser Arg Val Leu Cys
                245                 250                 255

Leu Ala Ile Gly Phe Ala Ser Ala Phe Thr Tyr Ser Tyr Ile Thr Gln
            260                 265                 270

Pro Lys Pro Glu Val Lys Lys Val Ser Gln Thr Tyr Asp Phe Asp
            275                 280                 285

Lys Phe Thr Ile Asp Ser Ser Gln Arg Leu Asn Leu Ser Tyr Arg Tyr
            290                 295                 300

Val Phe Lys Asp Ser Lys Gly Lys Leu Ile Asn Ser Asp Leu Gln
305                 310                 315                 320

Lys Gln Gly Tyr Ser Ile Thr Tyr Ile Asp Leu Cys Thr Val Ser Ile
                325                 330                 335

Lys Lys Gly Asn Ser Asn Glu Ile Val Lys Cys Asn
            340                 345

<210> SEQ ID NO 34
<211> LENGTH: 426
<212> TYPE: PRT
<213> ORGANISM: Artificial Sequence
```

<220> FEATURE:
<223> OTHER INFORMATION: Description of Artificial Sequence: gene IV
       protein encoded by phage vector fpep3_1B-IR3seq (circular)

<400> SEQUENCE: 34

Met Lys Leu Leu Asn Val Ile Asn Phe Val Phe Leu Met Phe Val Ser
 1               5                  10                  15

Ser Ser Ser Phe Ala Gln Val Ile Glu Met Asn Asn Ser Pro Leu Arg
            20                  25                  30

Asp Phe Val Thr Trp Tyr Ser Lys Gln Thr Gly Glu Ser Val Ile Val
        35                  40                  45

Ser Pro Asp Val Lys Gly Thr Val Thr Val Tyr Ser Ser Asp Val Lys
    50                  55                  60

Pro Glu Asn Leu Arg Asn Phe Ile Ser Val Leu Arg Ala Asn Asn
65                  70                  75                  80

Phe Asp Met Val Gly Ser Asn Pro Ser Ile Ile Gln Lys Tyr Asn Pro
                85                  90                  95

Asn Ser Gln Asp Tyr Ile Asp Glu Leu Pro Ser Ser Asp Ile Gln Glu
            100                 105                 110

Tyr Asp Asp Asn Ser Ala Pro Ser Gly Gly Phe Phe Val Pro Gln Asn
        115                 120                 125

Asp Asn Val Thr Gln Thr Phe Lys Ile Asn Asn Val Arg Ala Lys Asp
130                 135                 140

Leu Ile Arg Val Val Glu Leu Phe Val Lys Ser Asn Thr Ser Lys Ser
145                 150                 155                 160

Ser Asn Val Leu Ser Val Asp Gly Ser Asn Leu Leu Val Val Ser Ala
                165                 170                 175

Pro Lys Asp Ile Leu Asp Asn Leu Pro Gln Phe Leu Ser Thr Val Asp
            180                 185                 190

Leu Pro Thr Asp Gln Ile Leu Ile Glu Gly Leu Ile Phe Glu Val Gln
        195                 200                 205

Gln Gly Asp Ala Leu Asp Phe Ser Phe Ala Ala Gly Ser Gln Arg Gly
    210                 215                 220

Thr Val Ala Gly Gly Val Asn Thr Asp Arg Leu Thr Ser Val Leu Ser
225                 230                 235                 240

Ser Ala Gly Gly Ser Phe Gly Ile Phe Asn Gly Asp Val Leu Gly Leu
                245                 250                 255

Ser Val Arg Ala Leu Lys Thr Asn Ser His Ser Lys Ile Leu Ser Val
            260                 265                 270

Pro Arg Ile Leu Thr Leu Ser Gly Gln Lys Gly Ser Ile Ser Val Gly
        275                 280                 285

Gln Asn Val Pro Phe Ile Thr Gly Arg Val Thr Gly Glu Ser Ala Asn
    290                 295                 300

Val Asn Asn Pro Phe Gln Thr Ile Glu Arg Gln Asn Val Gly Ile Ser
305                 310                 315                 320

Met Ser Val Phe Pro Val Ala Met Ala Gly Gly Asn Ile Val Leu Asp
                325                 330                 335

Ile Thr Ser Lys Ala Asp Ser Leu Ser Ser Thr Gln Ala Ser Asp
            340                 345                 350

Val Ile Thr Asn Gln Arg Ser Ile Ala Thr Thr Val Asn Leu Arg Asp
        355                 360                 365

Gly Gln Thr Leu Leu Leu Gly Gly Leu Thr Asp Tyr Lys Asn Thr Ser
    370                 375                 380

```
Gln Asp Ser Gly Val Pro Phe Leu Ser Lys Ile Pro Leu Ile Gly Leu
385                 390                 395                 400

Leu Phe Ser Ser Arg Ser Asp Ser Asn Glu Glu Ser Thr Leu Tyr Val
                405                 410                 415

Leu Val Lys Ala Thr Ile Val Arg Ala Leu
            420                 425

<210> SEQ ID NO 35
<211> LENGTH: 410
<212> TYPE: PRT
<213> ORGANISM: Artificial Sequence
<220> FEATURE:
<223> OTHER INFORMATION: Description of Artificial Sequence: gene II
      protein encoded by phage vector fpep3_1B-IR3seq (circular)

<400> SEQUENCE: 35

Met Ile Asp Met Leu Val Leu Arg Leu Pro Phe Ile Asp Ser Leu Val
1               5                   10                  15

Cys Ser Arg Leu Ser Gly Asn Asp Leu Ile Ala Phe Leu Asp Leu Ser
            20                  25                  30

Lys Ile Ala Thr Leu Ser Gly Met Asn Leu Ser Ala Arg Thr Val Glu
        35                  40                  45

Tyr His Ile Asp Gly Asp Leu Thr Val Ser Gly Leu Ser His Pro Phe
    50                  55                  60

Glu Ser Leu Pro Thr His Tyr Ser Gly Ile Ala Phe Lys Ile Tyr Glu
65                  70                  75                  80

Gly Ser Lys Asn Phe Tyr Pro Cys Val Glu Ile Lys Ala Ser Pro Ala
                85                  90                  95

Lys Val Leu Gln Gly His Asn Val Phe Gly Thr Thr Asp Leu Ala Leu
            100                 105                 110

Cys Ser Glu Ala Leu Leu Leu Asn Phe Ala Asn Ser Leu Pro Cys Leu
        115                 120                 125

Tyr Asp Leu Leu Asp Val Asn Ala Thr Thr Ile Ser Arg Ile Asp Ala
    130                 135                 140

Thr Phe Ser Ala Arg Ala Pro Asn Glu Asn Ile Ala Lys Gln Val Ile
145                 150                 155                 160

Asp His Leu Arg Asn Val Ser Asn Gly Gln Thr Lys Ser Thr Arg Ser
                165                 170                 175

Gln Asn Trp Glu Ser Thr Val Thr Trp Asn Glu Thr Ser Arg His Arg
            180                 185                 190

Thr Leu Val Ala Tyr Leu Lys His Val Glu Leu Gln His Gln Ile Gln
    195                 200                 205

Gln Leu Ser Ser Lys Pro Ser Ala Lys Met Thr Ser Tyr Gln Lys Glu
    210                 215                 220

Gln Leu Lys Val Leu Ser Asn Pro Asp Leu Leu Glu Phe Ala Ser Gly
225                 230                 235                 240

Leu Val Arg Phe Glu Ala Arg Ile Lys Thr Arg Tyr Leu Lys Ser Phe
                245                 250                 255

Gly Leu Pro Leu Asn Leu Phe Asp Ala Ile Arg Phe Ala Ser Asp Tyr
            260                 265                 270

Asn Ser Gln Gly Lys Asp Leu Ile Phe Asp Leu Trp Ser Phe Ser Phe
    275                 280                 285

Ser Glu Leu Phe Lys Ala Phe Glu Gly Asp Ser Met Asn Ile Tyr Asp
    290                 295                 300

Asp Ser Ala Val Leu Asp Ala Ile Gln Ser Lys His Phe Thr Ile Thr
305                 310                 315                 320
```

-continued

```
Pro Ser Gly Lys Thr Ser Phe Ala Lys Ala Ser Arg Tyr Phe Cys Phe
                325                 330                 335

Tyr Arg Arg Leu Val Asn Glu Gly Tyr Asp Ser Val Ala Leu Thr Met
            340                 345                 350

Pro Arg Asn Ser Phe Trp Arg Tyr Val Ser Ala Leu Val Glu Cys Gly
                355                 360                 365

Ile Pro Lys Ser Gln Leu Met Asn Leu Ser Thr Cys Asn Asn Val Val
370                 375                 380

Pro Leu Val Arg Phe Ile Asn Val Asp Phe Ser Ser Gln Arg Pro Asp
385                 390                 395                 400

Trp Tyr Asn Glu Pro Val Leu Lys Ile Ala
                405                 410
```

<210> SEQ ID NO 36
<211> LENGTH: 111
<212> TYPE: PRT
<213> ORGANISM: Artificial Sequence
<220> FEATURE:
<223> OTHER INFORMATION: Description of Artificial Sequence: gene X
      protein encoded by phage vector fpep3_1B-IR3seq (circular)

<400> SEQUENCE: 36

```
Met Asn Ile Tyr Asp Asp Ser Ala Val Leu Asp Ala Ile Gln Ser Lys
1               5                   10                  15

His Phe Thr Ile Thr Pro Ser Gly Lys Thr Ser Phe Ala Lys Ala Ser
            20                  25                  30

Arg Tyr Phe Cys Phe Tyr Arg Arg Leu Val Asn Glu Gly Tyr Asp Ser
        35                  40                  45

Val Ala Leu Thr Met Pro Arg Asn Ser Phe Trp Arg Tyr Val Ser Ala
    50                  55                  60

Leu Val Glu Cys Gly Ile Pro Lys Ser Gln Leu Met Asn Leu Ser Thr
65                  70                  75                  80

Cys Asn Asn Val Val Pro Leu Val Arg Phe Ile Asn Val Asp Phe Ser
                85                  90                  95

Ser Gln Arg Pro Asp Trp Tyr Asn Glu Pro Val Leu Lys Ile Ala
            100                 105                 110
```

<210> SEQ ID NO 37
<211> LENGTH: 87
<212> TYPE: PRT
<213> ORGANISM: Artificial Sequence
<220> FEATURE:
<223> OTHER INFORMATION: Description of Artificial Sequence: gene V
      protein encoded by phage vector fpep3_1B-IR3seq (circular)

<400> SEQUENCE: 37

```
Met Ile Lys Val Glu Ile Lys Pro Ser Gln Ala Gln Phe Thr Thr Arg
1               5                   10                  15

Ser Gly Val Ser Arg Gln Gly Lys Pro Tyr Ser Leu Asn Glu Gln Leu
            20                  25                  30

Cys Tyr Val Asp Leu Gly Asn Glu Tyr Pro Val Leu Val Lys Ile Thr
        35                  40                  45

Leu Asp Glu Gly Gln Pro Ala Tyr Ala Pro Gly Leu Tyr Thr Val His
    50                  55                  60

Leu Ser Ser Phe Lys Val Gly Gln Phe Gly Ser Leu Met Ile Asp Arg
65                  70                  75                  80

Leu Arg Leu Val Pro Ala Lys
                85
```

```
<210> SEQ ID NO 38
<211> LENGTH: 33
<212> TYPE: PRT
<213> ORGANISM: Artificial Sequence
<220> FEATURE:
<223> OTHER INFORMATION: Description of Artificial Sequence: gene VII
      protein encoded by phage vector fpep3_1B-IR3seq (circular)

<400> SEQUENCE: 38

Met Glu Gln Val Ala Asp Phe Asp Thr Ile Tyr Gln Ala Met Ile Gln
 1               5                  10                  15

Ile Ser Val Val Leu Cys Phe Ala Leu Gly Ile Ile Ala Gly Gly Gln
            20                  25                  30

Arg

<210> SEQ ID NO 39
<211> LENGTH: 36
<212> TYPE: PRT
<213> ORGANISM: Artificial Sequence
<220> FEATURE:
<223> OTHER INFORMATION: Description of Artificial Sequence: gene IX
      protein encoded by phage vector fpep3_1B-IR3seq (circular)

<400> SEQUENCE: 39

Met Ser Val Leu Val Tyr Ser Phe Ala Ser Phe Val Leu Gly Trp Cys
 1               5                  10                  15

Leu Arg Ser Gly Ile Thr Tyr Phe Thr Arg Leu Met Glu Thr Ser Ser
            20                  25                  30

Cys Val Ser Leu
        35

<210> SEQ ID NO 40
<211> LENGTH: 73
<212> TYPE: PRT
<213> ORGANISM: Artificial Sequence
<220> FEATURE:
<223> OTHER INFORMATION: Description of Artificial Sequence: gene VIII
      protein encoded by phage vector fpep3_1B-IR3seq (circular)

<400> SEQUENCE: 40

Met Arg Lys Ser Leu Val Leu Lys Ala Ser Val Ala Val Ala Thr Leu
 1               5                  10                  15

Val Pro Met Leu Ser Phe Ala Ala Glu Gly Asp Asp Pro Ala Lys Ala
            20                  25                  30

Ala Phe Asp Ser Leu Gln Ala Ser Ala Thr Glu Tyr Ile Gly Tyr Ala
        35                  40                  45

Trp Ala Met Val Val Val Ile Val Gly Ala Thr Ile Gly Ile Lys Leu
    50                  55                  60

Phe Lys Lys Phe Thr Ser Lys Ala Ser
65                  70

<210> SEQ ID NO 41
<211> LENGTH: 219
<212> TYPE: PRT
<213> ORGANISM: Artificial Sequence
<220> FEATURE:
<223> OTHER INFORMATION: Description of Artificial Sequence: cat protein
      encoded by phage vector fpep3_1B-IR3seq (circular)
```

```
<400> SEQUENCE: 41

Met Glu Lys Lys Ile Thr Gly Tyr Thr Thr Val Asp Ile Ser Gln Trp
  1               5                  10                  15

His Arg Lys Glu His Phe Glu Ala Phe Gln Ser Val Ala Gln Cys Thr
             20                  25                  30

Tyr Asn Gln Thr Val Gln Leu Asp Ile Thr Ala Phe Leu Lys Thr Val
         35                  40                  45

Lys Lys Asn Lys His Lys Phe Tyr Pro Ala Phe Ile His Ile Leu Ala
     50                  55                  60

Arg Leu Met Asn Ala His Pro Glu Phe Arg Met Ala Met Lys Asp Gly
 65                  70                  75                  80

Glu Leu Val Ile Trp Asp Ser Val His Pro Cys Tyr Thr Val Phe His
                 85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
            115                 120                 125

Glu Asn Leu Ala Tyr Phe Pro Lys Gly Phe Ile Glu Asn Met Phe Phe
130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Met Leu Asn Glu Leu
            195                 200                 205

Gln Gln Tyr Cys Asp Glu Trp Gln Gly Gly Ala
            210                 215

<210> SEQ ID NO 42
<211> LENGTH: 238
<212> TYPE: PRT
<213> ORGANISM: Artificial Sequence
<220> FEATURE:
<223> OTHER INFORMATION: Description of Artificial Sequence: ompA-FLAG-
      peptide3-gene IIIs encoded by phage vector fpep3_1B-IR3seq
      (circular)

<400> SEQUENCE: 42

Met Lys Lys Thr Ala Ile Ala Ile Ala Val Ala Leu Ala Gly Phe Ala
  1               5                  10                  15

Thr Val Ala Gln Ala Asp Tyr Lys Asp Val Asp Cys Ile Val Tyr His
             20                  25                  30

Ala His Tyr Leu Val Ala Lys Cys Gly Gly Gly Ser Glu Phe Asn
         35                  40                  45

Ala Gly Gly Ser Gly Gly Gly Ser Gly Gly Ser Glu Gly Gly
     50                  55                  60

Gly Ser Glu Gly Gly Ser Glu Gly Gly Ser Glu Gly Gly
 65                  70                  75                  80

Ser Gly Gly Ser Gly Ser Gly Asp Phe Asp Tyr Glu Lys Met Ala
                 85                  90                  95

Asn Ala Asn Lys Gly Ala Met Thr Glu Asn Ala Asp Glu Asn Ala Leu
            100                 105                 110

Gln Ser Asp Ala Lys Gly Lys Leu Asp Ser Val Ala Thr Asp Tyr Gly
            115                 120                 125
```

```
Ala Ala Ile Asp Gly Phe Ile Gly Asp Val Ser Gly Leu Ala Asn Gly
    130                 135                 140

Asn Gly Ala Thr Gly Asp Phe Ala Gly Ser Asn Ser Gln Met Ala Gln
145                 150                 155                 160

Val Gly Asp Gly Asp Asn Ser Pro Leu Met Asn Asn Phe Arg Gln Tyr
                165                 170                 175

Leu Pro Ser Leu Pro Gln Ser Val Glu Cys Arg Pro Phe Val Phe Gly
            180                 185                 190

Ala Gly Lys Pro Tyr Glu Phe Ser Ile Asp Cys Asp Lys Ile Asn Leu
        195                 200                 205

Phe Arg Gly Val Phe Ala Phe Leu Leu Tyr Val Ala Thr Phe Met Tyr
    210                 215                 220

Val Phe Ser Thr Phe Ala Asn Ile Leu Arg Asn Lys Glu Ser
225                 230                 235
```

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: primer FR604

<400> SEQUENCE: 43
gttcacgtag tgggccatcg                                               20

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: primer FR605

<400> SEQUENCE: 44
tgagaggtct aaaaaggcta tcagg                                         25

<210> SEQ ID NO 45
<211> LENGTH: 27
<212> TYPE: DNA
<213> ORGANISM: Artificial Sequence
<220> FEATURE:
<223> OTHER INFORMATION: Description of Artificial Sequence: primer FR606

<400> SEQUENCE: 45
tagccttttt agacctctca aaaatag                                       27

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: primer FR607

<400> SEQUENCE: 46
cggtgtacag accaggcgc                                                19

<210> SEQ ID NO 47
<211> LENGTH: 39
<212> TYPE: DNA
<213> ORGANISM: Artificial Sequence

```
<220> FEATURE:
<223> OTHER INFORMATION: Description of Artificial Sequence: DNA
      sequence encoding peptide pep3

<400> SEQUENCE: 47
tgtattgttt atcatgctca ttatcttgtt gctaagtgt                              39

<210> SEQ ID NO 48
<211> LENGTH: 13
<212> TYPE: PRT
<213> ORGANISM: Artificial Sequence
<220> FEATURE:
<223> OTHER INFORMATION: Description of Artificial Sequence: synthetic
      peptide pep3

<400> SEQUENCE: 48

Cys Ile Val Tyr His Ala His Tyr Leu Val Ala Lys Cys
 1               5                  10

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: primer
      FR614

<400> SEQUENCE: 49
gctctagata acgagggc                                                    18

<210> SEQ ID NO 50
<211> LENGTH: 26
<212> TYPE: DNA
<213> ORGANISM: Artificial Sequence
<220> FEATURE:
<223> OTHER INFORMATION: Description of Artificial Sequence: primer
      FR627

<400> SEQUENCE: 50
cgcaagctta agactcctta ttacgc                                           26
```

METHOD AND PHAGE FOR THE IDENTIFICATION OF NUCLEIC ACID SEQUENCES ENCODING MEMBERS OF A MULTIMERIC (POLY)PEPTIDE COMPLEX

This application is a Divisional of U.S. Ser. No. 09/495,880 filed Feb. 1, 2001, now U.S. Pat. No. 6,667,150, which is a continuation of International Application PCT/EP98/04836, filed Aug. 3, 1998. Application Ser. No. 09/495,880 is incorporated herein in its entirety by reference hereto.

The present invention relates to methods for the identification of nucleic acid sequences encoding members of a multimeric (poly)peptide complex by screening for polyphage particles. Furthermore, the invention relates to products and uses thereof for the identification of nucleic acid sequences in accordance with the present invention.

Since its first conception by Ladner in 1988 (WO88/06630), the principle of displaying repertoires of proteins on the surface of phage has experienced a dramatic progress and has resulted in substantial achievements. Initially proposed as display of single-chain Fv (scFv) fragments, the method has been expanded to the display of bovine pancreatic trypsin inhibitor (BPTI) (WO90/02809), human growth hormone (WO92/09690), and of various other proteins including the display of multimeric proteins such as Fab fragments (WO91/17271; WO92/01047).

A Fab fragment consists of a light chain comprising a variable and a constant domain (VL-CL) non-covalently binding to a heavy chain comprising a variable and constant domain (VH-CHI). In Fab display one of the chains is fused to a phage coat protein, and thereby displayed on the phage surface, and the second is expressed in free form, and on contact of both chains, the Fab assembles on the phage surface.

Various formats have been developed to construct and screen Fab phage-display libraries. In its simplest form, just one repertoire, e.g. of heavy chains, is encoded on the phage or phagemid vector. A corresponding light chain, or a repertoire of light chains, is expressed separately. The Fab fragments assemble either inside a host cell, if the light chain is co-expressed from a plasmid, or outside the cell in the medium, if a collection of secreted phage particles each displaying a heavy chain is contacted with the light chain(s) expressed from a different host cell. By screening such Fab libraries, just the information about the heavy chain encoded on the phage or phagemid vector is retrievable, since that vector is packaged in the phage particle. By reverting the format and displaying a library of light chains, and assembling Fab fragments by co-expressing or adding one or more of the heavy chains identified in the first round, corresponding light chain-heavy chain pairs can be identified.

To avoid that multi-step procedure, both repertoires may be cloned into one phage or phagemid vector, one chain expressible as a fusion with at least part of a phage coat protein, the second expressible in free form. After selection, the phage particle will contain the sequence information about both chains of the selected Fab fragments. The disadvantage of such a format is that the overall complexity of the library is limited by transformation efficiency. Therefore, the library size will usually not exceed $10^{10}$ members.

For various applications, a library size of up to $10^{14}$ would be advantageous. Therefore, methods of using site-specific recombination, either based on the Cre/lox system (WO92/20791) or on the attλ system (WO 95/21914) have been proposed. Therein, two collection of vectors are sequentially introduced into host cells. By providing the appropriate recombination sites on the individual vectors, recombination between the vectors can be achieved by action of an appropriate recombinase or integrase, achieving a combinatorial library, the overall library size being the product of the sizes of the two individual collections. The disadvantages of the Cre/lox system are that the recombination event is not very efficient, it leads to different products and is reversible. The attλ system leads to a defined product, however, it creates one very large plasmid which has a negative impact on the production of phages. Furthermore, the action of recombinase or integrase most likely leads to undesired recombination events.

Thus, the technical problem underlying the present invention is to develop a simple, reliable system which enables the simultaneous identification of members of a multimeric (poly)peptide complex, such as the identification of heavy and light chain of a Fab fragment, in phage display systems.

The solution to this technical problem is achieved by providing the embodiments characterized in the claims. Accordingly, the present invention allows to easily create and screen large libraries of multimeric (poly)peptide complexes for properties such as binding to a target, as in the case of screening Fab fragment libraries, or such as enzymatic activity, as in the case of libraries of multimeric enzymes. The technical approach of the present invention, i.e. the retrieval of information about two members of a multimeric (poly)peptide complex encoded on two different vectors without requiring a recombination event, is neither provided nor suggested by the prior art.

Accordingly, the present invention relates to a method for identifying a combination of nucleic acid sequences encoding two members of a multimeric (poly)peptide complex with a predetermined property, said combination being contained in a combinatorial library of phage particles displaying a multitude of multimeric (poly)peptides complexes, said method being characterized by screening or selecting for polyphage particles that contain said combination.

Surprisingly, it has been achieved by the present invention that the phenomenon of polyphages can be used to co-package the genetic information of two or more members of multimeric (poly)peptide complexes in a phage display system. The occurrence of polyphage particles has been observed 30 years ago (Salivar et al., Virology 32 (1967) 41–51), where it was described that approximately 5% of a phage population form particles which are longer than unit length and which contain two or more copies of phage genomic DNA. They occur naturally when a newly forming phage coat encapsulates two or more single-stranded DNA molecules. In specific cases, it has been seen that co-packaging of phage and phagemids or single-stranded plasmid vectors takes place as well (Russel and Model, J. Virol. 63 (1989) 3284–3295). Despite of occasional scientific articles about the morphogenesis of polyphage particles, a practical application has never been discussed or even been mentioned. In WO92/20791 in example 26, a model experiment for a combinatorial Fab display library expressed from separate vectors is presented. However, there is only a screening process for either of the two vectors described. Thus, the prior art teaches away from screening for the simultaneous presence of two vectors in a polyphage particle.

In the context of the present invention, the term "multimeric (poly)peptide complex" refers to a situation where two or more (poly)peptide(s) or protein(s), the "members" of said multimeric complex, can interact to form a complex. The interaction between the individual members will usually be non-covalent, but may be covalent, when post-translational modification such as the formation of disulphidebonds between any two members occurs. Examples for "multimeric (poly)peptide complexes" comprise structures such as fragments derived from immunoglobulins (e.g. Fv, disulphide-linked Fv (dsFv), Fab fragments), fragments derived from other members of the immunoglobulin superfamily (e.g. α,β -heterodimer of the T-cell receptor), and fragments derived from homo-or heterodimeric receptors or enzymes. In phage display, one of said members is fused to at least part of a phage coat protein, whereby that member is displayed on, and assembly of the multimeric complex takes place at, the phage surface. A "combinatorial phage library" is produced by randomizing at least two members of said multimeric (poly)peptide complex at least partially on the genetic level to create two libraries of genetically diverse nucleic acid sequences in appropriate vectors, by combining the libraries in appropriate host cells and by achieving co-expression of said at least two libraries in a way that a library of phage particles is produced wherein each particle displays one of the possible combinations out of the two libraries.

By screening such a combinatorial phage library displaying multimeric (poly)peptide complexes for a predetermined property, a collection of phage particles will be identified. Partially, these particles will just contain the genetic information of one of the members of the multimeric complex. The inventive principle of the present invention is the screening step for polyphage particles containing the genetic information of a combination of library members.

Furthermore, the present invention relates to a method for identifying a combination of nucleic acid sequences encoding two members of a multimeric (poly)peptide complex with a predetermined property, said combination being contained in a combinatorial library of phage particles displaying a multitude of multimeric (poly)peptides complexes, comprising the steps of (a) providing a first library of recombinant vector molecules containing genetically diverse nucleic acid sequences comprising a variety of nucleic acid sequences, each encoding a fusion protein of a first member of a multimeric (poly)peptide complex fused to at least part of a phage coat protein, said fusion protein thereby being able to be directed to, and displayed at, the phage surface, wherein said vector molecules are able to be packaged in a phage particle and carry or encode a first selectable and/or screenable property;

(b) providing a second library of recombinant vector molecules containing genetically diverse nucleic acid sequences comprising a variety of nucleic acid sequences, each encoding a second member of a multimeric (poly)peptide complex, wherein the vector molecules of said second library are able to be packaged in a phage particle and carry or encode a second selectable and/or screenable property different from said first property;

(c) optionally, providing nucleic acid sequences encoding further members of a multimeric (poly)peptide complex;

(d) expressing members of said libraries of recombinant vectors mentioned in steps (a), (b), and optionally nucleic acid sequences mentioned in step (c), in appropriate host cells under appropriate conditions, so that a combinatorial library of phage particles each displaying a multimeric (poly)peptide complex is produced;

(e) identifying in said library of phage particles a collection of phages displaying multimeric (poly)peptide complexes having said predetermined property;

(f) identifying in said collection polyphage particles simultaneously containing recombinant vector molecules encoding a first and a second member of said multimeric (poly)peptide complex by screening or selecting for the simultaneous presence or generation of said first and second selectable and/or screenable property;

(g) optionally, carrying out further screening and/or selection steps or repeating steps (a) to (f);

(h) identifying said combination of nucleic acid sequences.

Optionally, further members of said multimeric complex may be provided in the case of ternary, quaternary or higher (poly)peptide complexes. These further members may, for example, be co-expressed from one of the phage or phagemid vectors or from a separate vector such as a plasmid. Even libraries of such further members could be employed in which case further screenable or selectable properties would have to be introduced on the corresponding vectors. Alternatively, such further libraries could be contained in said first of second libraries of recombinant vector molecules. In another option, further screening and/or selection steps or a repetition of the individual steps can be carried out, to optimize the result of obtaining and identifying said nucleic acid sequences.

Furthermore, the present invention relates to a method for identifying a combination of nucleic acid sequences encoding two members of a multimeric (poly)peptide complex with a predetermined property, said combination being contained in a combinatorial library of phage particles displaying a multitude of multimeric (poly)peptides complexes, comprising the steps of (a) expressing in appropriate host cells under appropriate conditions (aa) genetically diverse nucleic acid sequences contained in a first library of recombinant vector molecules, said nucleic acid sequences comprising a variety of nucleic acid sequences, each encoding a fusion protein of a first member of a multimeric (poly)peptide complex fused to at least part of a phage coat protein, said fusion protein thereby being able to be directed to and displayed at the phage surface, wherein said vector molecules are able to be packaged in a phage particle and carry or encode a first selectable and/or screenable property;

(ab) genetically diverse nucleic acid sequences contained in a second library of recombinant vector molecules, said nucleic acid sequences comprising a variety of nucleic acid sequences, each encoding a second member of a multimeric (poly)peptide complex, wherein the vector molecules are able to be packaged in a phage particle and carry or encode a second selectable and/or screenable property different from said first property;

(ac) optionally, nucleic acid sequences encoding further members of a multimeric (poly)peptide complex, so that a combinatorial library of phage particles each displaying a multimeric (poly)peptide complex is produced;

(b) identifying in said library of phage particles a collection of phages displaying multimeric (poly)peptide complexes having said predetermined property;

(c) identifying in said collection polyphage particles simultaneously containing recombinant vector molecules encoding a first and a second member of said multimeric (poly)peptide complex by screening or selecting for the simultaneous presence or generation of said first and second selectable and/or screenable property;

(d) optionally, carrying out further screening and/or selection steps or repeating steps (a) to (c);

(e) identifying said combination of nucleic acid sequences.

In a preferred embodiment of the method of the present invention, the vectors of said first and said second library are a combination of a phage vector and a phagemid vector.

In a further preferred embodiment of the method of the present invention, the vectors of said first and said second library are a combination of two phagemid vectors, said appropriate conditions comprising complementation of phage genes by a helper phage.

In a most preferred embodiment of the method of the present invention said two phagemid vectors are compatible.

The term "compatibility" refers to a property of two phagemids to be able to coexist in a host cell. Incompatibility is connected to the presence of incompatible plasmid origins of replication belonging to the same incompatibility group. An example for compatible plasmid origins of replication is the high-copy number origin ColE1 and the low-copy number origin p15A.

Therefore, in a further preferred embodiment of the method of the present invention, said two phagemid vectors comprise a ColE1 and a p15A plasmid origin of replication.

In a most preferred embodiment of the method of the present invention, said two phagemid vectors comprise a ColE1 and a mutated ColE1 origin.

It could be shown, that two phagemids both having a ColE1-derived plasmid origin of replication can coexist in a cell as long as one of the ColE1 origins carries a mutation.

Particularly preferred is a method, wherein said vectors and/or said helper phage comprise different phage origins of replication.

Most preferred is an embodiment of the method of the present invention, wherein said phage vector, said phagemid vector(s) and/or said helper phage are interference resistant.

The term "interference" refers to a property that phagemids inhibit the production of progeny phage particles by interfering with the replication of the DNA of the phage. "Interference resistance" is a property which overcomes this problem. It has been found that mutations in the intergenic region and/or in gene II contribute to interference resistance (Enea and Zinder, Virology 122 (1982), 222–226; Russel et al., Gene 45 (1986) 333–338). It was identified that phages called IR1 and IR2 (Enea and Zinder, Virology 122 (1982), 222–226), and mutants derived therefrom such as R176 (Russel and Model, J. Bacteriol. 154 (1983) 1064–1076), R382, R407 and R408 (Russel et al., Gene 45 (1986) 333–338) and R383 (Russel and Model, J. Virol. 63 (1989) 3284–3295) are interference resistant by carrying mutations in the untranslated region upstream of gene II and in the gene II coding region.

Therefore, in a preferred embodiment of the method of the present invention, said phage vector, said phagemid vector(s) and/or said helper phage have mutations in the phage intergenic region(s), preferably in positions corresponding to position 5986 of f1, and/or in gene II, preferably in positions corresponding to position 143 of f1.

In a most preferred embodiment said phage vector, said phagemid vector(s) and/or said helper phage are, or are derived from, IR1 mutants such as R176, R382, R383, R407, R408, or from IR2 mutants.

In a further embodiment or the method of the invention, said vectors and/or said helper phage comprise hybrid nucleic acid sequences of f1, fd, and/or M13 derived sequences.

In the context of the present invention, the term "hybrid nucleic sequences" refers to vector elements which comprise sequences originating from different phage(mid) vectors.

Surprisingly, it has been found that a vector constructed combining a part derived from fd phage and a second part derived from R408, a derivative of f1 phages, is interference resistant and additionally, gives predominantly polyphage particles. Therefore, a most preferred embodiment of the method of the present invention relates to a vector which is, or is derived from, fpep3_1B-IR3seq with the sequence listed in FIG. 4.

In a yet further preferred embodiment of the method according to the present invention, said derivative is a phage comprising essentially the phage origin or replication from fpep3_1B-IR3seq, the gene II from fpep3_1B-IR3seq, or a combination of said phage origin of replication and said gene II.

The invention relates in an additional preferred embodiment to a method, wherein said derivative is a phagemid comprising essentially the phage origin or replication from fpep3_1B-IR3seq, the gene II from fpep3_1B-IR3seq, or a combination of said phage origin of replication and said gene II.

The invention relates in a further preferred embodiment to a method, wherein said derivative is a helper phage comprising essentially the phage origin or replication from fpep3_1B-IR 3seq, the gene II from fpep3_1B-IR3seq, or a combination of said phage origin of replication and said gene II.

Most preferred is an embodiment of the method of the invention, wherein said derivatives comprise the combined fd/f1 origin including the mutation G5737>A (2976 in fpep3_1B-IR3seq), and/or the mutations G343>A (3989) in gII, and G601>T (4247) in gII/X.

The formation of polyphage particles has been examined in more detail by different groups. It was found that amber mutations in genes VII and IX lead to the amplified production of infectious polyphage particles (Lopez and Webster, Virology 127 (1983) 177–193). A couple of mutants in gene VII (R68, R100) and in gene IX (N18) were identified and further characterized.

Accordingly, in a preferred embodiment of the method of the present invention, the gene VII contained in any of said vectors contains an amber mutation, and most preferably, said mutation is identical to those found in phage vectors R68 or R100.

Further preferred is an embodiment, wherein the gene IX contained in any of said vectors contains an amber mutation, and most preferably said mutation is identical to that found in phage vector N18.

Several phage coat proteins have been used in displaying foreign proteins including the gene III protein (gIIIP), gVIp, and gVIIIp. In a preferred embodiment of the method of the present invention, said phage coat protein is gIIIp or gVIIIp.

In a particularly preferred embodiment of the method of the present invention, said phage particles are infectious by having a full-length copy of gIIIp.

The gIIIp is a protein comprising three domains. The C-terminal domain is responsible for membrane insertion, the two N-terminal domains are responsible for binding to the F pilus of *E. coli* (N2) and for the infection process (N1).

In a most preferred embodiment of the method of the invention, said phage particles are non-infectious by having no full-length copy of gIIIp, said fusion protein being formed with a truncated version of gIIIp, wherein the infectivity can be restored by interaction of the displayed multimeric (poly)peptide complexes with a corresponding partner coupled to an infectivity-mediating particle.

In the context of the present invention, the term "infectivity-mediating particle" (IMP) refers to a construct comprising either the N1 domain or the N1-N2 domain. On interaction with a non-infectious phage lacking said domains, infectivity of the phage particles can be restored. The interaction between the non-infectious phage and the IMP can be mediated by a ligand fused to the IMP, which can bind to a partner displayed on the phage. By screening a non-infectious phage display library against a target ligand-IMP construct, restoration of infectivity can be used to select target-binding library members.

In a further preferred embodiment of the method of the invention, said truncated gIIIp comprises the C-terminal domain of gIIIp.

In a yet preferred embodiment of the method of the invention, said truncated gIIIp is derived from phage fCA55.

In addition to the work by Lopey and Webster cited above, Crissman and Smith (Virology 132 (1984) 445–455) could show, that the phage fCA55 which has a large deletion in gene III removing the N-terminal domains and a large part of the C-terminal domain leads exclusively to the formation of polyphages.

Particularly preferred is an embodiment of the method of the invention, wherein said predetermined property is binding to a target.

In a preferred embodiment of the method of the invention, said multimeric (poly)peptide complex is a fragment of an immunoglobulin superfamily member.

In a most preferred embodiment of the method of the invention, said multimeric (poly)peptide complex is a fragment of an immunoglobulin.

In a further most preferred embodiment of the method of the invention, said fragment is an Fv, dsFv or Fab fragment.

An additional preferred embodiment of the present invention relates to a method, wherein said predetermined property is the activity to perform or to catalyze a reaction.

In a preferred embodiment of the method of the invention, said multimeric (poly)peptide complex is an enzyme.

In a most preferred embodiment of the method of the invention, said multimeric (poly)peptide complex is a fragment of a catalytic antibody.

In a further most preferred embodiment of the method of the invention, said fragment is an Fv, dsFv or Fab fragment.

An additional preferred embodiment of the invention relates to a method, wherein selectable and/or screenable property is the transactivation of transcription of a reporter gene such as beta-galactosidase, alkaline phosphatase or nutritional markers such as his3 and leu, or resistance genes giving resistance to an antibiotic such as ampicillin, chloramphenicol, kanamycin, zeocin, neomycin, tetracycline or streptomycin.

In a most preferred embodiment of the method of the invention, said generation of said first and second screenable and/or selectable property is achieved after infection of appropriate host cells by said collection of phage particles.

Particularly preferred is a method, wherein said identification of said nucleic acid sequences is effected by sequencing.

Further preferred is a method, wherein said host cells are E.coli XL-1 Blue, K91 or derivatives, TG1, XL1kann or TOP10F.

An additional preferred embodiment of the invention relates to a polyphage particle which
(a) contains
(i) a first recombinant vector molecule that comprises a nucleic acid sequence, which encodes a fusion protein of a first member of a multimeric (poly)peptide complex fused to at least part of a phage coat protein, and that carries or encodes a first selectable and/or screenable property, and
(ii) a second recombinant vector molecule that comprises a nucleic acid sequence, which encodes a second member of a multimeric (poly)peptide complex, and that carries or encodes a second selectable and/or screenable property different from said first property;
and (b) displays said multimeric (poly)peptide complex at its surface.

A most preferred embodiment of the invention relates to a polyphage particle, wherein said phage coat protein is the gIIIp.

A further preferred embodiment of the present invention relates to a polyphage particle which is infectious by having a full-length copy of gIIIp present, either in said fusion protein, or in an additional wild-type copy.

Additionally, the invention relates to a polyphage particle which is non-infectious by having no full-length copy of gIIIp, said fusion protein being formed with a truncated version of gIIIp, wherein the infectivity can be restored by interaction of the displayed multimeric (poly)peptide complex with a corresponding partner coupled to an infectivity-mediating particle.

Most preferably, the invention relates to the phage vector fpep3_1B-IR3seq with the sequence listed in FIG. 4.

Additionally preferred, the invention relates to a phage vector derived from phage vector fpep3_1B-IR3seq comprising essentially the phage origin or replication from fpep3_1B-IR3seq, the gene II from fpep3_1B-IR3seq, or a combination of said phage origin of replication and said gene II.

Further preferred is an embodiment of the invention, which relates to a phagemid vector derived from phage vector fpep3_1B-IR3seq comprising essentially the phage origin of replication from fpep3_1B-IR3seq, the gene II from fpep3_1B-IR3seq, or a combination of said phage origin of replication and said gene II.

Preferably, the invention relates to a helper phage vector derived from phage vector fpep3_1B-IR3seq comprising essentially the phage origin of replication from fpep3_1B-IR3seq, the gene II from fpep3_1B-IR3seq, or a combination of said phage origin of replication and said gene II.

Additionally preferred is an embodiment, said derivatives comprise the combined fd/f1 origin including the mutation G5737>A (2976 in fpep3_1B-IR3seq), and/or the mutations G343>A (3989) in gII, and G601>T (4247) in gII/X.

Further preferred is the use of any of the vectors according to the present invention in the generation of polyphage particles containing a combination of at least two different vectors.

Most preferred is the use of vectors of the invention, wherein said combination of different vectors comprises nucleic acid sequences encoding members of a multimeric (poly)peptide complex.

Further preferred in the present invention is the use of vectors, wherein said combination of different vectors comprises nucleic acid sequences encoding interacting (poly)peptides/proteins.

LEGENDS TO FIGURES

FIG. 1: General description of the polyphage principle for the display of a Fab library: e.g. library 1: library of VL chains; library 2: VH chains; both libraries on compatible phagemids; in a: libraries are transformed into host cells; in b: library 1 is rescued by a helper phage; in c: libraries are combined by infection; in d: co-expression of heavy and light chains; in e: rescue by helper phages, production of phage particles, assembly of Fab on phage, selection for target; note 1: A certain fraction of the phage particles will be normal unit-lenght particles containing just one of the two genomes (not shown in FIG. 1). Furthermore, polyphage does not discriminate which genomes to package. Therefore, the combinations shown in FIG. 1 can arise. To select for correctly packaged genomes, the subsequent steps are required; in f: infect host cells; in g: select for ability to confer resistance to two antibiotics to infected cells; note 2: only phage that satisfy condition according to g) represent polyphage particles which contain the correct combination of heavy and light chain of binding Fabs (Hetero-polyphage). Unit-length phage as well as polyphage carrying two identical genomes will confer only resistance to one antibiotics.

FIG. 2: Functional map and sequence of phage vector fhag1A (SEQ ID NO: 3)

FIG. 3: Functional map and sequence of phage vector fjun_1 B (SEQ ID NO: 18)

FIG. 4: Functional map and sequence of phage vector fpep3_1B-IR3seq (SEQ ID NO: 31)

FIG. 5: Compatibility of various phage and phagemid vectors: co-transformation of different vector pairs and growth in liquid culture (can/amp selection): A. fjun_1B-R408-IR/pIG10_pep10; B. fjun_1B/pIG10_pep10 (only 1 colonie); C. fpep3_1B-IR3/pIG10_pep10; D. fjun_1B-R408-IR/pOK1Djun; E. fjun_1B/pOK1Djun: no growth; F. fpep3_1B-IR3/pOK1Djun; a. fjun_1B; b. fjun_1B-R408-IR; c. fpep3_1B-IR3; d. pIG10_pep10; e. pOK1Djun FIG. 6: co-transformation of positive (pep3/p751CD combination, lane 9) and negative (jun/p751CD, lane 10) pairs; lane 1 to 8: SIP transductants FIG. 7: Sensitivity of SIP hetero-polyphage system for selection in solution: #SIP hetero-polyphage transductants, transducing units (t.u.)/ml, produced by co-cultures of co-transformants as in FIG. 6 mixed at the indicated ratios.

Figure 8:
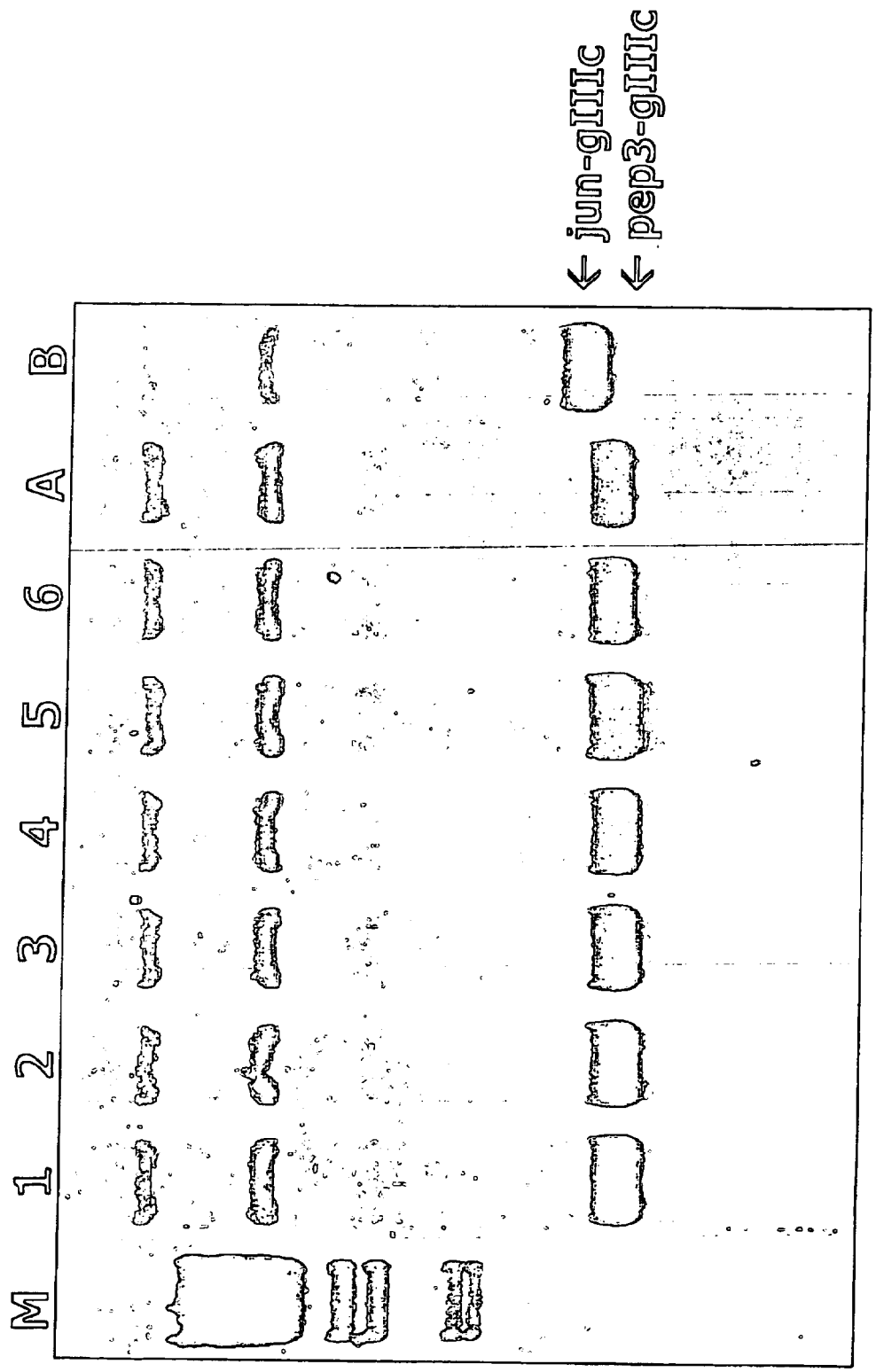

FIG. 8: PCR to identify phage vector(s) present in SIP polyphage transductants: lane 1 to 6: SIP polyphage transductants; lane A: fpep3_1B-IR3/pIG10.3-IMPp75 co-transformant; lane B: fjun_1B-IR3/pIG10.3-IMPp75 co-transformant FIG. 9: IR Phage and Phagemid are Co-packaged into Polyphages: 1: ΔgIII phage+gIII plasmid; 2: IR phage+phagemid FIG. 10: SIP Information is Co-transduced by Polyphages: a: IMPp75 on phage vector; b: pep10-gIII-CT fusion on phage vector; c: IMPp75 on phagemid vector; d: pep10-gIII-CT fusion on phagemid vector The examples illustrate the invention

EXAMPLE 1

Selection for Polyphage Transductants

In WO92/01047, page 83, a model experiment for a two-vector system is described which uses a phage vector (fd-CAT2-IV) encoding a light chain and a phagemid vector (pHEN1-III) encoding a heavy chain. The phagemid, grown in *E. coli* HB2151, was rescued with fd-CAT2-IV phage, and functional phage(mid)s produced. By infecting TG1 cells and plating on tetracycline (to select for fd-CAT) and ampicillin (to select for pHEN1), the ratio of phage and phagemid being packaged was determined.

By repeating this experiment, but plating on TYE plates with both antibiotics, polyphage transductants transducing both resistances simultaneously can be selected, and the genetic information contained on the phage and phagemid vector can be retrieved.

By replacing the single light and heavy chain in the constructs mentioned above by corresponding repertoires, a library of Fab-displaying phage particles can be produced. By screening that library against an immobilized target, a collection of phage particles can be identified. Polyphage particles contained in that collection can be identified by transducing both resistances as described above.

EXAMPLE 2

Generation and Use of an Interference-resistant Filamentous Phage to Co-Package the Genetic Information of Co-displayed Interacting Proteins Introduction The physical connection of randomly combined genetic information is of vital importance in processes such as interactive screening of two libraries of expressed protein members or for co-expression and co-display of protein pairs which are dependent on the interaction with each other for proper function.

2.1.: Construction of a Interference Resistant Filamentous Phage:

2.1.1.: Construction of fjun_1B:

fhag1A (see FIG. 2)

a. The phage vector f17/9-hag (Krebber et al., 1995, *FEBS Letters* 377, 227–231) is digested with EcoRV and XmnI. The 1.1 kb fragment containing the anti-HAG Ab gene is isolated by agarose gel electrophoresis and purified with a Qiagen gel extraction kit. This fragment is ligated into a pre-digested pIG10.3 vector (EcoRV-XmnI). Ligated DNA is transformed into DH5a cells and positive clones are verified by restriction analysis. The recombinant clone is called pIGhag1A. All cloning described above and subsequently are according to standard protocols (Sambrook et al., 1989, *Molecular Cloning: a Laboratory Manual*, 2$^{nd}$ ed.)

b. The vector f17/9-hag (Krebber et al., 1995) is digested with EcoRV and StuI. The 7.9 kb fragment is isolated and self-ligated to form the vector fhag2.

c. The chioramphenicol resistance gene (CAT) assembled via assembly PCR (Ge and Rudolph, *BioTechniques* 22 (1997) 28–29) using the template pACYC (Cardoso and Schwarz, *J. Appi. Bacteriol.* 72 (1992) 289–293) is amplified by the polymerase chain reaction (PCR) with the primers:

```
CAT_BspEI(for):                 (SEQ ID NO 1)
5'GAATGCTCATCCGGAGTTC

CAT_Bsu36I(rev):                (SEQ ID NO 2)
5'TTTCACTGGCCTCAGGCTAGCACCAGGCGTTTAAG
``` d. The PCR is done following standard protocols (Sambrook et al., 1989). The amplified product is digested with BspEI and Bsu36I then ligated into pre-digested fhag2 vector (BspEI-Bsu36I; 7.2 kb fragment) to form fhag2C.

e. The vector fhag2C is digested with EcoRI and the ends made blunt by filling-in with Klenow fragment. The flushed vector is self-ligated to form vector fhag2CdelEcoRI.

f. pIGhag1A is digested with XbaI and HindIII. The 1.3 kb fragment containing the anti-HAG gene fused with the C-terminal domain of filamentous phage pIII protein is isolated and ligated with a pre-digested fhag2CdelEcoRI phage vector (XbaI-HindIII; 6.4 kb) to create the vector fhag1A.

fjun_1B (see FIG. 3)

a. The DNA encoding the C-terminal domain including the long linker separating it from the amino terminal domain of the filamentous phage pIII (gIII short) is amplified by PCR using pOK1 (Gramatikoff et al., *Nucleic Acids Res.* 22 (1994) 5761–5762) as template with the primers:

```
gIII short(for):                        (SEQ ID NO 16)
5'GCTTCCGGAGAATTCAATGCTGGCGGCGGCTCT3' gIII short(rev):                        (SEQ ID NO 17)
5'CCCCCCCAAGCTTATCAAGACTCCTTATTACG3'
``` b. The PCR is done following standard protocols (Sambrook et al., 1989). The amplified product is digested with EcoRI and HindIII, then ligated into pre-digested fhag1A vector (EcoRI-HindIII) to form the vector fjun_1B.

2.1.2.: Construction of fjun_1B-R408IR:

In order to introduce mutations which have been described to confer an interference resistance phenotype (Enea and Zinder, Virology 122 (1982), 222–226) into the non-interference resistant fd phage vector fjun_1B (see FIG. 3), a 1.7 kb fragment of helper phage R408 (Stratagene) comprising the region between the unique restriction sites DraIII and BsrGI was PCR amplified by assembly PCR. Subfragments of the 1.7 kb DraIII/BsrGI fragment were amplified from the f1 phage R408 template DNA with primer combinations FR604/FR605 and FR606/FR607 to introduce via the partially complementary primers FR605 and FR606 an additional gII mutation found to be present in the recipient construct fjun_1B. Resulting PCR fragments were gel-purified and combined to serve as template in an subsequent assembly PCR with primers FR604 and FR607. PCR conditions were standard, with approx. 25 ng template, 10 pmole of each primer, 250 pmole of each dNTP, 2 mM Mg, 2.5 U Pfu DNA polymerase (Stratagene). Amplification was done for 30 cycles, with 1 min denaturation at 94 C, 1 min annealing at 50° C., 1 min extension at 72° C. The correct-sized 1.7 kb assembly PCR product was gel-purified, digested with DraIII and BsrGI and cloned into DraIII/BsrGI-digested fjun_1B, generating fjun_1B-R408IR.

```
Primers: FR604                          (SEQ ID NO 43)
         5'GTTCACGTAGTGGGCCATCG 3'

FR605                          (SEQ ID NO 44)
         5'TGAGAGGTCTAAAAAGGCTATCAGG 3'

FR606                          (SEQ ID NO 45)
         5'TAGCTTTTTAGACCTCTCAAAAATAG 3'

FR607                          (SEQ ID NO 46)
         5'CGGTGTACAGACCAGGCGC 3'
```

2.2.: Proof of Principle Experiments

Despite of the absence of the two originally associated IR mutations, the hybrid phage vector fjun_1B-R408IR (carrying the chloramphenicol acetyltransferase confering chloramphenicol resistance) could be co-transformed with a phagemid (pOK1deltajun, carrying the beta-lactamase gene confering ampicilin resistance) containing a phage origin of replication. More importantly, fjun_1B-R408IR could stably co-exist with the phagemid pOK1deltajun, and the phagemid was efficiently co-packaged together with the fjun_1B-R408IR phage genome into polyphage particles. Titers of polyphages, simultaneously transducing chloramphenicol and ampicilin resistance, reached $6 \times 10^8$ transducing units (t.u.)/ml of overnight bacterial culture K91 plating cells, a number almost equivalent to a titer of $10^9$/ml seen after selection on chloramphenicol only. Selection of the K91 transductants on ampicilin only gave a titer of $5 \times 10^9$/ml. These titers indicated that more than 50 % of all phages containing fjun_1B-R408IR also contained the phagemid pOK1deltajun, thus representing polyphages. This high ratio of polyphages was confirmed by restriction analysis of transductants which had been selected on chloramphenicol only. More than 50 % of these clones also contained the phagemid in addition to the fjun_1B-R408IR phage genome. fjun_1B-R408IR was isolated in pure form from an individual transductant, which contained only this phage. The construct fjun_1B-R408IR was used with pOK1deltajun for co-transformation of DH5α cells, in order to produce selectively-infective phages (SIP) via fos-jun leucine zipper interaction (which non-covalently restores wt gIII function). Stable, double-resistant co-transformants were obtained with this combination and individual clones were grown overnight in the presence of cam/amp. The culture supernatant of these clones was filtered through a 45 μM membrane filter and used to infect exponentially-growing F+ bacteria (K91 strain) for 20 min at 37 C. To test for the presence of infective SIP polyphages the cells were plated on LB agar plates containing cam and amp and plates were incubated at 37 C overnight. Approx. 500 to 1000 transforming units (t.u.)/ml resulting in double-resistant transductants were obtained from individual co-transformants. DNA of those transductants was analyzed by restriction analysis which showed that 95 % (15/16 clones) of the clones had the correct pattern expected for fjun_1B-R408IR and pOK1deltajun. Supernatants of several polyphage transductants were tested for persistent SIP phage production by re-infection of K91 cells. This confirmed that polyphage transductants continued to produce infective SIP phages and restriction analysis of the resulting $2^{nd}$ round polyphage transductants showed that 44 % (14/32 clones) contained the correct vector combination. The rest of the clones contained the correct pOK1deltajun phagemid plus a recombined phage vector with a restored wt gIII, indicating an increase in recombination frequency when both vectors are propagated in the rec+ strain K91 (compared to the rec– strain DH5α used for co-transformation of IR phage and phagemid). To test other protein-protein interactions which give a higher titer of infective SIP phages and to verify the presence of hetero-polyphages (co-packaging of phage and phagemid instead of co-infection by monophages or homo-polyphages), two peptide ligands (previously selected by SIP, WO97/32017) which bind to the p75 rat neurotrophin receptor (Chao et al., Science 232 (1986) 518–521) intracellular domain (p75ICD) were cloned as N-terminal gIIIc fusions in fjun_1B-R408IR (replacing jun) and the phagemid pIG10.3, leading to constructs fpep3_1B-IR3seq and pIG10.3-pep10 (WO97/32017), respectively, which contain the peptide pep3: 5'-TGTATTGTTTATCATGCTCAT-TATCTTGTTGCTAAGTGT-3' (SEQ ID NO 47) encoding the amino acid sequence (CysIleValTyrHisAlaHisTyrLeu-ValAlaLysCys (SEQ ID NO 48)) instead of the jun sequence. Sequencing of the respective parts of the transferred R408 fragment in fpep3_1B-IR3seq revealed that neither of the two IR mutations (the G5986>A mutation from complementation group I in the gII 5' non-translated region, which should be found at position 3225 in fpep3_1B-IR3seq, and the C143>T mutation (3789 in fpep3_1B-IR3seq) from complementation group II leading to a Thr>Ile amino acid exchange in gII) were found to be present. However; the gII mutation G6090>T (3329 in fpep3_1B-IR3seq), leading to a Leu>Val exchange, introduced by assembly PCR was present. Furthermore, three additional mutations compared to an f1 phage could be identified: G5737>A (2976 in fpep3_1B-IR3seq) in the phage origin of replication, G343>A (3989) in gII, and G601>T (4247) in gII/X.

The functional map and the sequence of fpep3_1B-IR3seq are given in FIG. 4. This sequence was double-checked several times. It could be shown that differences in the sequence of fpep3_1B-IR3seq compared to published sequence data could be explained by mutations already present in the starting constructs used for cloning fjun_1B-R408IR and fpep3_1B-IR3seq.

Co-transformation experiments (FIG. 5) using combinations of pIG10.3 or pOK1 phagemids (both with f1 oris) with fjun_1B ("wt" fd phage), fjun_1B-R408-IR (containing the DraIII/BsrGI fragment from R408) or fpep3_1B-IR3 (containing the DraIII/BsrGI fragment from R408 and the PCR mutation) revealed that the PCR mutation is not necessary for the IR phenotype, at least judged by the ability to be co-transformable with a phagemid and the ability of individual co-transformants to grow in liquid culture (cam/amp selection).

Additionally, the interacting protein partner p751CD was cloned as a C-terminal fusion to the infectivity-mediating domains (N1-N2) of gIII (infectivity-mediating particle (IMP) fusion) resulting in constructs fIMPp75-IR3 and pIG10.3-IMPp75.

Figure 6:
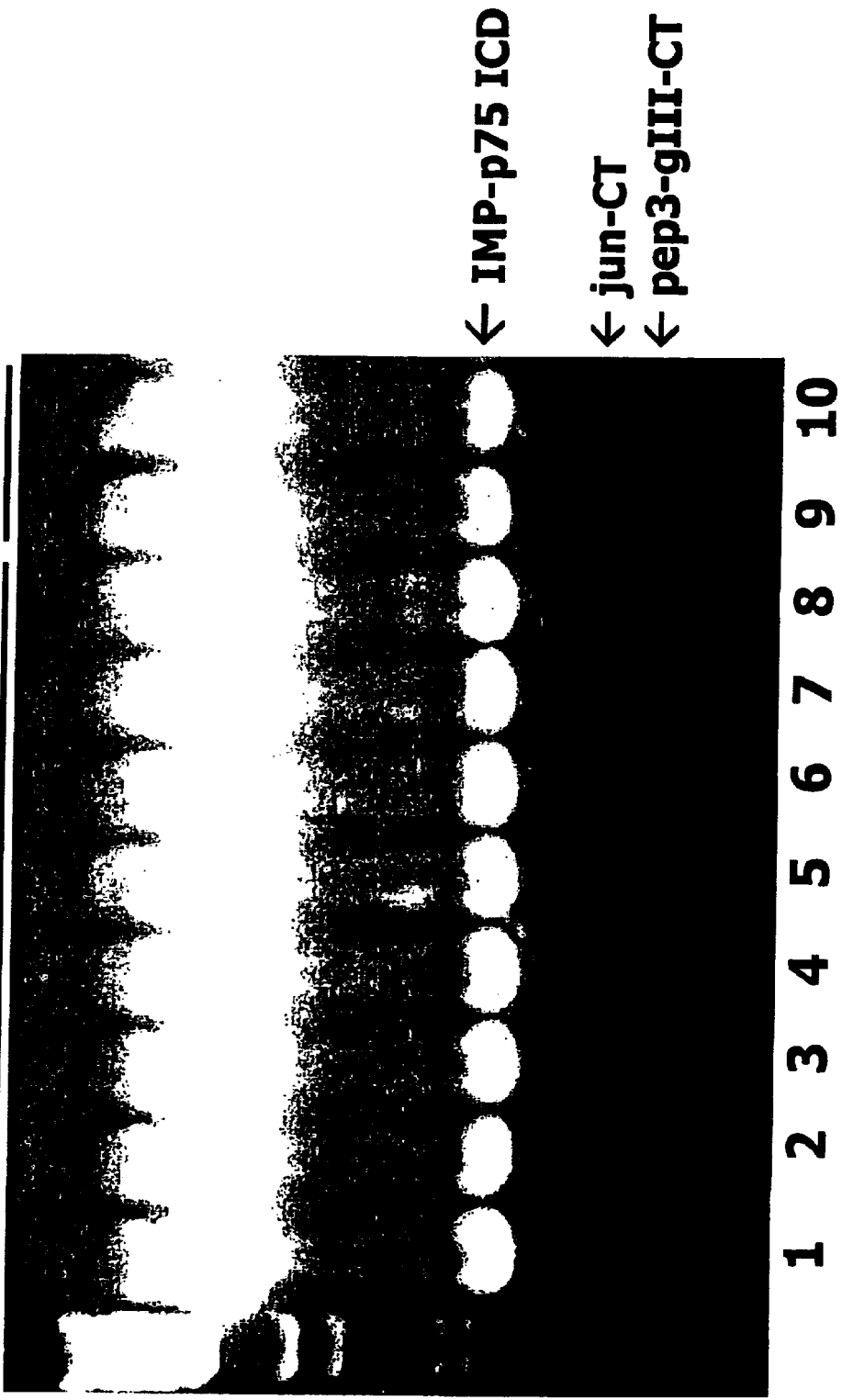

The IR phage was tested with the SIP pairing fpep3_1B-IR3seq3/pIG10.3-IMPp75 (which gives a higher titer than fos/jun SIP) in the presence of the negative control combination fjun_1B-IR3seq3/pIG10.3-IMPp75 (FIG. 6). A SIP hetero-polyphage titer of $1.5 \times 10^5$/ml (cam/amp-resistant transductants) was achieved with fpep3_1B-IR3seq3/pIG10.3-IMPp75. To test SIP sensitivity in a model library vs. library setting, co-transformants of fpep3_1B-IR3seq3/pIG10.3-IMPp75 were diluted in an excess fjun_1B-IR3/pIG10.3-IMPp75 and the supernatant of the bacterial co-culture was assayed for SIP hetero-polyphages. This showed that down to a dilution of $10^{-5}$ to $10^{-6}$ can be recovered (FIG. 7).

To prove that only the correct phage vector is present in SIP polyphage transductants, DNA of positive (fpep3_1B-IR3seq3/pIG10.3-IMPp75) and negative (fjun_1B-IR3/pIG10.3-IMPp75) control co-transformants, as well as DNA from the SIP polyphage transductants derived from SIP phages produced by the mix of positive and negative control bacteria was analyzed by PCR (FIG. 8). Primers FR614 (5'-GCTCTAGATAACGAGGGC-3') and FR627 (5'-CG-CAAGCTTAAGACTCCTTATTACGC-3') amplify the phage region from the start of ompA to the end of gIII. PCR products derived from fpep3_1B-IR3seq3 and fjun_1B-IR3 can be discriminated by size. Gel analysis of the above samples verified that only the expected fpep3_1B-IR3seq3 phage was present in SIP polyphage transductants (6 analyzed).

Figure 9:
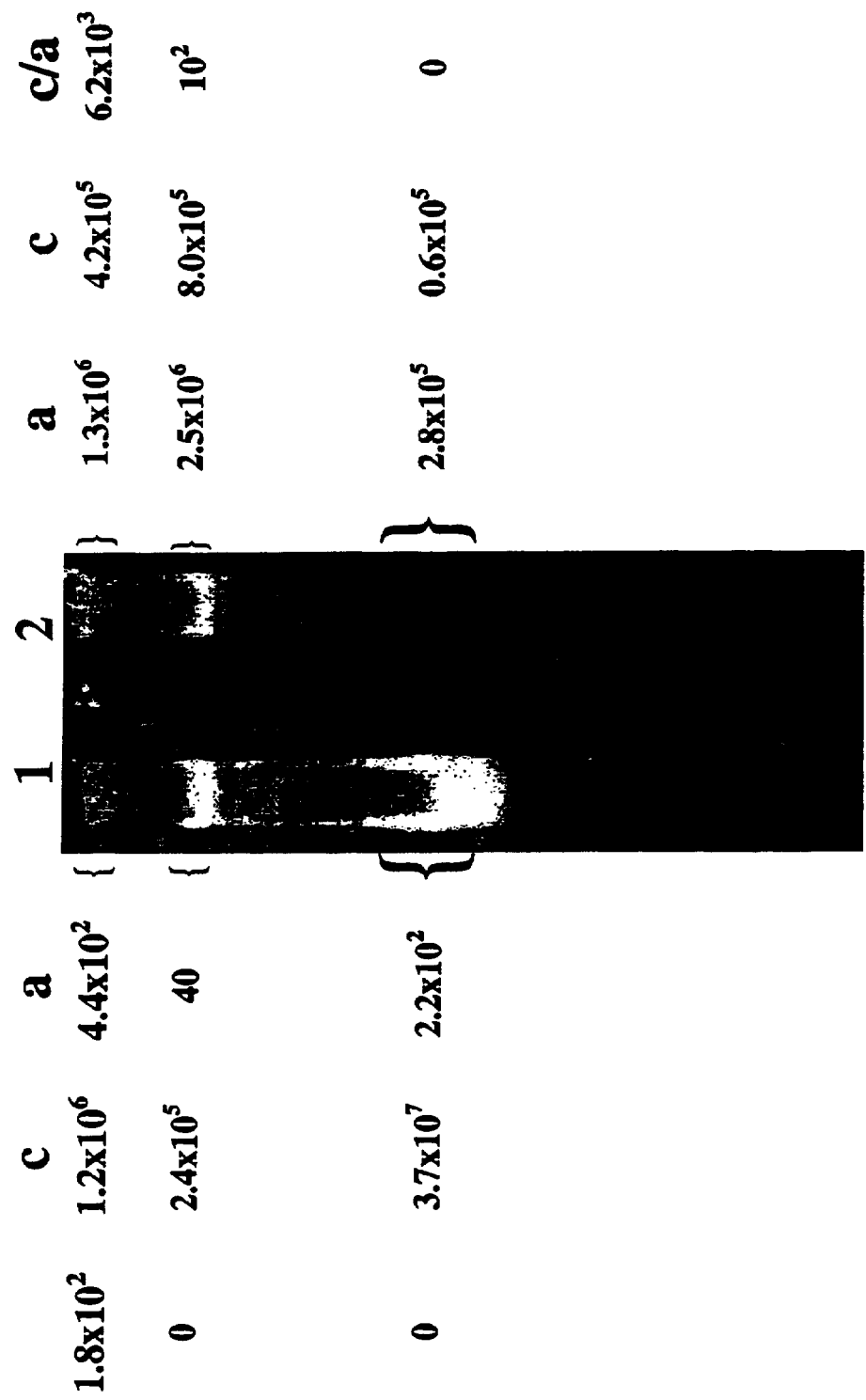

To physically demonstrate the existence of hetero-polyphages (which have phage and phagemid co-packaged) when using the IR phage vector, phages produced by co-transformants of fIR3/pIG10.3-IMPp75 and as a control fjun_1B/JB61 ("wt" phage plus complementing gIII plasmid) were separated on an agarose gel (FIG. 9). This showed that the fIR3/pIG10.3-IMPp75 combination produced substantially more slower migrating (thus bigger) phages than the fjun_1B/JB61 control combination. The ratio was almost inversed. Elution of phages from various regions of the gel and subsequent titering of the eluate on plating cells showed that the upper gel region contained a significant portion of double resistance-transducing phages which thus can be regarded as hetero-polyphages.

Figure 10:
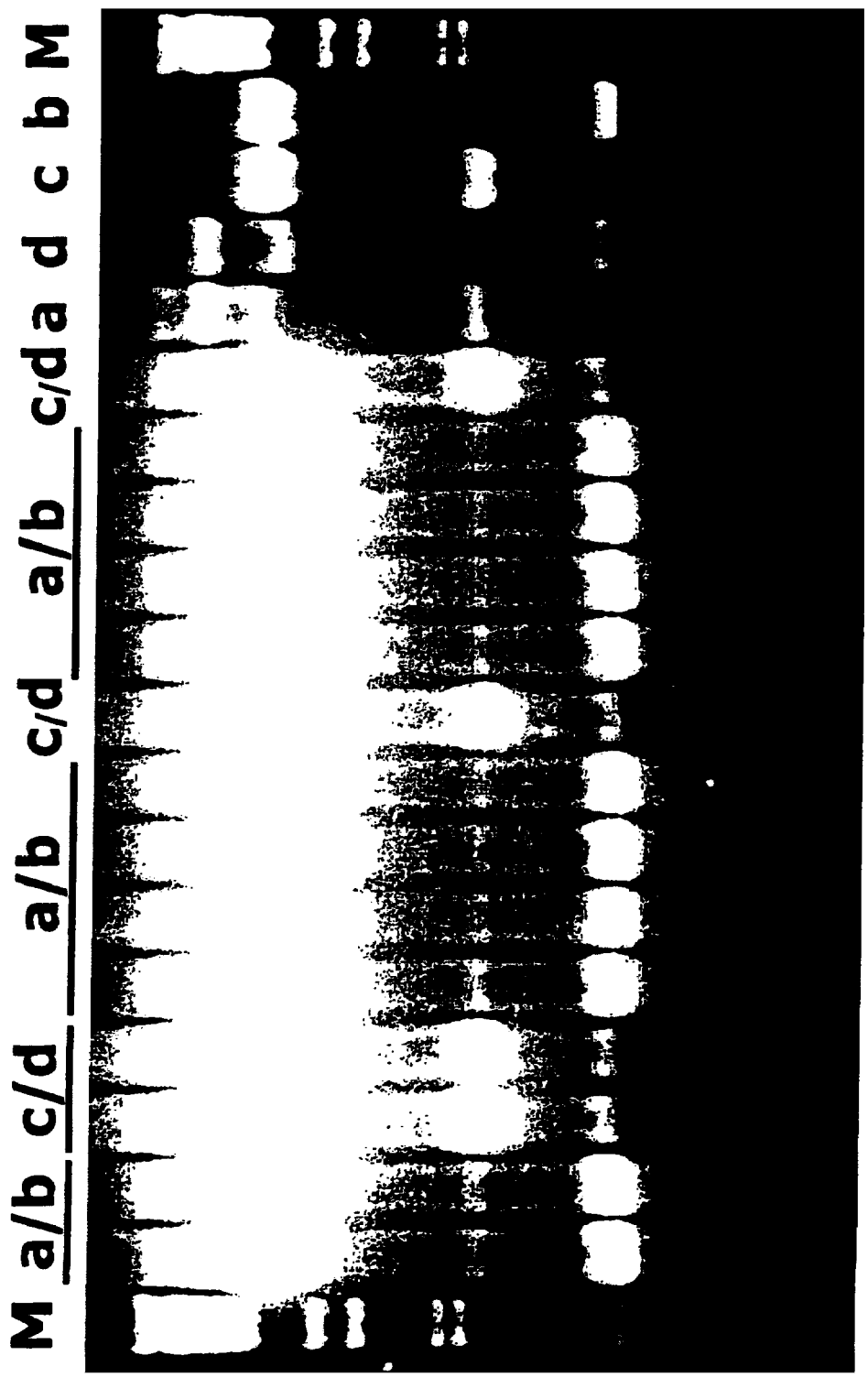

The pairs fpep3_1B-IR3 and pIG10.3-IMPp75 as well as fIMPp75-IR3 and pIG10.3-pep10 were co-transformed into DH5α, individual cam/amp resistant clones were grown and the culture supernatant was tested on K91 cells for SIP phage production (FIG. 10). The combinations fpep3_1B-IR3/pIG10.3-IMPp75 and fIMPp75-IR3/pIG10.3-pep10 gave a titer of $1.5 \times 10^5$ t.u./ml and $5 \times 10^3$ t.u./ml, respectively when assayed for cam/amp-resistant transductants. The titer for each combination when assayed on LB cam was nearly the same as when assayed on LB cam/amp. This demonstrated efficient co-packaging of phage and phagemid DNA to almost 100%, as seen before with the initial fjun_1B-R408IR and pOK1deltajun combination. To proof the existence of polyphages which individually co-transduce phage and phagemid DNA simultaneously, and to rule out the possibility of transduction of the two resistance markers by independent (and thus random) co-infection by two different phages which have only phage or phagemid packaged, a statistical test was performed. Defined, identical aliquots of bacterial culture supernatants of an individual co-transformant representing each of the two SIP vector combinations described above (fpep3_1B-IR3/pIG10.3-IMPp75 and fIMPp75-IR3/pIG10.3-pep10) were either used individually to infect K91 cells followed by selection on LB cam and LB amp plates, or the same supernatant aliquots from the two vector combinations were mixed before infection of K91 cells and selection on LB cam/amp. 117 cam-resistant, 328 amp-resistant and 141 cam/amp-resistant transforming units were present in the supernatant aliquot from the fIMPp75-IR3/pIG10.3-pep10 combination and 40 cam-resistant, 30 amp-resistant and 23 cam/amp-resistant transforming units were present in the supernatant aliquot from the fpep3_1B-IR3/pIG10.3-IMPp75 combination. The mix of both supernatant aliquots contained 166 cam-resistant and 162 cam/amp-resistant transforming units, exactely corresponding to the expected numbers which would be obtained by adding up the transducing units of the two individual aliquots. 48 cam/amp-resistant transductant colonies were picked from the plate were the mix of the two individual aliquots was used for infection and were analyzed by restriction digest. This showed that only the correct, SIP phage-producing vector combination (5 clones containing the fpep3_1B-IR3/pIG10.3-IMPp75 and 43 clones containing the fIMPp75-IR3/pIG10.3-pep10 combination; this represents a ratio of the two input vector combinations in the analyzed transductants of 1:8.6 (fpep3_1B-IR3/pIG10.3-IMPp75:fIMPp75-IR3/pIG10.3-pep10), which is very similar to the 1:6.1 (fpep3_1B-IR3/pIG10.3-IMPp75:fIMPp75-IR3/pIG10.3-pep10) ratio of double-resistant input phages in this experiment) occured in all analyzed transductants, verifying the presence of hetero-polyphages by ruling out the possibility of random co-infection and thus incorrect, random combination by two out of four possible monophage and/or homo-polyphage populations (fpep3_1B-IR3, pIG10.3-IMPp75, fIMPp75-IR3 and pIG10.3-pep10) each containing only one type of vector (phage or phagemid). Statistically, co-infection of the same bacterium by two separate phages was practically already excluded by the small numbers of infective phages containing at least one resistance marker (166 cam-resistant and 358 amp-resistant phages) which were used in the above experiment. Co-infection of the same bacterium (of a total of $10^7$ bacteria) by one of the 166 cam-resistant phages and one of the 358 amp-resistant phages has a probability of $6 \times 10^{-10}$. Moreover, in this scenario incorrect combinations of individual phage and phagemid vectors (e.g. fpep3_1B-IR3/pIG10.3-pep10 and fIMPp75-IR3/pIG10.3-IMPp75) would be possible. The fact that only the correct vector combinations were found in all 48 transductants analyzed from this experiment further proved that co-transduction by hetero-polyphage and not random co-infection by homo-polyphage or monophage was the mechnism by which double-resistance was transduced.

2.3.: Construction of a Phage-display System for Fab Display

The constructs described in 3.2. can easily be modified to achieve the display of Fabs or a Fab library. In fpep3_1B-IR3seq, the jun part can be replaced by a VL-CL light chain repertoire having the appropriate 3'- and 5'-restriction sites similarly as described for pep_3 to construct fVL_1B-R408IR. In pIG10.3-IMPp75, the IMPp75 construct can be replaced by a repertoire of VH-CH1 heavy chains. After co-transformation of both repertoires into host cells and expression, a library of phage particles displaying Fab fragments is produced. Since fpep3_1B-IR3seq was set up for a SIP experiment by having just the C-terminal domain of gIII, the corresponding Fab-displaying phage particles are non-infectious. By adding a target molecule fused to an infectivity-mediating particle (N1-N2 domain of gIIIp), phages displaying target-binding Fab fragments can be selected by infecting host cells.

By replacing the truncated gIII part described above by a full-length copy of gIII, a Fab-display library of infectious phage particles is obtained, which can be screened against immobilized targets. Binding phages can be eluted and used to infect host cells.

By selecting for transductants conferring cam/amp-resistance to their host cells, polyphage infections can be selected in both cases. Thereby the information about both chains of the selected Fab fragments can be retrieved.

The invention claimed is:

1. A filamentous polyphage particle which
   (a) contains
      (i) a first recombinant vector molecule that comprises a nucleic acid sequence, which encodes a fusion protein of a first member of a multimeric (poly)peptide complex fused to at least part of a filamentous phage coat protein, and that carries or encodes a first selectable and/or screenable property, and
      (ii) a second recombinant vector molecule that comprises a nucleic acid sequence, which encodes a second member of a multimeric (poly)peptide complex, and that carries or encodes a second selectable and/or screenable property different from said first property; and
   (b) displays said multimeric (poly)peptide complex at its surface.

2. The particle of claim 1, wherein said first vector is a phage vector and said second vector is a phagemid vector.

3. The particle of claim 1, wherein said first and second vectors are phagemid vectors.

4. The particle of claim 3, wherein said two phagemid vectors are compatible.

5. The particle of claim 3, wherein (i) said first phagemid vector comprises a ColE1 origin of replication and said second phagemid vector comprises a p15A plasmid origin of replication; or (ii) said first phagemid vector comprises a p15A origin of replication and said second phagemid vector comprises a ColE1 plasmid origin of replication.

6. The particle of claim 3, wherein (i) said first phagemid vector comprises a ColE1 origin of replication and said second phagemid vector comprises a mutated ColE1 origin of replication, wherein said mutated ColE1 origin of replication renders said second phagemid vector compatible with said first phagemid vector; or (ii) said first phagemid vector comprises a mutated ColE1 origin of replication and said second phagemid vector comprises a ColE1 plasmid origin of replication, wherein said mutated ColE1 origin of replication renders said first phagemid vector compatible with said second phagemid vector.

7. The particle of claim 1, wherein said vectors comprise different phage origins of replication.

8. The particle of claim 1 wherein said vectors are interference resistant.

9. The particle of claim 1, wherein at least one of said vectors is a phage or phagemid vector having one or more mutations in the phage intergenic regions) and/or in gene II.

10. The particle of claim 1, wherein at least one of said vectors is a phage or phagemid vector that is (i) an IR1 mutant or an IR2 mutant and (ii) interference resistant.

11. The particle of claim 1 wherein at least one of said first and second vector molecules is (i) a phage or phagemid vector comprising a hybrid nucleic acid sequence of f1-, fd-, and/or M13 derived sequences, and (ii) interference resistant.

12. The particle of claim 2, wherein said vector is SEQ ID NO: 31.

13. The particle of claim 2, wherein said phage vector is a mutant derived from SEQ ID NO:31 comprising the phage origin of replication from fpep3__1B-IRseq, the gene II from fpep3-1B-IRseq, or a combination of said phage origin of replication and said gene II.

14. The particle of claim 1, wherein any of said vectors that contains the gene VII contains an amber mutation in said gene VII.

15. The particle of claim 1, wherein said phage coat protein is gIIIp or gVIIIp.

16. The particle of claim 1, wherein said phage particle is infectious by having a full-length copy of gIIIp.

17. The particle of claim 1, wherein said phage particles are non-infectious by having no full-length copy of gIIIp, said fusion protein being formed with a truncated version of gIIIp, wherein the infectivity can be restored by interaction of the displayed multimeric polypeptide complexes with a corresponding partner coupled to an infectivity-mediating particle.

18. The particle of claim 17, wherein said truncated gIIIp comprises the C- terminal domain of gIIIp.

19. The particle of claim 18, wherein said truncated gIIIp is a derivative of phage fCA55, wherein said derivative leads to the formation of polyphages.

20. The particle of claim 1, wherein said multimeric polypeptide complex is a functional fragment of an immunoglobulin.

21. The particle of claim 20, wherein said fragment is an Fv, dsFv or Fab functional fragment.

22. The particle of claim 1, wherein said first and/or said second selectable and/or screenable property is the transcription of (i) a reporter gene selected from the group consisting of beta-galactosidase and alkaline phosphatase; or (ii) a nutritional marker selected from the group consisting of his3 and leu; or (iii) a resistance gene giving resistance to an antibiotic selected from the group consisting of ampicillin, chloramphenicol, kanamycin, zeocin, neomycin, tetracycline and streptomcycin.

23. The particle of claim 9, wherein the mutation is in the phage intergenic region corresponding to position 5986 of f1.

24. The particle of claim 9, wherein the mutation is in gene II corresponding to position 143 of f1.

25. The particle of claim 13, wherein said mutant comprises fd/fb 1 origin including mutation G5737>A (2976 in fpep3__1B-IR3seq), and/or the mutations G343>A (3989(in g II, and G601>T (4247) in g II/X.

26. The particle of claim 2, wherein said phagemid vector comprises the phage origin of replication from fpep3__1B-IRseq, the gene II from fpep3__1B-IRseq, or a combination of said phage origin of replication and said gene II.

* * * * *